(12) United States Patent
Lim et al.

(10) Patent No.: US 8,755,782 B2
(45) Date of Patent: Jun. 17, 2014

(54) MOBILE TERMINAL AND METHOD OF CONTROLLING OPERATION OF THE MOBILE TERMINAL

(75) Inventors: Hyebong Lim, Seoul (KR); Sunsang So, Seoul (KR)

(73) Assignee: LG Electronics Inc., Seoul (KR)

(*) Notice: Subject to any disclaimer, the term of this patent is extended or adjusted under 35 U.S.C. 154(b) by 358 days.

(21) Appl. No.: 13/210,239

(22) Filed: Aug. 15, 2011

(65) Prior Publication Data

US 2012/0049998 A1  Mar. 1, 2012

(30) Foreign Application Priority Data

Aug. 24, 2010 (KR) .................. 10-2010-0082136
Aug. 24, 2010 (KR) .................. 10-2010-0082137
Aug. 24, 2010 (KR) .................. 10-2010-0082139
Aug. 31, 2010 (KR) .................. 10-2010-0084934

(51) Int. Cl.
  *H04M 3/00*  (2006.01)
(52) U.S. Cl.
  USPC ..... 455/418; 455/419; 455/556.1; 455/556.2; 455/557; 455/575.6; 340/1.1

(58) Field of Classification Search
  USPC ........ 455/418, 419, 556.1, 556.2, 557, 575.6; 340/1.1
  See application file for complete search history.

(56) References Cited

U.S. PATENT DOCUMENTS

| 8,027,455 B2 * | 9/2011 | Moody et al. ................. 379/257 |
| 2006/0147021 A1 * | 7/2006 | Batni et al. ................ 379/221.08 |
| 2008/0154148 A1 * | 6/2008 | Chung et al. .................. 600/544 |

* cited by examiner

*Primary Examiner* — Olumide T Ajibade Akonai
(74) *Attorney, Agent, or Firm* — Lee, Hong, Degerman, Kang & Waimey

(57) ABSTRACT

A mobile terminal and a method of controlling the operation of the mobile terminal are provided. The method includes executing an application, determining whether a level of a brain wave of a user classified into a particular frequency band falls within a reference range, and storing at least image data or audio data relevant to the executed application if the level of the brain wave classified into the particular frequency band falls within the reference range.

19 Claims, 39 Drawing Sheets

FIG. 5
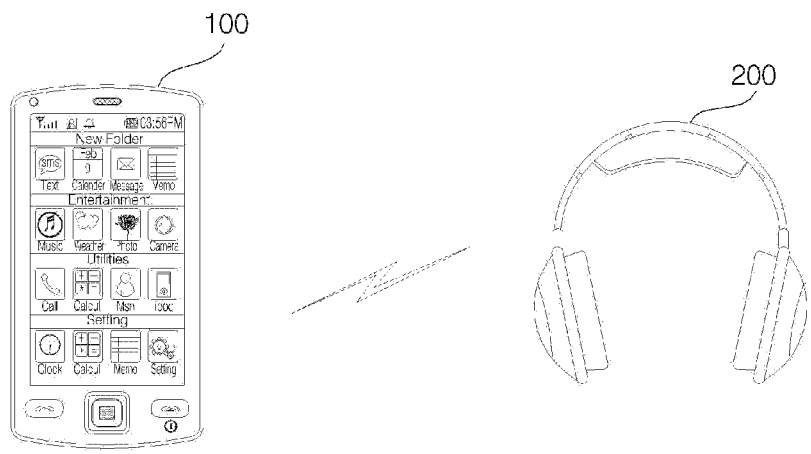
(a)
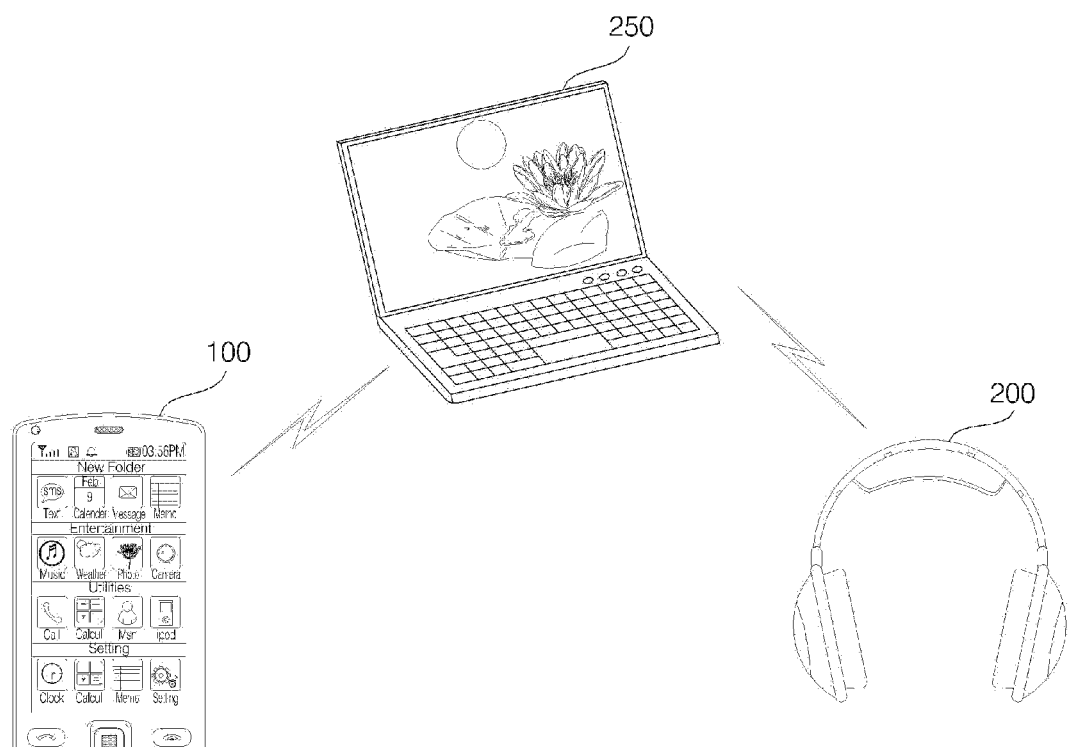
(b)

FIG. 7

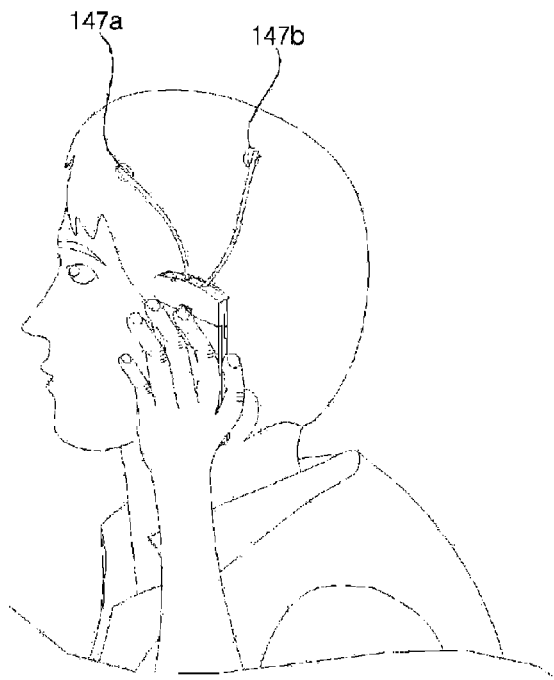

FIG. 8

| BRAINWAVE TYPE | FREQUENCY RANGE | HUMAN STATES OF MIND |
|---|---|---|
| DALTA | 0.1Hz to 3Hz | DEEP SLEEP |
| THETA | 4Hz to 7Hz | DROWSINESS, SHALLOW SLEEP, HIGHLY-CREATIVE STATE |
| SLOW ALPHA | 8Hz to 9Hz | RELAXATION, MEDITATION |
| MIDDLE ALPHA | 10Hz to 12Hz | STUDYING, MENTAL CONCENTRATION, HEIGHTENED MEMORY, STRESS-RELIEF |
| FAST ALPHA | 12Hz to 13Hz | ATTENTION, TENSION |
| BETA | 14Hz to 30Hz | NORMAL WAKING CONSCIOUSNESS |
| GAMMA | 30Hz to 100Hz | UNEASINESS, EXCITEMENT |

(a)          (b)

(a)　　　　　　　　(b)

(a)           (b)

(a)  (b)

MOBILE TERMINAL AND METHOD OF CONTROLLING OPERATION OF THE MOBILE TERMINAL

CROSS-REFERENCE TO RELATED APPLICATIONS

This application claims the priority benefit of Korean Patent Application Nos. 10-2010-0082136, No. 10-2010-0082137, and No. 10-2010-0082139, all filed on Aug. 24, 2010 in the Korean Intellectual Property Office and Korean Patent Application No. 10-2010-0084934, filed on Aug. 31, 2010 in the Korean Intellectual Property Office, the disclosures of all which are incorporated herein by reference.

FIELD OF THE INVENTION

The present invention is directed to a mobile terminal and a method of controlling the operation of the mobile terminal, and more particularly, to a mobile terminal and a method of controlling the operation of the mobile terminal in which various services can be provided based on a brain wave measurement obtained from a user.

DESCRIPTION OF THE RELATED ART

Mobile terminals are portable devices, which can provide users with various services such as a voice calling service, a video calling service, an information input/output service, and a data storage service. As the types of services provided by mobile terminals diversify, an increasing number of mobile terminals have been equipped with various complicated functions such as capturing photos or moving pictures, playing music files or moving image files, providing game programs, receiving broadcast programs and providing wireless Internet services and have also evolved into multimedia players.

Human brain activities result from the activities of neurons. Electroencephalography (EEG) is the recording of electrical activity along the scalp that is produced by neurons within the brain. EEG recordings vary according to the state of a subject or the type of task the subject participates in.

The measurement of brain waves is generally performed through the analysis of the pattern of the activity of neurons within the brain and has increasingly expanded its application to various fields, such as the field of brain computer interfaces (BCIs), which aims at building a direct interface between a machine and a human. Research has recently been carried out on ways to apply BCI to a mobile terminal and provide a variety of mobile services to a user based on a brain wave measurement obtained from the user.

SUMMARY OF THE INVENTION

In one aspect of the present invention, a method of controlling operation of a mobile terminal is provided. The method includes executing an application, determining whether a level of a brain wave that is classified into a specific frequency band is within a reference range and storing at least image data or audio data relevant to the execution of the application if the level of the brain wave is within the reference range.

It is contemplated that the reference range represents a specific state of mind of a user. It is further contemplated that the method further includes displaying an indicator to notify a user that the at least image data or audio data is being stored while storing the at least image data or audio data.

It is contemplated that the image data includes a plurality of images displayed during a period of time when the brain wave is within the reference range. It is further contemplated that the audio data includes at least a user's voice or audio data output upon executing the application.

It is contemplated that the audio data includes audio data transmitted or received by the mobile terminal during a period of time when the brain wave is within the reference range. It is further contemplated that the method further includes generating a highlight file based on at least the image data or audio data when the execution of the application is complete.

It is contemplated that the method further includes playing at least the image data or audio data in response to receiving a highlight play command for the application. It is further contemplated that the application includes at least a call application, a video player application, an audio player application, a still image viewer application, a game application, a broadcast program viewer application or a web application.

It is contemplated that the specific frequency band includes at least a beta-wave frequency band or an alpha-wave frequency band. It is further contemplated that storing the at least image data or audio data includes capturing the image data and storing the captured image data in an image format. Preferably, storing the at least image data or audio data includes matching the image data and audio data in consideration of the playback time of the image data and audio data.

In another aspect of the present invention, a mobile terminal is provided. The mobile terminal includes a memory configured to store information, an output unit configured to output results of execution of an application in the mobile terminal, the results output external to the mobile terminal and a controller configured to execute the application, determine if a level of a brain wave classified into a specific frequency band is within a reference range and store at least image data or audio data relevant to the execution of the application in the memory if the level of the brain wave is within a reference range.

It is contemplated that the reference range represents a specific state of mind of a user. It is further contemplated that the controller is further configured to display an indicator to notify a user that the at least image data or audio data is being stored while storing the at least image data or audio data.

It is contemplated that the at least image data or audio data includes data output during a period of time when the brain wave is within the reference range. It is further contemplated that the audio data includes at least a user's voice or audio data output upon executing the application.

In another aspect of the present invention, a method of controlling operation of a mobile terminal is provided. The method includes generating first brain wave information of a user of the mobile terminal, receiving second brain wave information of a user of another mobile terminal, comparing the first brain wave information to the second brain wave information, generating brain harmony information indicating a level of harmony between the user of the mobile terminal and the user of the another mobile terminal based on the results of the comparison and controlling an operation relevant to the other mobile terminal based on the brain harmony information.

In another aspect of the present invention, a method of controlling operation of a mobile terminal is provided. The method includes receiving a communication event, obtaining at least image data, audio data, or haptic data corresponding to a brain wave pattern and providing the at least image data, audio data, or haptic data according to an operating mode of the mobile terminal.

In another aspect of the present invention, a method of controlling operation of a mobile terminal is provided. The method includes displaying an indicator associated with a reference brain wave during an application mode, determining a level of pattern similarity between a received brain wave and the reference brain wave and performing an operation according to a command corresponding to the displayed indicator if the level of pattern similarity is higher than a predefined level.

Additional features and advantages of the invention will be set forth in the description which follows, and in part will be apparent from the description, or may be learned by practice of the invention. It is to be understood that both the foregoing general description and the following detailed description of the present invention are exemplary and explanatory and are intended to provide further explanation of the invention as claimed.

These and other embodiments will also become readily apparent to those skilled in the art from the following detailed description of the embodiments having reference to the attached figures, the invention not being limited to any particular embodiments disclosed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

FIG. 5 is a diagram illustrating an example connecting the audio output device shown in FIG. 4 to the mobile terminal shown in FIG. 1.

FIG. 7 is a diagram illustrating an example of a brain wave sensor in use during a call.

FIG. 8 is a diagram illustrating a table showing correspondence between brain wave frequency bands and human states of mind.

DETAILED DESCRIPTION OF THE PREFERRED EMBODIMENTS

Figure 1:
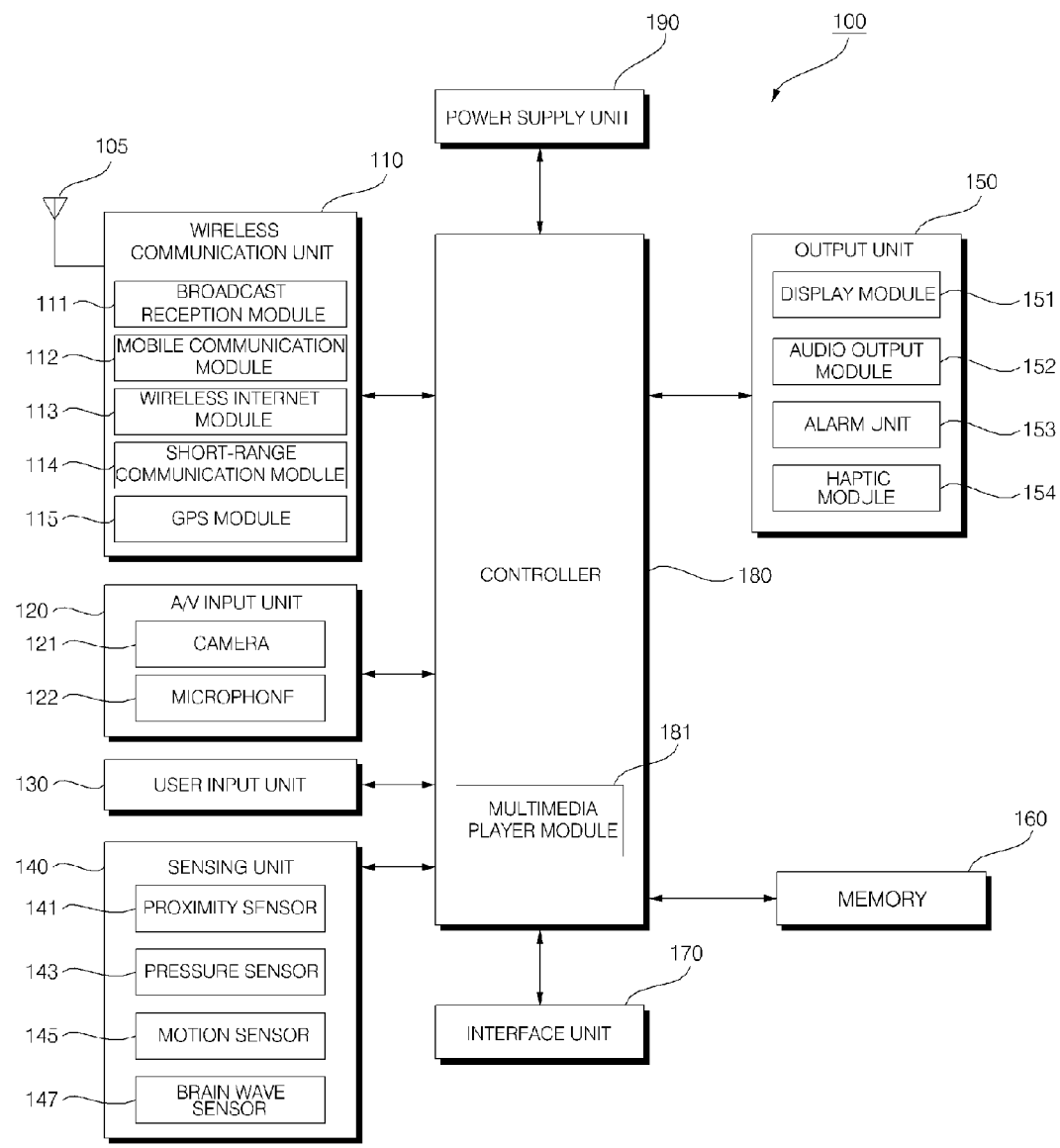
FIG. 1 is a block diagram of a mobile terminal according to an embodiment of the present invention.

FIG. 1 is a block diagram of a mobile terminal 100 according to an embodiment of the present invention. Referring to FIG. 1, the mobile terminal 100 includes a wireless communication unit 110, an A/V (audio/video) input unit 120, a user input unit 130, a sensing unit 140, an output unit 150, a memory 160, an interface unit 170, a controller 180, and a power supply unit 190. FIG. 1 shows the mobile terminal 100 having various components, but it is understood that implementing all of the illustrated components is not a requirement. Greater or fewer components may alternatively be implemented.

For example, two or more of the wireless communication unit 110, the A/V input unit 120, the user input unit 130, the sensing unit 140, the output unit 150, the memory 160, the interface unit 170, the controller 180, and the power supply unit 190 may be incorporated into a single unit. Alternately, some of the wireless communication unit 110, the A/V input unit 120, the user input unit 130, the sensing unit 140, the output unit 150, the memory 160, the interface unit 170, the controller 180, and the power supply unit 190 may be divided into two or more smaller units.

FIG. 1 shows a wireless communication unit 110 configured with several commonly implemented components. For example, the wireless communication unit 110 typically includes one or more components that permit wireless communication between the mobile terminal 100 and a wireless communication system or network within which the mobile terminal is located.

The wireless communication unit 110 can include a broadcast receiving module 111, a mobile communication module 112, a wireless Internet module 113, a short-range communication module 114, and a global positioning system (GPS) module 115. At least two broadcast receiving modules 111 can be provided to facilitate simultaneous reception of at least two broadcast channels or broadcast channel switching.

The broadcast receiving module 111 receives a broadcast signal and/or broadcast associated information from an external broadcast managing server via a broadcast channel. The broadcast channel may include a satellite channel or a terrestrial channel.

The broadcast managing server refers generally to a system that transmits a broadcast signal and/or broadcast associated information or a server which is provided with a previously generated broadcast signal and/or broadcast associated information. The broadcast messaging server then transmits the provided signal or information to a terminal.

Examples of broadcast associated information include information associated with a broadcast channel, a broadcast program, and a broadcast service provider. For example, the broadcast associated information may include an electronic program guide (EPG) of digital multimedia broadcasting (DMB) and electronic service guide (ESG) of digital video broadcast-handheld (DVB-H).

The broadcast signal may be implemented as a TV broadcast signal, a radio broadcast signal, or a data broadcast signal. The broadcast signal may further include a broadcast signal combined with a TV or radio broadcast signal.

The broadcast receiving module 111 may be configured to receive broadcast signals transmitted from various types of broadcast systems. By way of non-limiting examples, such broadcasting systems include digital multimedia broadcasting-terrestrial (DMB-T), digital multimedia broadcasting-satellite (DMB-S), digital video broadcast-handheld (DVB-H), DVB-CBMS, OMA-BCAST, the data broadcasting system known as media forward link only (MediaFLO®) and integrated services digital broadcast-terrestrial (ISDB-T).

The broadcast reception module 111 may be configured to be suitable for nearly all types of broadcasting systems other than those set forth herein. The broadcast signal and/or the broadcast-related information received by the broadcast reception module 111 may be stored in the memory 160.

The mobile communication module 112 communicates wireless signals with one or more network entities, such as base station or Node-B. Such signals may represent, for example, audio, video, multimedia, control signaling, or data.

The wireless Internet module 113 supports Internet access for the mobile terminal 100. The wireless Internet module 113 may be internally or externally coupled to the mobile terminal 100. The wireless Internet technology can include, for example, WLAN (Wireless LAN), Wibro (Wireless broadband), Wimax (World Interoperability for Microwave Access), or HSDPA (High Speed Downlink Packet Access).

The short-range communication module 114 facilitates relatively short-range communications. Suitable technologies for short-range communication may include, but are not limited to, radio frequency identification (RFID), infrared data association (IrDA), ultra-wideband (UWB), as well at the networking technologies commonly referred to as Bluetooth® and ZigBee®.

GPS module 115 identifies or otherwise obtains the location of the mobile terminal 100. The GPS module 115 may receive position information from a plurality of GPS satellites.

The audio/video (A/V) input unit 120 is configured to provide audio or video signal input to the mobile terminal 100. As shown, the A/V input unit 120 includes a camera 121 and a microphone 122.

The camera 121 receives and processes image frames of still pictures or video, which are obtained by an image sensor in a video call mode or a photographing mode. The processed image frames can be displayed on the display unit 151. The image frames processed by the camera 121 can be stored in the memory unit 160 or can be externally transmitted via the wireless communication unit 110.

The microphone 122 receives an external audio signal while the mobile terminal 100 is in a particular mode, such as phone call mode, recording mode or voice recognition mode. The audio signal is processed and converted into digital data. The processed audio data is transformed into a format transmittable to a mobile communication base station via the mobile communication module 112 in a call mode. The microphone 122 typically includes assorted noise removing algorithms to remove noise generated in the course of receiving the external audio signal.

Data generated by the A/V input unit 120 may be stored in the memory 160, utilized by the output unit 150, or transmitted via one or more modules of the wireless communication unit 110. If desired, two or more cameras 121 or microphones 122 may be provided.

The user input unit 130 generates input data responsive to user manipulation of an associated input device or devices. Examples of such devices include a keypad, a dome switch, a touchpad such as static pressure/capacitance, a jog wheel and a jog switch.

The sensing unit 140 provides status measurements of various aspects of the mobile terminal 100. For example, the sensing unit 140 may detect an open/close status of the mobile terminal 100, the relative positioning of components such as a display and keypad, a change of position of the mobile terminal or a component of the mobile terminal, a presence or absence of user contact with the mobile terminal, or orientation or acceleration/deceleration of the mobile terminal.

The mobile terminal 100 may be configured as a slide-type mobile terminal and the sensing unit 140 may sense whether a sliding portion of the mobile terminal is open or closed. The sensing unit 140 may also sense the presence or absence of power provided by the power supply unit 190 or the presence or absence of a coupling or other connection between the interface unit 170 and an external device.

The sensing unit 140 may include a proximity sensor 141, a pressure sensor 143, a motion sensor 145 and a brain wave sensor 147. The proximity sensor 141 may determine whether there is an object nearby and approaching the mobile terminal 100 without any mechanical contact with the entity. More specifically, the proximity sensor 141 may detect an object that is nearby and approaching by detecting a change in an alternating magnetic field or the rate of change of static capacitance. The sensing unit 140 may include two or more proximity sensors 141.

The pressure sensor 143 may determine whether pressure is being applied to the mobile terminal 100 or may measure the level of pressure, if any, applied to the mobile terminal 100. The pressure sensor 143 may be installed in a certain part of the mobile terminal 100 where the detection of pressure is necessary.

For example, the pressure sensor 143 may be installed in the display module 151. In this way, it is possible to differentiate a typical touch input from a pressure touch input that is generated using a higher pressure level than used to generate a typical touch input based on data provided by the pressure sensor 143. In addition, when a pressure touch input is received through the display module 151, it is possible to determine the level of pressure applied to the display module 151 upon the detection of a pressure touch input based on data provided by the pressure sensor 143.

The motion sensor 145 may determine the location and motion of the mobile terminal 100 using an acceleration sensor or a gyro sensor. Gyro sensors are sensors for measuring angular velocity that may determine the relative direction of rotation of the mobile terminal 100 with respect to a reference direction.

Acceleration sensors are devices for converting a vibration caused by acceleration into an electric signal. With recent developments in micro-electromechanical system (MEMS) technology, acceleration sensors have been widely used in various products for various purposes ranging from detecting large motions, such as those caused by car collisions, to detecting minute motions, such as the motion of the hand in gaming input devices. Generally, one or more acceleration sensors representing two or three axial directions are incorporated into a single package.

There are some cases when the detection of only one axial direction, such as a Z-axis direction, is necessary. When an X- or Y-axis acceleration sensor is required instead of a Z-axis acceleration sensor, the X- or Y-axis acceleration sensor may be mounted on an additional substrate, and the additional substrate that is mounted on a main substrate.

The brain wave sensor 147 measures brain waves from the human brain. Brain wave measurements are largely classified into low pass filtering (LPF) data, electrocorticography (ECoG) data, and electroencephalogram (EEG) data according to which part of the brain they are obtained from. More specifically, the brain wave sensor 147 may detect and measure an EEG signal from the scalp.

The output unit 150 generates outputs relevant to the senses such as sight, hearing, and touch. The output unit 150 is illustrated in FIG. 1 as having a display unit 151, an audio output module 152, an alarm unit 153, and a haptic module 154.

The display unit 151 is typically implemented to visually display (output) information associated with the mobile terminal 100. For example, if the mobile terminal 100 is operating in a phone call mode, the display unit 151 will generally provide a user interface (UI) or graphical user interface (GUI) that includes information associated with placing, conducting, and terminating a phone call. If the mobile terminal 100 is in a video call mode or a photographing mode, the display unit 151 may additionally or alternatively display images which are associated with these modes, the UI or the GUI.

One particular implementation of the present invention includes the display unit 151 configured as a touch screen working in cooperation with an input device, such as a touchpad. This configuration permits the display unit 151 to function both as an output device and an input device.

If the display module 151 and the user input unit 130 form a layer structure together that is implemented as a touch screen, the display module 151 may be used as both an output device and an input device. If the display module 151 is implemented as a touch screen, it may also include a touch screen panel and a touch screen panel controller.

The touch screen panel is a transparent panel attached to the exterior of the mobile terminal 100 and may be connected to an internal bus of the mobile terminal. The touch screen panel keeps monitoring whether the touch screen panel is being touched by the user.

Once a touch input to the touch screen panel is received, the touch screen panel transmits a number of signals corresponding to the touch input to a touch screen panel controller. The touch screen panel controller processes the signals transmitted by the touch screen panel and transmits the processed signals to the controller 180. Then, the controller 180 determines whether a touch input has been generated and which part of the touch screen panel has been touched based on the processed signals transmitted by the touch screen panel controller.

The display module 151 may include electronic paper (e-paper). The display module 151 may be implemented as e-paper by using electrostatic-charged hemispherical twist balls, electrophoretic deposition, or microcapsules.

E-paper is a type of reflective display technology and can provide as high resolution as ordinary ink on paper, wide viewing angles, and excellent visual properties. E-paper can be implemented on various types of substrates such as a plastic, metallic or paper substrate and can display and maintain an image thereon even after power is cut off. In addition, e-paper can reduce the power consumption of the mobile terminal 100 because it does not require a backlight assembly.

The display unit 151 may be implemented using known display technologies including a liquid crystal display (LCD), a thin film transistor-liquid crystal display (TFT- LCD), an organic light-emitting diode display (OLED), a flexible display and a three-dimensional (3D) display. The mobile terminal 100 may include two or more display modules 151. For example, the mobile terminal 100 may include an external display module (not shown) and an internal display module (not shown).

The audio output module 152 supports the audio output requirements of the mobile terminal 100. The audio output module 152 may be implemented using one or more speakers, buzzers, other audio producing devices, or combinations thereof.

The audio output module 152 functions in various modes such as call-receiving mode, call-placing mode, recording mode, voice recognition mode and broadcast reception mode. The audio output module 152 outputs audio relating to a particular function or status, such as call received, message received, or errors.

The alarm module 153 may output an alarm signal indicating the occurrence of an event in the mobile terminal 100. An alarm signal for notifying the user of the occurrence of an event may be output not only by the alarm module 153 but also by the display module 151 or the audio output module 153.

Examples of the event include receiving a call signal, receiving a message, and receiving a key signal. Examples of the alarm signal output by the alarm module 153 include an audio signal, a video signal and a vibration signal.

More specifically, the alarm module 153 may output an alarm signal upon receiving a call signal or a message. In addition, the alarm module 153 may receive a key signal and output an alarm signal as feedback to the key signal. In this way, the user may be able to easily recognize the occurrence of an event based on an alarm signal output by the alarm module 153.

The haptic module 154 generates various tactile effects that can be sensed by a user. Vibration is a representative tactile effect generated by the haptic module 154. Strength and pattern of the vibration generated by the haptic module 154 are controllable. For example, different vibrations may be output by being synthesized together or may be output in sequence.

The haptic module 154 is able to generate various tactile effects as well as vibration. For example, the haptic module 154 may generate the effect of an arrangement of pins vertically moving against a contact skin surface, the effect of an injection/suction power of air though an injection/suction hole, the effect of skimming over a skin surface, the effect of contact with an electrode, the effect of electrostatic force, or the effect of hot/cold using an endothermic or exothermic device.

The haptic module 154 can be implemented to enable a user to sense the tactile effect through a muscle sense of a finger, an arm or other body part as well as to transfer the tactile effect through a direct contact. At least two haptic modules 154 can be provided in the mobile terminal 100 in accordance with the corresponding configuration of the mobile terminal.

The memory 160 is generally used to store various types of data to support the processing, control, and storage requirements of the mobile terminal 100. Examples of data stored in the memory 160 include program instructions for applications operating in the mobile terminal 100, contact data, phonebook data, messages, pictures, and video.

The memory 160 may be implemented using any type or combination of suitable volatile and non-volatile memory or storage devices. Examples of memory types are random access memory (RAM), static random access memory (SRAM), electrically erasable programmable read-only memory (EEPROM), erasable programmable read-only memory (EPROM), programmable read-only memory (PROM), read-only memory (ROM), magnetic memory, flash memory, magnetic or optical disk memory, multimedia card micro type memory, card-type memory (e.g., SD memory, XD memory), and other similar memory or data storage devices. The mobile terminal 100 may operate in association with web storage for performing a storage function of the memory 160 on the Internet.

The interface unit 170 is often implemented to couple the mobile terminal 100 with external devices. The interface unit 170 receives data from the external devices or is supplied with power and then transfers the data or power to the respective elements of the mobile terminal 100 or enables data within the mobile terminal 100 to be transferred to the external devices. The interface unit 170 may be configured using a wired/wireless headset port, an external charger port, a wired/wireless data port, a memory card port, a port for coupling to a device having an identity module, audio input/output ports, video input/output ports, or an earphone port.

The identity module is a chip for storing various kinds of information for authenticating a user's authority to use the mobile terminal 100 and can include a User Identify Module (UIM), a Subscriber Identity Module (SIM), or a Universal Subscriber Identity Module (USIM). A device having the identity module, or an 'identity device', can be manufactured as a smart card. Therefore, the identity device is connectible to the mobile terminal 100 via a corresponding port.

When the mobile terminal 100 is connected to an external cradle, the interface unit 170 provides a passage for supplying the mobile terminal with power from the cradle or a passage for delivering various command signals to the mobile terminal that are input from the cradle by a user. Each of the various command signals input from the cradle or power can operate as a signal enabling the mobile terminal 100 to determine that it is correctly loaded in the cradle.

The controller 180 typically controls the overall operations of the mobile terminal 100. For example, the controller 180 performs the control and processing associated with voice calls, data communications, instant message communication, video calls, camera operations and recording operations. Furthermore, the controller 180 may perform a pattern recognizing process for recognizing a writing input or a picture drawing input performed on the touch screen as characters or images.

The controller 180 may include a multimedia module 181 that provides multimedia playback. The multimedia module 181 may be configured as part of the controller 180 or implemented as a separate component.

The power supply unit 190 provides power required by the various components for the mobile terminal 100. The power may be internal power, external power, or combinations thereof.

The mobile terminal 100 may include a wired/wireless communication system or a satellite communication system and may be able to operate in a communication system capable of transmitting data in units of frames or packets. The exterior structure of the mobile terminal 100 will be described in detail with reference to FIGS. 2 and 3.

The present invention can be applied to nearly all types of mobile terminals such as a folder-type, a bar-type, a swing-type and a slider-type mobile terminal. However, for convenience, it is assumed that the mobile terminal 100 is a bar-type mobile terminal, equipped with a full touch screen.

Figure 2:
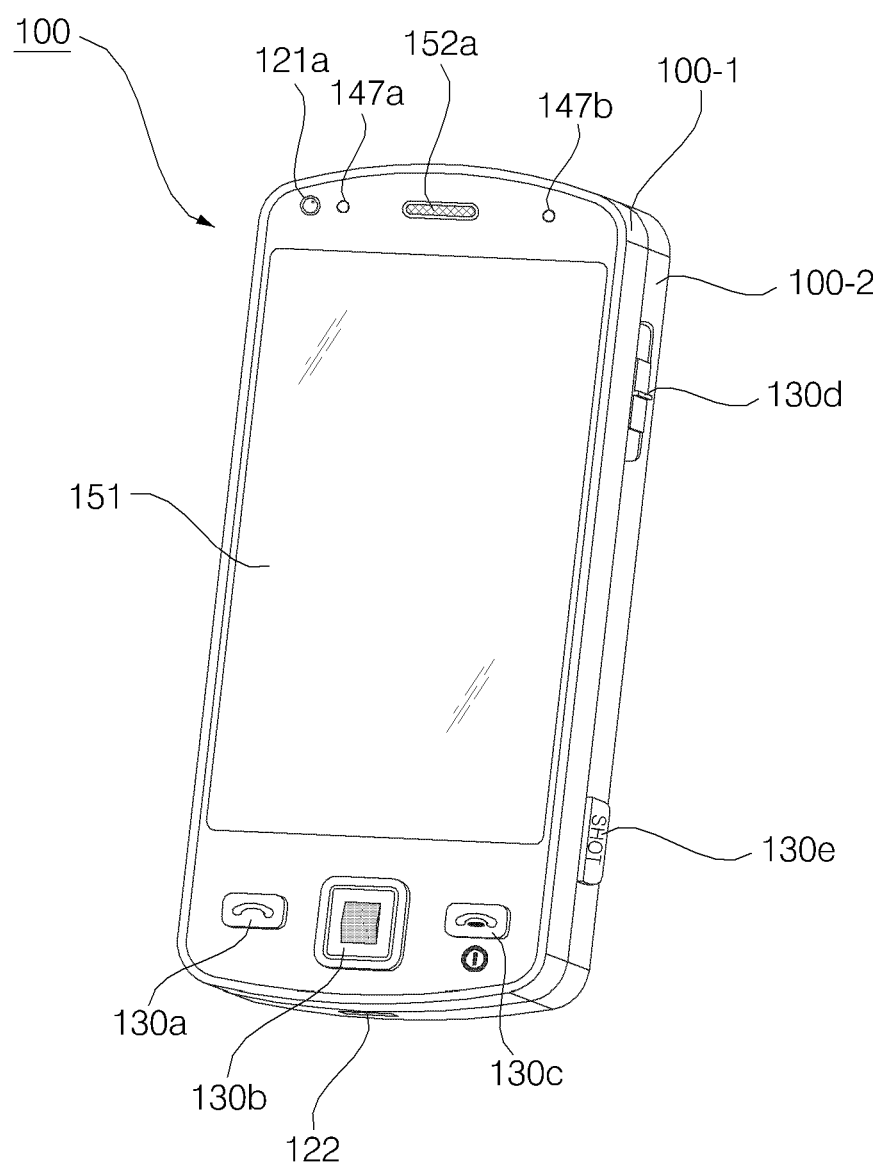
FIG. 2 is a front perspective view of the mobile terminal shown in FIG. 1.
Figure 3:
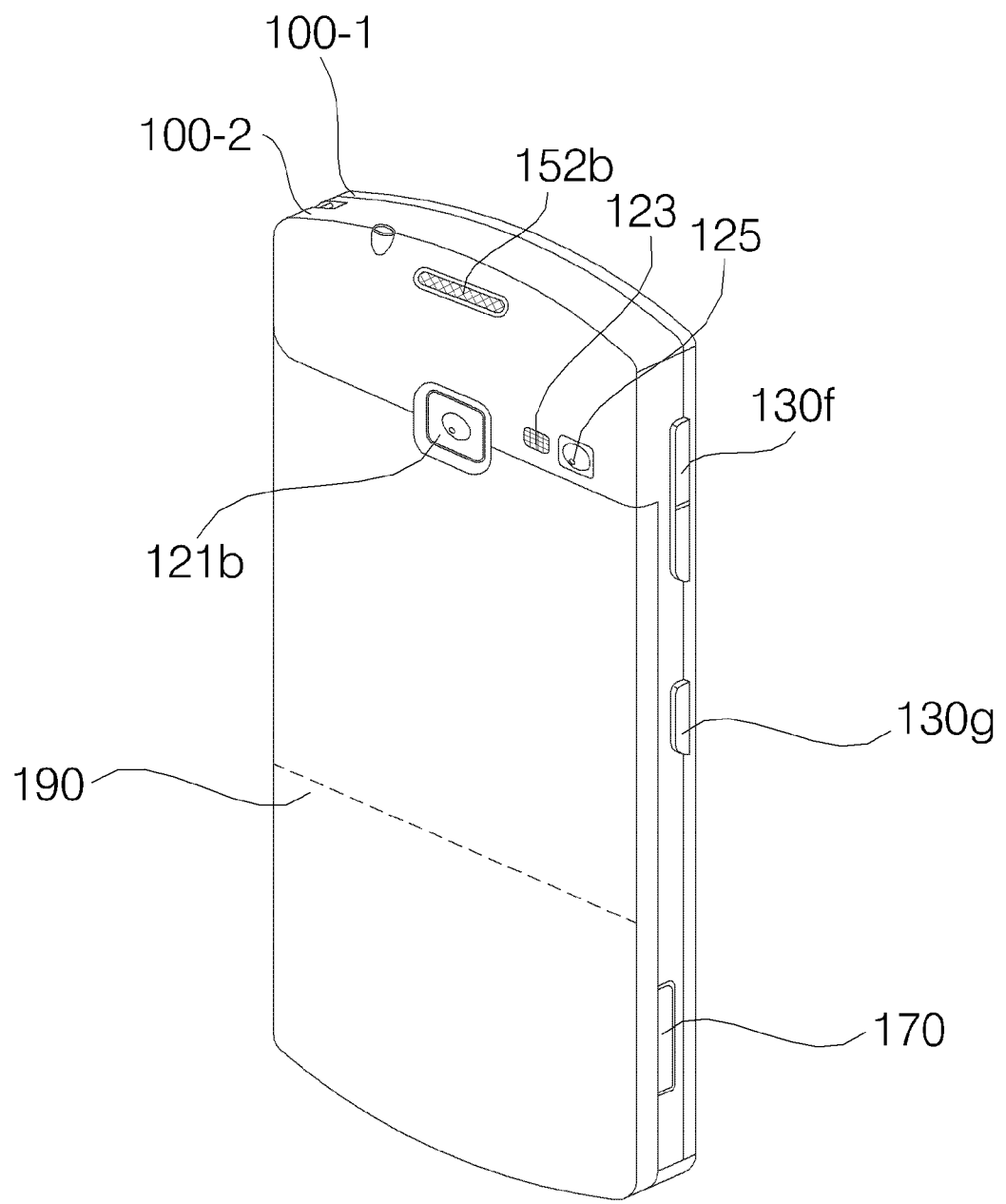
FIG. 3 is a rear perspective view of the mobile terminal shown in FIG. 1.

FIG. 2 is a front perspective view of the mobile terminal 100. FIG. 3 is a rear perspective view of the mobile terminal.

Referring to FIG. 2, the exterior of the mobile terminal 100 may be formed by a front case 100-1 and a rear case 100-2. Various electronic devices may be installed in the space formed by the front case 100-1 and the rear case 100-2. The front case 100-1 and the rear case 100-2 may be formed of a synthetic resin through injection molding. Alternatively, the front case 100-1 and the rear case 100-2 may be formed of a metal such as stainless steel (STS) or titanium (Ti).

The display module 151, a first audio output module 152a, a first camera 121a, first and second brain wave sensors 147a and 147b and first through third user input modules 130a through 130c may be disposed in the main body of the mobile terminal 100 and, specifically, on the front case 100-1. The first and second brain wave sensors 147a and 147b may be disposed on various parts of the mobile terminal 100, other than the front case 100-1, where they can be placed in contact with the user. Fourth and fifth user input modules 130d and 130e and the microphone 122 may be disposed on one side of the rear case 100-2.

If a touch pad is configured to overlap the display module 151 to form a mutual layer structure, the display module may serve as a touch screen. The user can enter various information to the mobile terminal 100 simply by touching the display module 151.

The first audio output module 152a may be implemented as a receiver or a speaker. The first camera 121a may be configured to be suitable for capturing a still or moving image of the user. The microphone 122 may be configured to receive the user's voice or other sounds.

The first through fifth user input modules 130a through 130e and sixth and seventh user input modules 130f and 130g (see FIG. 3) may be collectively referred to as the user input unit 130. Any means can be employed as the first through seventh user input modules 130a through 130f as long as they can operate in a tactile manner. For example, the user input unit 130 may be implemented as a dome switch or a touch pad that can receive a command or information according to a pressing or a touch operation by the user, or may be implemented as a wheel or jog dial for rotating a key or as a joystick.

The first through third user input modules 130a through 130c may operate as function keys for entering a command such as start, end, or scroll. The fourth user input module 130d may operate as a function key for selecting an operating mode for the mobile terminal 100. The fifth user input module 130e may operate as a hot key for activating a special function within the mobile terminal 100.

Referring to FIG. 3, a second camera 121b may be additionally provided at the rear of the rear case 100-2. The sixth and seventh user input modules 130f and 130g and the interface unit 170 may be disposed on one side of the rear case 100-2.

The second camera 121b may have an image capture direction which is substantially opposite to the image capture direction of the first camera 121a. The second camera 120b may have a different resolution than the first camera 121a.

A flash 123 and a mirror 125 may be disposed adjacent to the second camera 121b. When an image of a subject is captured with the second camera 121b, the flash may illuminate the subject. The mirror may allow the user to see himself or herself in order to perform self image capture using the second camera 121b.

A second audio output module 152b may be additionally provided on the rear case 100-2. The second first audio output module 152b may provide a stereo function with the first audio output module 152 on the front case 100-1. The second audio output module 152b may also be used in a speakerphone mode.

The interface unit 170 may used as a passage allowing the mobile terminal 100 to exchange data with an external device either via a fixed line or wirelessly.

A broadcast signal reception antenna may be disposed at one side of the front or rear case 100-1 or 100-2, in addition to an antenna used for call communication. The broadcast signal reception antenna may be installed such that it can be extended from the front or rear case 100-1 or 100-2.

The power supply unit 190 may be mounted on the rear case 100-2 in order to provide power to the mobile terminal 100. The power supply unit 190 may be a chargeable battery which can be detachably combined with the rear case 100-2 for charging.

The elements that have been described as being provided on the rear case 100-2 may be provided on the front case 100-1. In addition, the first camera 121a may be configured to be rotatable to allow image capturing in various directions and the second camera 121b may be optional.

Figure 4:
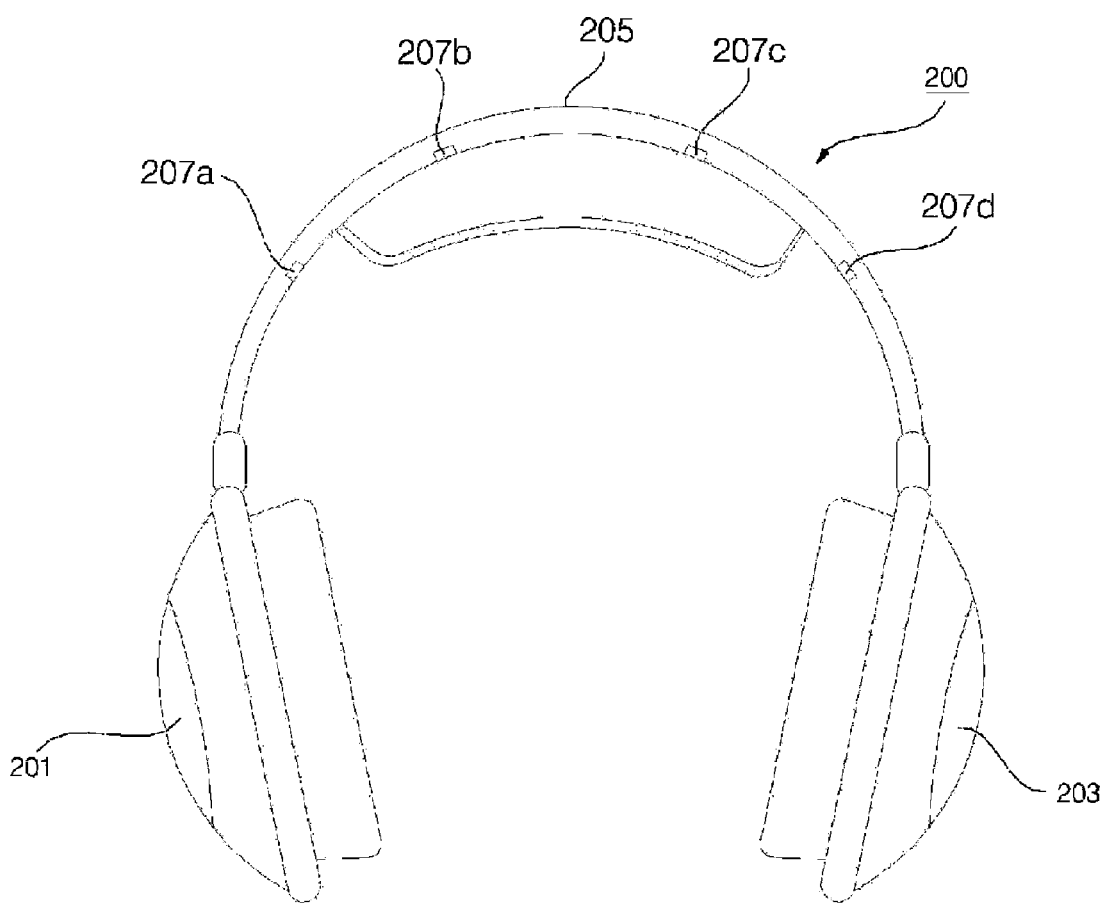
FIG. 4 is a diagram illustrating an audio output device that can be connected to the mobile terminal shown in FIG. 1.

FIG. 4 illustrates an audio output device 200 that can be connected to the mobile terminal 100. FIG. 5 illustrates the audio output device 200 connected to the mobile terminal 100.

Referring to FIG. 4, the audio output device 200 includes first and second audio output units 201 and 203 and a frame 205 connecting the first and second audio output units. The audio output device 200 can be worn on the head of a user.

The audio output device 200 may be connected to the mobile terminal 100 via wires or via short-range communication such as Bluetooth™. The audio output device 200 may receive audio/video (A/V) data from the mobile terminal 100 and may then output audio signals corresponding to the A/V data directly to the ears of the user.

One or more brain wave sensors 207a through 207d may be disposed in the frame 205 of the audio output device 200 in order to measure brain waves from the scalp of the user. A brain wave measurement obtained by the audio output device 200 may be subject to signal processing and then transmitted to the mobile terminal 100 either directly, as shown in FIG. 5(a), or via another device 250, as shown in FIG. 5(b). The brain waves of the user may be measured by the audio output device 200, such as a headset or earphones, or the brain wave sensor 147 of the mobile terminal 100.

The brain wave sensor 147 may include a signal processor (not shown). The signal processor converts a time-domain brain wave signal into a frequency-domain brain wave signal in order to determine the frequency band of a brain wave measurement obtained from the user. In this way, it is possible to determine the state of mind of the user based on the frequency band of the brain wave measurement obtained from the user by referencing a table showing the correspondence between various brain wave frequency bands and various human states of mind.

The brain wave sensor 147 may be located in a portion of the mobile terminal 100 where it can be placed in contact with the user. The brain wave sensor 147 may be configured to be retracted and extended from the mobile terminal 100.

Figure 6:
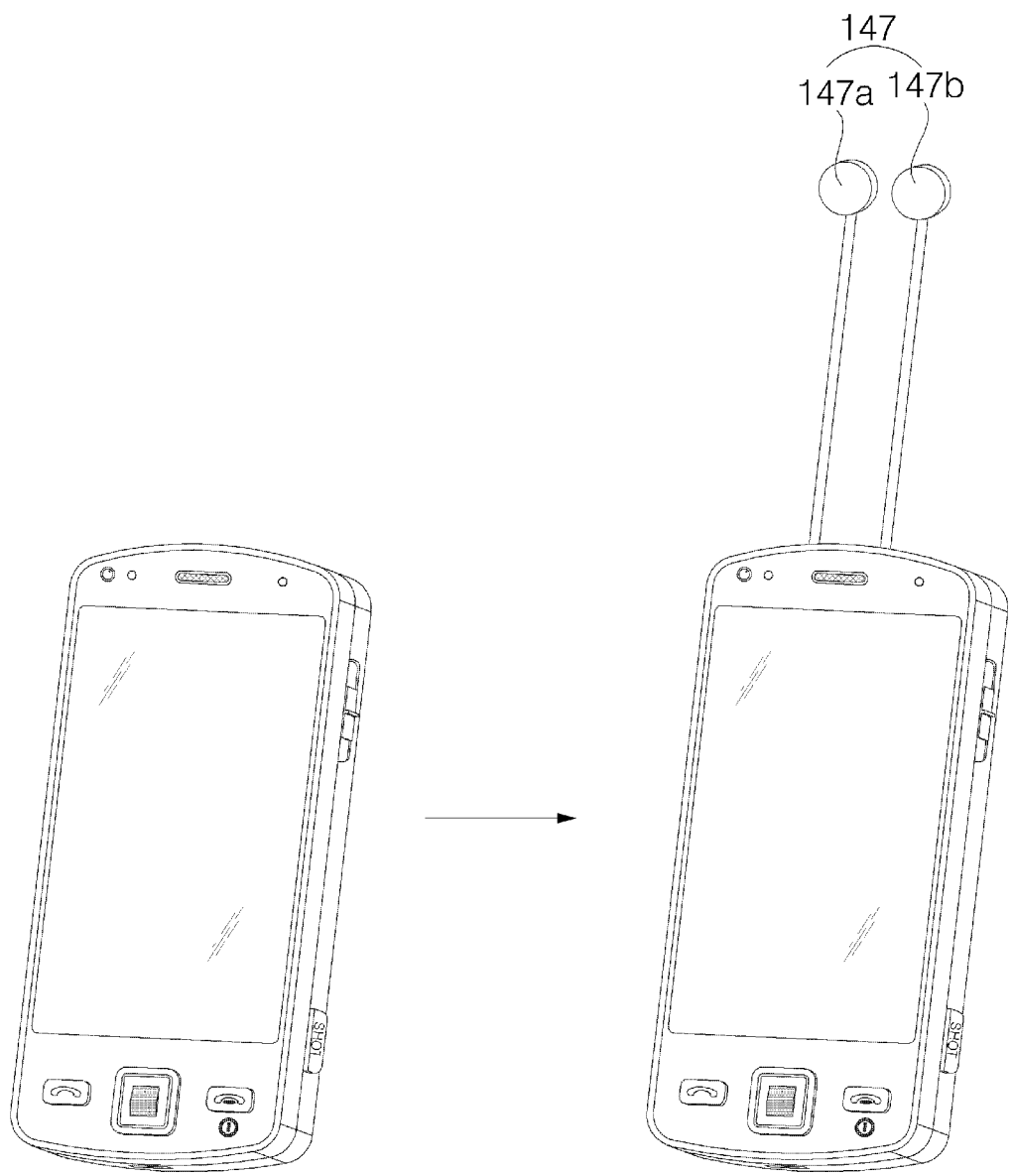
FIG. 6 is a diagram illustrating an example of the arrangement of a brain wave sensor in the mobile terminal shown in FIG. 1.

FIG. 6 illustrates the arrangement of the brain wave sensor 147 in the mobile terminal 100. FIG. 7 illustrates the brain wave sensor 147 in use during a call.

Referring to FIG. 6, the brain wave sensor 147 may be located at a location where it can be placed in contact with a user. More specifically, the brain wave sensor 147 may be retracted and extended from the mobile terminal 100 during the use of the mobile terminal 100.

The brain wave sensor 147 is illustrated in FIG. 6 as having two sensors 147a and 147b, but the present invention is not restricted to this. The brain wave sensor 147 may include more or less than two sensors.

Referring to FIG. 7, the brain waves of a user may be measured by retracting and extending the sensors 147a and 147b of the brain wave sensor 147 from the mobile terminal 100. The sensors 147a and 147b are bent such that they properly attached to the head of the user.

Alternatively, one or more wireless brain wave sensors may be attached to a hair accessory or glasses of the user. In this case, the wireless brain sensor modules may detect the brain waves of the user when worn on the head or the face of the user, process the results of the detection, and transmit multi-channel EEG signals obtained by the processing to the mobile terminal 100 either directly or via another device.

FIG. 8 illustrates a table showing correspondence between brain wave frequency bands and human states of mind. Referring to FIG. 8, brain waves resulting from the electrical activities of neurons in the cerebral cortex are largely classified into delta, theta, alpha, beta and gamma waves. Once the type of brain waves measured from the user is determined through the analysis of the frequency band of the measured brain waves, the state of mind of the user can be determined based on the type of the measured brain waves.

Figure 9:
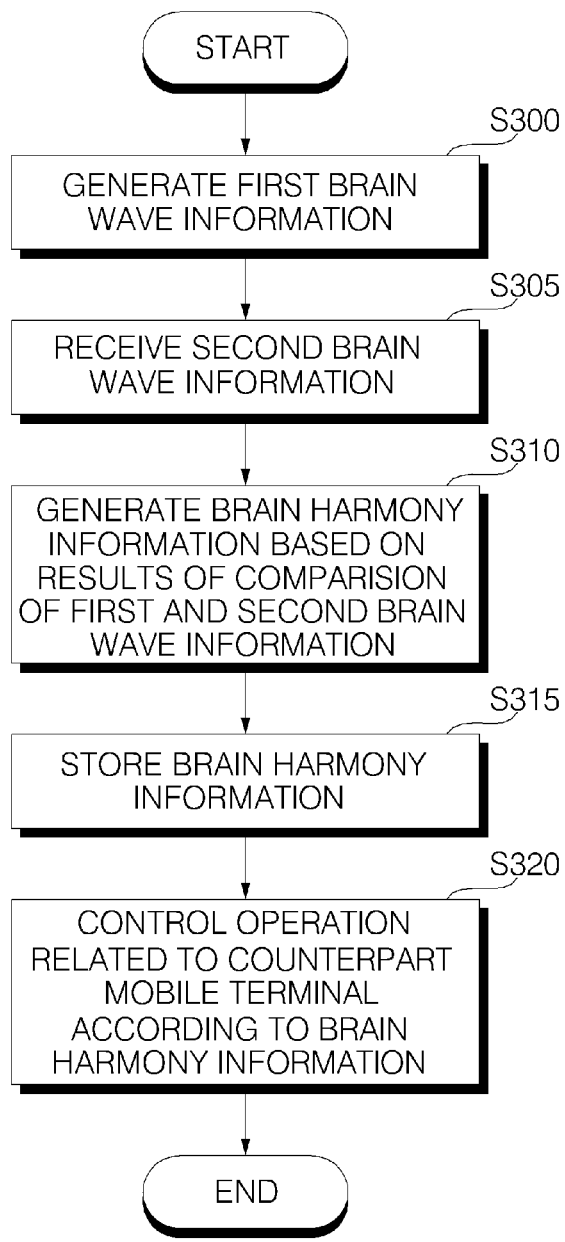
FIG. 9 is a flowchart of a method of controlling the operation of a mobile terminal according to an embodiment of the present invention.
Figure 10:
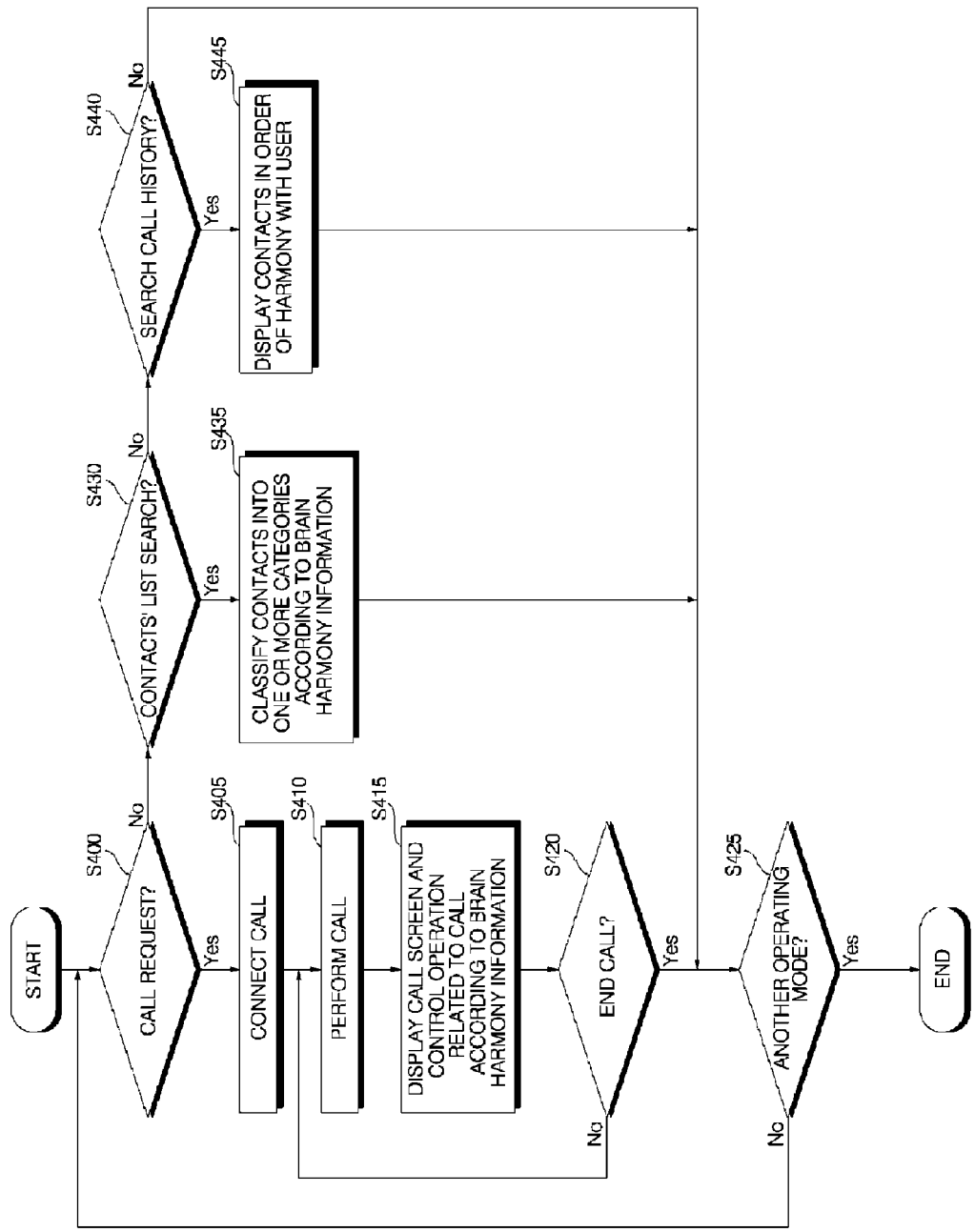
FIG. 10 is a flowchart of a method of controlling the operation of a mobile terminal, according to another embodiment of the present invention.
Figure 11:
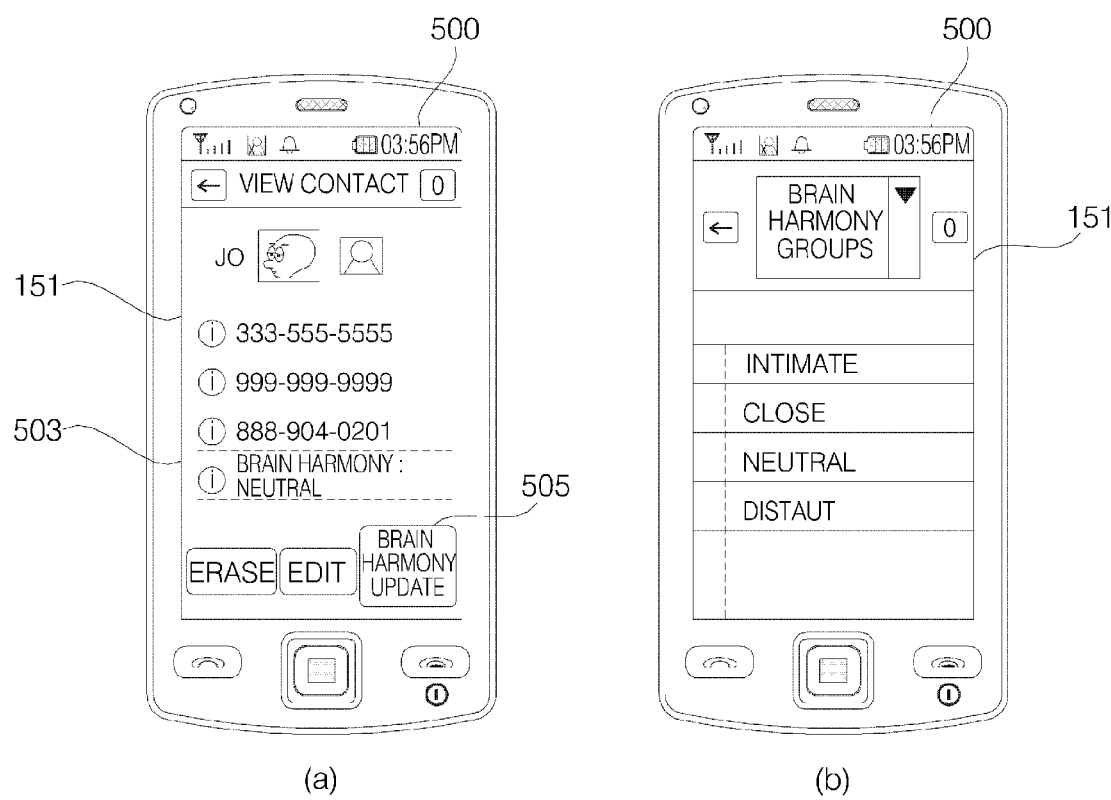
FIGS. 11 through 17 are diagrams illustrating examples of controlling the operation of a counterpart mobile terminal based on brain harmony information.
Figure 12:
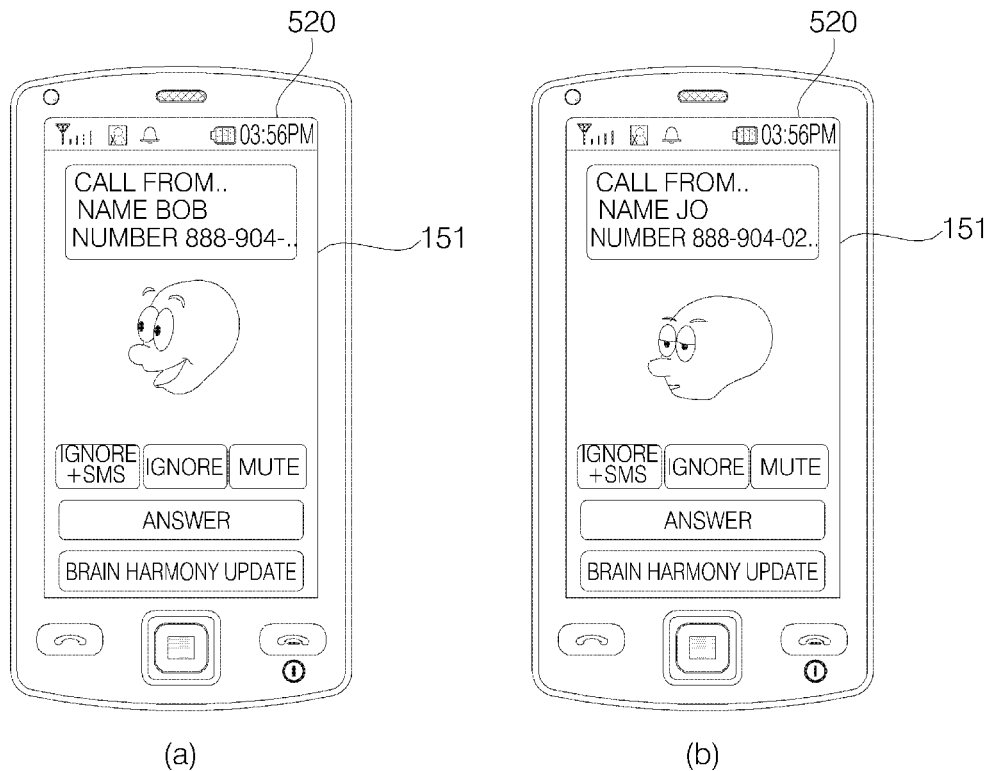

FIGS. 9 and 10 illustrate flowcharts of methods of controlling the operation of a mobile terminal according to an embodiment of the present invention. Referring to FIG. 9, the controller 180 generates first brain wave information of a user of the mobile terminal 100 (S300). Thereafter, the controller 180 receives second brain wave information of a user of a counterpart mobile terminal (S305).

The controller 180 may also transmit the first brain wave information to the counterpart mobile terminal in order to exchange brain wave information with the counterpart mobile terminal. The brain wave information exchanged between the controller 180 and the counterpart mobile terminal may be a brain wave signal that can be transmitted or state-of-mind information corresponding to the brain wave signal. The type of brain wave information exchanged between the controller 180 and the counterpart mobile terminal may vary according to the environment of the use of the mobile terminal 100.

The mobile terminal 100 may exchange brain wave information with the counterpart mobile terminal through short-range communication, such as Bluetooth™ or the Internet, or via a messaging service. More specifically, the controller 180 may encode brain wave information into a vMsg format and transmit the encoded brain wave information to the counterpart mobile terminal using Bluetooth™ Object Push Profile (OPP). The controller 180 may transmit brain wave information to or receive brain wave information from the counterpart mobile terminal using Bluetooth™ File Transfer Profile (FTP).

Alternatively, the controller 180 may encode brain wave information into a format, such as XML, that the mobile terminal 100 and the counterpart mobile terminal both agree on and upload the encoded brain wave information to a predefined website. Then, the counterpart mobile terminal may access the predefined website and download the encoded brain wave information from the predefined website.

Still alternatively, the controller 180 may encode brain wave information into an SMS format and then transmit the encoded brain wave information to the counterpart mobile terminal. Still alternatively, the controller 180 may encode brain wave into a format that the mobile terminal 100 and the counterpart mobile terminal both agree on and transmit the encoded brain wave information to the counterpart mobile terminal as an attachment of an MMS message.

Referring again to FIG. 9, the controller 180 compares the first brain wave information with the second brain wave information, and generates brain harmony information based on the results of the comparison (S310). For example, the controller 180 may compare the first brain wave information with the second brain wave information through cross-correlation, and generate brain harmony information, which indicates how much the first brain wave information harmonizes with the second brain wave information, based on a level of similarity between the first brain wave information and the second brain wave information. The controller 180 may classify the relationship between the users of the mobile terminal 100 and counterpart mobile terminal as an intimate relationship, a close relationship, a neutral relationship, or a distant relationship.

The controller 180 stores the generated brain harmony information in the memory 160 (S315). Then, the controller 180 controls an operation performed by the mobile terminal 100 in connection with the counterpart mobile terminal according to the generated brain harmony information (S320).

Examples of the operation relevant to the counterpart mobile terminal include, but are not limited to, a call between the mobile terminal 100 and the counterpart mobile terminal, messaging between the mobile terminal 100 and the counterpart mobile terminal, short-range-communication between the mobile terminal 100 and the counterpart mobile terminal and transmission of a multimedia stream between the mobile terminal 100 and the counterpart mobile terminal. According to this embodiment, it is possible to effectively control various operations performed by the mobile terminal 100 in connection with the counterpart mobile terminal according to how the state of mind of the user of the mobile terminal 100 harmonizes with the state of mind of the user of the counterpart mobile terminal.

FIG. 10 illustrates a flowchart of a method of controlling the operation of a mobile terminal, according to another embodiment of the present invention. Referring to FIG. 10, when a user enters the phone number of a counterpart mobile terminal and issues a request for calling the entered phone number, for example, by pressing a call icon (S400), the controller 180 controls the wireless communication unit 110 to connect a call to the counterpart mobile terminal (S405) and performs a call operation with the counterpart mobile terminal (S410).

During the call with the counterpart mobile terminal, the controller 180 displays a call screen and controls an operation related to the call with the counterpart mobile terminal according to brain harmony information of the counterpart mobile terminal (S415). For example, the controller 180 may select a call screen or an icon to be displayed or call background music to be played during the call with the counterpart mobile terminal according to the brain harmony information of the counterpart mobile terminal. Operations S410 and S415 may be repeatedly performed until the user chooses to end the call with the counterpart mobile terminal (S420).

If the user chooses to search a contacts' list (S430), the controller 180 classifies the contacts in the contact's list into one or more categories according to their respective brain harmony information (S435). For example, the controller 180 may classify the contacts in the contacts' list into an 'intimate relationship' category, a 'close relationship' category, a 'neutral relationship' category, and a 'distant relationship' category according to their brain harmony information, and may then display the results of the classification of the contacts in the contacts' list on the display module 151.

On the other hand, if the user chooses to search a call history (S440), the controller 180 displays contacts in the call history in order of harmony with the user, in terms of state of mind, according to their respective brain harmony information (S445). Operations S430 through S445 may be repeatedly performed until the user chooses an operating mode other than a current operating mode (S425).

According to this embodiment, it is possible to effectively control an operation relevant to a call with a counterpart mobile terminal or other operations according to brain harmony information of the counterpart mobile terminal. The method illustrated in FIG. 10 will be described in further detail with reference to FIGS. 11 through 17.

Referring to FIG. 11(a), an icon 503 representing brain harmony information of a counterpart mobile terminal may be displayed on a 'contacts' screen 500 of the display module 151. An 'update brain harmony' icon 505 may be provided on the 'contacts' screen 500. When the 'update brain harmony' icon 505 is pressed, the brain harmony information of the counterpart mobile terminal may be updated. Referring to FIG. 11(b), contacts listed on the 'contacts' screen 500 may be classified into one or more categories (e.g., 'intimate,' 'close,' 'neutral,' and 'distant') according to their brain harmony information, and may then be displayed in units of the categories.

Referring to FIGS. 12(a) and 12(b), during a call with a counterpart mobile terminal, an icon representing brain harmony information of the counterpart mobile terminal may be displayed on a call screen 520 of the display module 151. Different call background images or different call background music may be provided for different brain harmony information.

Figure 13:
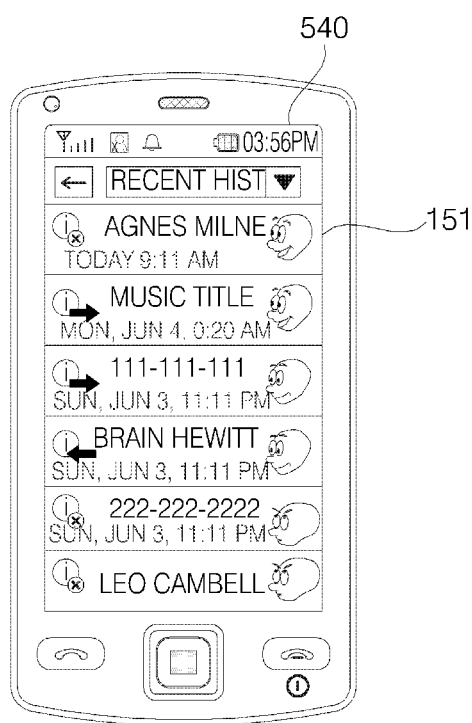
Figure 14:
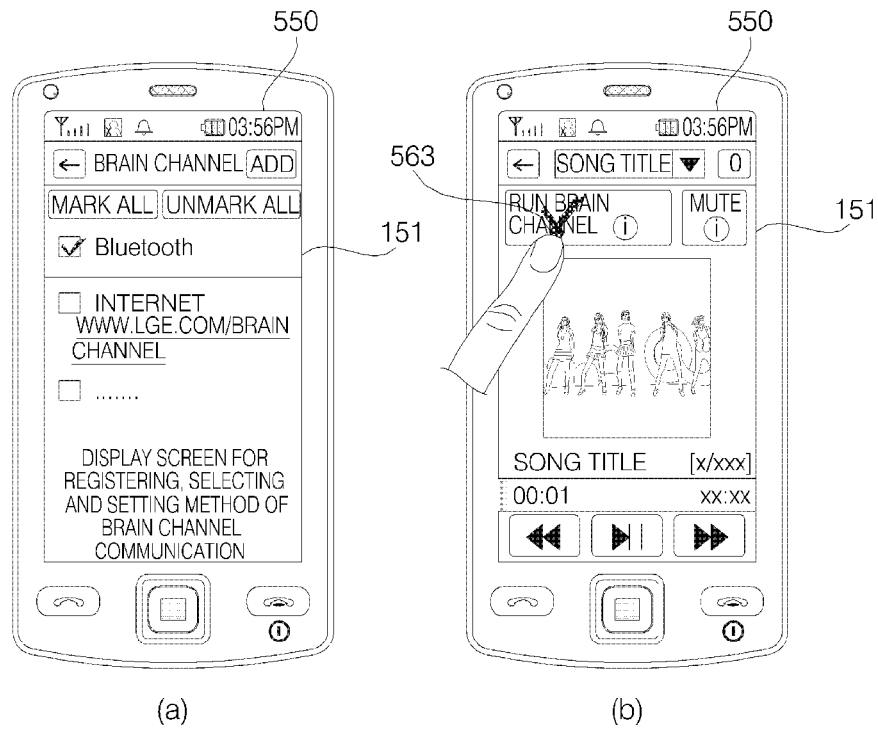

Referring to FIG. 13, when the user requests a call history search, a call history screen 540 may be displayed on the display module 151. Contacts listed on the call history screen 520 may be realigned in order of harmony with the user in terms of state of mind.

FIGS. 14(a) and 14(b) illustrate an example of transmitting a multimedia stream to one or more counterpart mobile terminals according to their brain harmony information. Referring to FIGS. 14(a) and 14(b), if the user selects a method to transmit a multimedia stream on a 'brain channel' screen 550 of the display module 151 and then presses a 'run brain channel' icon 563, the multimedia stream may be selectively transmitted to one or more counterpart mobile terminals according to their brain harmony information using the selected method.

Figure 15:
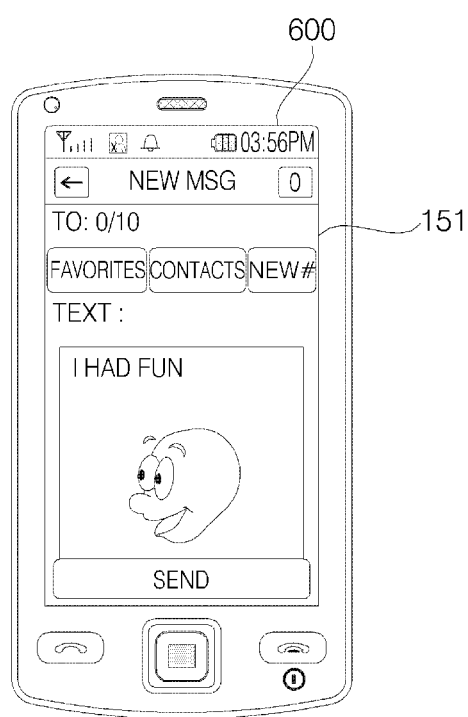
Figure 16:
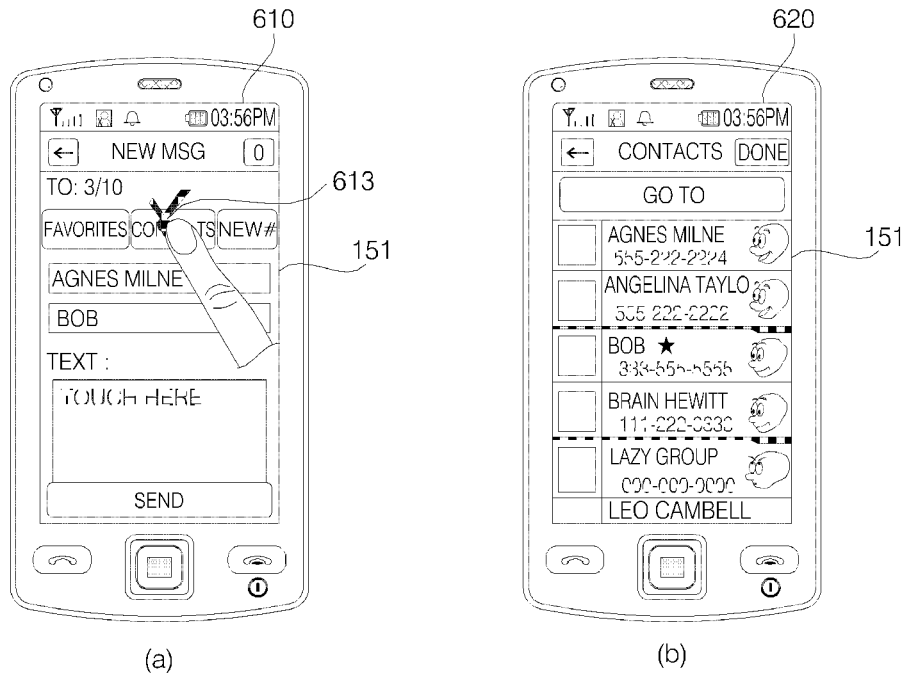

Referring to FIG. 15, a background image on a 'new message' screen 600 of the display module 151 may vary according to brain harmony information of a contact to which the user intends to send an SMS or MMS message or email. In addition, if the user intends to enter a frequently-used word or phrase, a list of frequently-used words or phrases may be displayed. If the brain harmony information of the contact indicates that the contact and the user are in a close relationship with each other, words, phrases or emoticons that represent joy or laughter may come first in the list of frequently-used words or phrases. When an SMS or MMS message or an email is received, the received message or email may be classified into and saved in one of a number of folders present in the memory 160 according to brain harmony information of its sender.

Referring to FIGS. 16(a) and 16(b), if a 'contacts' icon 613 is selected from a 'new message' screen 610 on the display module 151, a 'contacts' screen 620 showing a contacts' list may be displayed. Contacts are arranged in the contacts' list according to brain harmony information.

Figure 17:
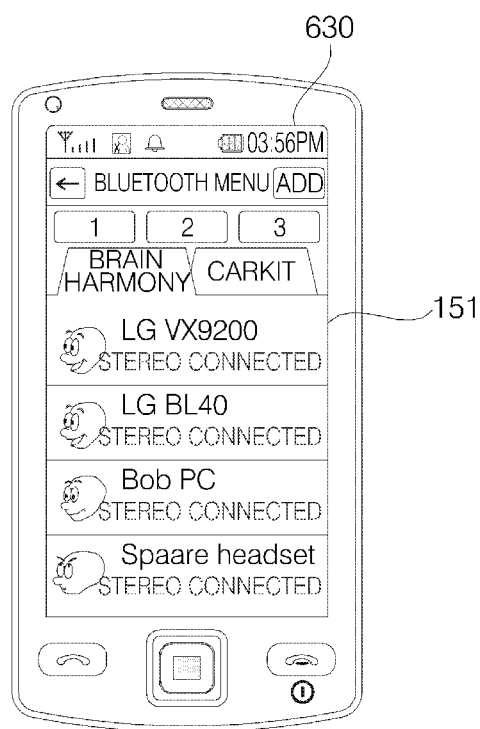

Referring to FIG. 17, a display screen 630 may be displayed on the display module 151 showing a list of devices that can communicate with the mobile terminal 100 through, for example, Bluetooth™. Each of the devices listed on the display screen 630 may be associated with an icon or image representing corresponding brain harmony information. Only some devices that satisfy a particular brain harmony information condition may be selectively displayed on the display screen 630 and these devices may be configured to be connected to or exchange data with the mobile terminal 100 without a requirement of any authorization.

In a Twitter™ or messenger service, only a number of contacts that satisfy a particular brain harmony information condition may be configured to access any updates related to the user. In addition, a list of Twitter™ followers may be aligned according to their brain harmony information.

As illustrated in FIGS. 11 through 17, it is possible to control various operations performed by the mobile terminal according to how much the state of mind of the user of the mobile terminal 100 harmonizes with the state of mind of a user of a counterpart mobile terminal.

The brain wave sensor 147 may be provided in the mobile terminal 100 or in an external device. For convenience, it is assumed that the brain wave sensor 147 is provided inside the mobile terminal 100 and the mobile terminal performs signal processing on brain wave measurements and analyzes the results of the signal processing. However, the brain wave sensor 147 and a module for analyzing brain wave measurements may both be provided in an external device with the controller 180 receiving brain wave data obtained by the analysis of brain wave measurements from the external device and using the received brain wave data without additional analysis.

Figure 18:
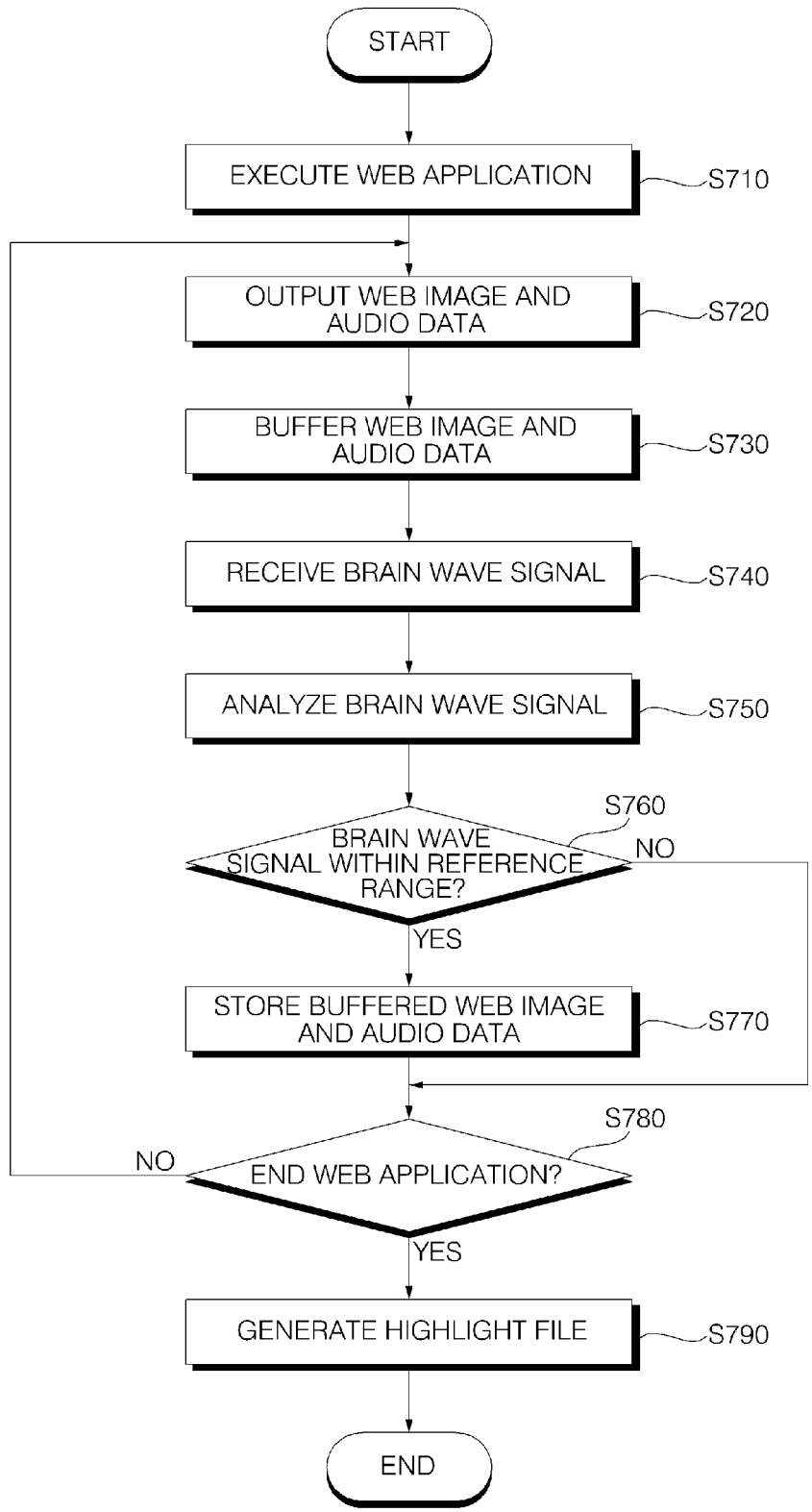
FIG. 18 is a flowchart illustrating a method of generating a highlight file based on a brain wave pattern during the execution of a web application according to an embodiment of the present invention.

FIG. 18 illustrates a flowchart of a method of generating a highlight file based on a brain wave pattern during the execution of a web application according to an embodiment of the present invention. Referring to FIG. 18, the controller 180 executes a web application in response to, for example, a user command (S710). The web application may be an application that is executed through web browsing in order to perform online electronic commerce and auction, an internet bulletin board, a blog or an online game.

A web image relevant to the execution of the web application is displayed on the display module 151 and audio data relevant to the execution of the web application is output via the audio output module 152 (S720). Then, the controller 180 buffers the web image and the audio data for a predefined amount of time (S730).

More specifically, the controller 180 temporarily stores the web image and the audio data for a predefined amount of time and then deletes the web image and the audio data. The buffered web image and the buffered audio data may include a previously-output web image and previously-output audio data in consideration that it may take time for a user to view or listen to and then to respond to a web image or audio data. Thus, the controller 180 may buffer a number of web images and audio data that are output within a predefined amount of time. If there are more than one buffered web image and audio data, the controller 180 deletes the oldest buffered web image and audio data. Buffered web images may be associated with their respective audio data according to their output times.

The controller 180 receives a signal requesting the user's brain waves detected by the brain wave sensor 147 (S740). Thereafter, the controller 180 analyzes the received brain wave signal by performing signal processing on the received brain wave signal (S750).

More specifically, the controller 180 may receive an electric signal from the brain wave sensor 147, amplify the received electric signal, remove spurious components from the amplified electric signal, and convert the resulting electric signal into a digital signal. Thereafter, the controller 180 may Fourier-transform the digital signal and analyze the user's brain waves based on the Fourier-transformed digital signal.

The controller 180 then determines, based on the results of the brain wave signal analysis, whether the level of a brain wave of the user classified into a predefined frequency band falls within a reference range (S760). The reference range may be a range that the brain waves of the user can reach when the user is in a predefined state of mind such as the state of excitement, relaxation, or concentration. The user may have different brain wave patterns for different states of mind. Information on the reference range is stored in advance in the memory 160, and the controller 180 determines, based on the information present in the memory 160, whether the user is in the predefined state of mind according to whether the level of the brain wave classified into the predefined frequency band falls within the reference range.

If the level of the brain wave classified into the predefined frequency band falls within the reference range, the controller 180 stores the buffered web image and audio data (S770). The buffered web image may be stored in an image format.

The operation of outputting the web image and audio data (S720) through storing the buffered web image and audio data (S770) may be repeatedly performed until the execution of the web application is ended (S780). As a result, the controller 180 may store web images and audio data displayed and played during a period of time when the level of the brain wave classified into the predefined frequency band stays within the reference range.

When the execution of the web application is ended (S780), the controller 180 combines the stored web image and audio data and generates a single highlight file (S790). Then, the controller 180 stores the highlight file in a highlight folder in the memory 160.

In the embodiment illustrated in FIG. 18, buffered web image and audio data are stored in the memory 160 instead of a web image and audio data currently being output. However, the present invention is not restricted to this. A web image and audio data output during a period of time when the level of the brain wave classified into the predefined frequency band stays within the reference range may be stored in the memory 160 without buffering.

Alternatively, if the level of the brain wave classified into the predefined frequency band falls within the reference range, video and audio data may continue to be stored until the execution of the web application is ended. On the other hand, the entire video and audio data relevant to the execution of the web application may be stored throughout the execution of the web application.

During the execution of the web application, no audio data may be output. In this case, the controller 180 may generate a highlight file using web images only.

The controller 180 may determine in real time whether the level of the brain wave classified into the predefined frequency band falls within the reference range regardless of a change of a web image. Alternatively, the controller 180 may determine whether the level of the brain wave classified into the predefined frequency band falls within the reference range only upon a change of a web image, thereby reducing the power consumption of the mobile terminal 100.

During the execution of a broadcast program viewer application, a highlight file may also be generated using the same method used to generate a highlight file during the execution of a web application. A broadcast program viewer application is an application for receiving at least a broadcast signal or broadcast-related information from an external broadcast management server via a broadcast channel and providing the received signal or information.

During the execution of a player application a highlight file may also be generated using the same method used to generate a highlight file during the execution of a web application. A player application is an application for playing content present in the memory 160.

However, since the player application is simply for playing content previously stored in the memory 160, a highlight file may be generated based on address information of the content instead of simply the content. This will be described in further detail with reference to FIG. 19.

Figure 19:
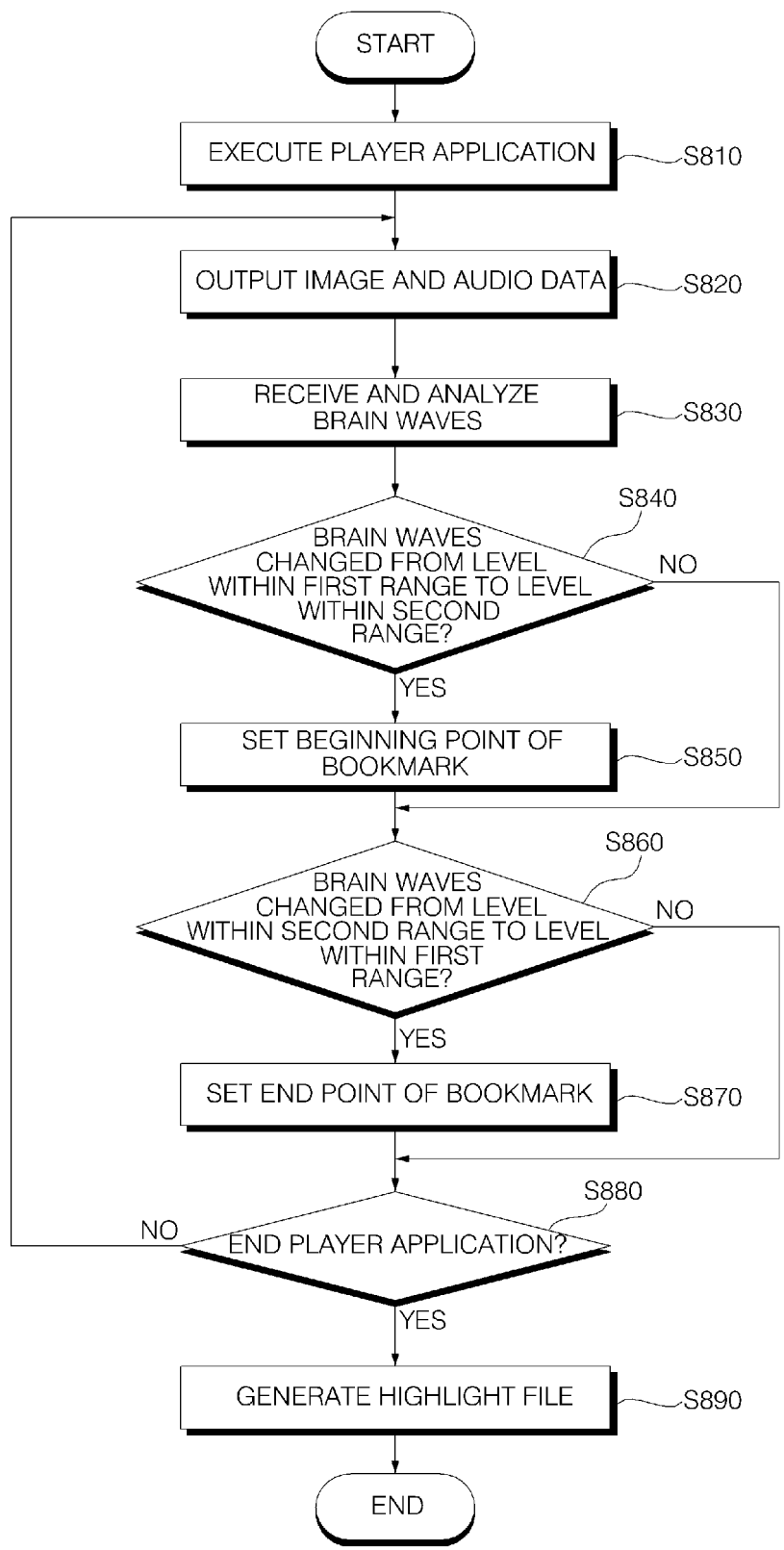
FIG. 19 is a flowchart illustrating a method of setting a bookmark based on a brain wave pattern during the execution of a multimedia player application according to an embodiment of the present invention.

FIG. 19 illustrates a flowchart of a method of setting a bookmark according to a brain wave pattern during the execution of a player application according to an embodiment of the present invention. Referring to FIG. 19, the controller 180 executes a player application (S810). Then, the controller 180 displays an image relevant to the execution of the player application on the display module 151 and outputs audio data relevant to the execution of the player application via the audio output module 152 (S820).

Thereafter, the controller 180 analyzes a user's brain waves detected by the brain wave sensor 147 (S830). If the results of the brain waves analysis indicate that the level of a brain wave of the user classified into a predefined frequency band falls within a reference range, the controller 180 may set a bookmark in content currently played.

More specifically, the controller 180 determines whether the brain wave classified into the predefined frequency band has changed from a level within a first range that outside the reference range to a level within a second range that is within the reference range (S840). If it is determined that the brain wave classified into the predefined frequency band has changed from a level within the first range to a level within the second range, the controller 180 sets content currently being played as the beginning point of a bookmark and stores address information of the current content (S850). On the other hand, if it is determined that the brain wave classified into the predefined frequency band has changed from a level within the second range to a level within the first range, the controller 180 sets the current content as the end point of a bookmark and thus stores address information of the current content (S870).

Alternatively, the controller 180 may set content previous to the current content as the beginning point of a bookmark in consideration that it generally takes time for the user to respond. In this case, the previous content may be modified in consideration of playback speed and the time taken for the user to respond. For example, content address information set as the beginning point of a bookmark when playback speed is high may be earlier than content address information set as the beginning point of a book mark when playback speed is low.

The controller 180 can set a bookmark in video or audio data played when the brain wave classified into the predefined frequency band falls within the reference range by repeatedly performing the operations for outputting the image and audio data (S820) through setting the output of the bookmark (S870).

When the execution of the player application ends (S880), the controller 180 generates a highlight file based on address information of content and stores the highlight file in connection with a file including the content (S890).

If the end point of a bookmark is designated but the beginning point of the bookmark is yet to be designated, the controller 180 may set address information of first content in a file to be played as the beginning point of the bookmark. On the other hand, if the beginning point of a bookmark is designated but the end point of the bookmark is yet to be designated, the controller 180 may set address information of last content in a file to be played as the end point of the bookmark. In this manner, the controller 180 may set a bookmark section.

According to the method illustrated in FIG. 19, it is possible to make efficient use of the storage space of the memory 160 since a highlight file is generated using only address information of content played when the brain wave classified into the predefined frequency band falls within the reference range.

A player application may be classified into a video player application, an image viewer application, or an audio player application. During the execution of an image viewer application, the controller 180 may set a bookmark in each still image instead of setting the beginning and end points of a bookmark.

Figure 20:
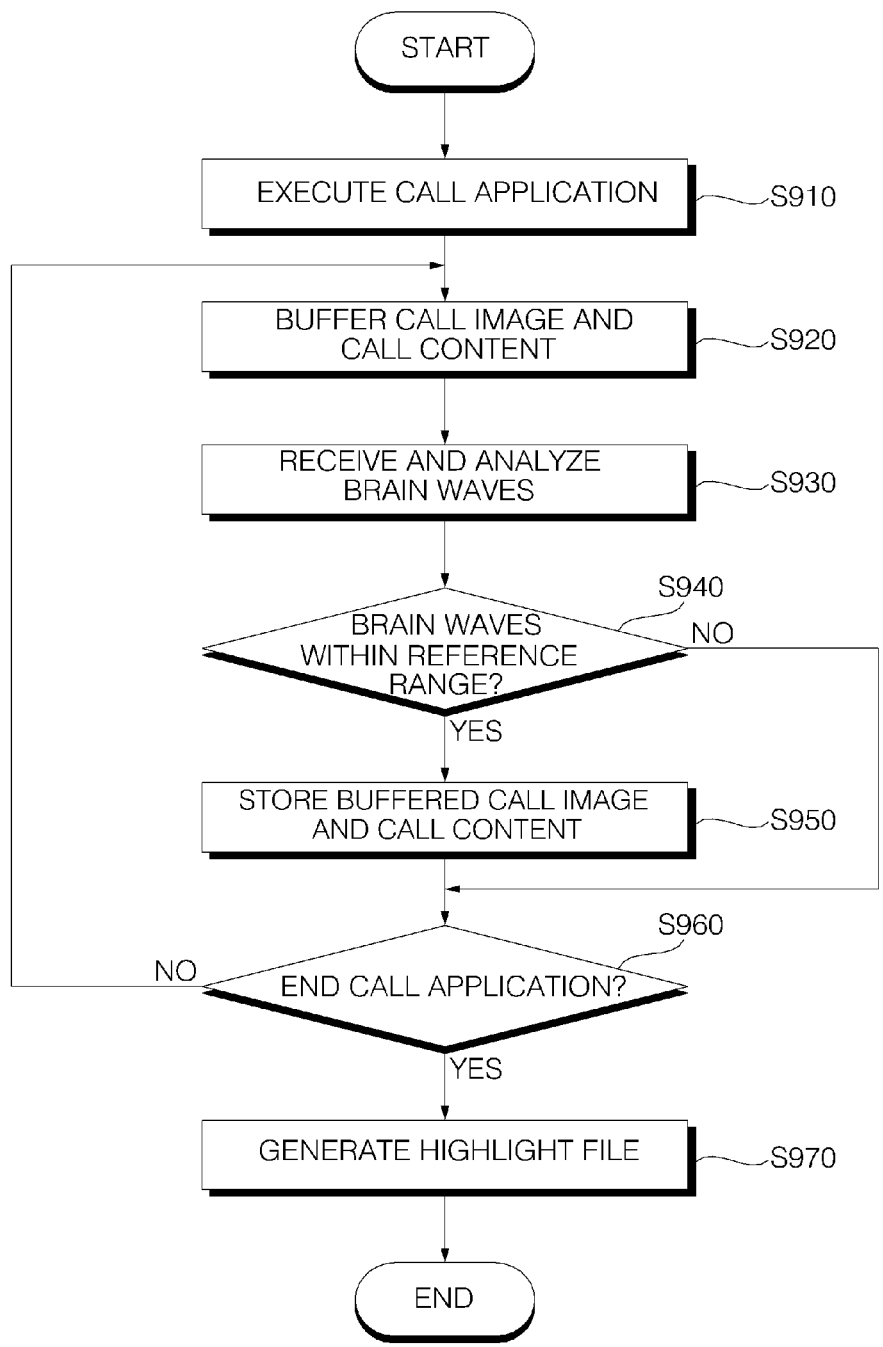
FIG. 20 is a flowchart illustrating a method of generating a highlight file based on a brain wave pattern during the execution of a call application according to an embodiment of the present invention.

FIG. 20 illustrates a flowchart of a method of generating a highlight file according to a brain wave pattern during the execution of a call application according to an embodiment of the present invention. Referring to FIG. 20, the controller 180 executes a call application (S910). Then, the controller 180 buffers a call image and call content relevant to the execution of the call application for a predefined amount of time (S920).

The call content includes at least a call signal generated by the mobile terminal 100 upon the execution of the call application, voice data received from a counterpart mobile terminal or a user's voice data input to the mobile terminal 100 via the microphone 122. When buffering the call image and the call content, the controller 180 may match the call image and the call content with each other with reference to their time information.

The controller 180 receives and analyzes a user's brain waves detected by the brain wave sensor 147 (S930). The controller 180 then determines the level of a brain wave of the user classified into a predefined frequency band falls within a reference range (S940).

If the level falls within the reference range, the controller 180 stores the buffered call image and call content (S950). For example, the controller 180 may store the call image in an image format. The controller 180 may store a number of call images and their respective call content by repeatedly performing operations of buffering the call image and call content (S920) through storing the buffered call image and call content (S950).

When the execution of the call application is ended (S960), the controller 180 generates a highlight file based on the buffered call image and the call content previously stored (S970). If more than one call image and more than one call content are stored, the controller 180 may combine the call images and their respective call content according to time in order to generate a single highlight file.

A call application may be classified into a voice call application or a video call application according to whether it can provide not only the voice of a user of a counterpart mobile terminal but also an image of the user of the counterpart mobile terminal. During the execution of a voice call application, the controller 180 may buffer call content only, and generate a highlight file including the buffered call content, information on the counterpart mobile terminal, and call duration information for each call between the mobile terminal 100 and the counterpart mobile terminal.

In the embodiment illustrated in FIG. 20, a highlight file is generated using a brain wave pattern. However, the present invention is not restricted to this.

Figure 21:
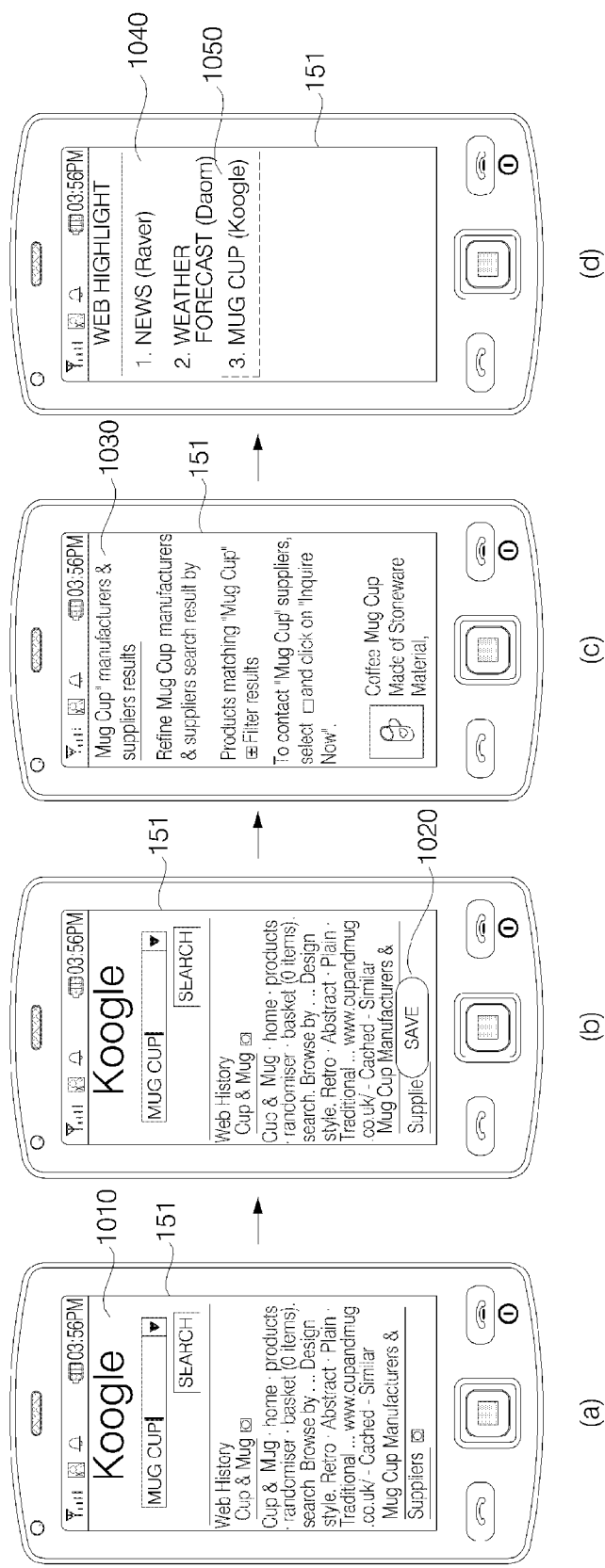
FIG. 21 is a diagram illustrating an example of generating a highlight file based on a brain wave pattern during the execution of a web application.

FIG. 21 illustrates an example of generating a highlight file according to a brain wave pattern during the execution of a web application. Referring to FIG. 21(*a*), when a web application is executed, a first web image 1010 is displayed on the display module 151. The controller 180 buffers the first web image 1010 for a predefined amount of time. If the level of a brain wave of a user classified into a predefined frequency band falls within a reference range, the controller 180 stores the first web image 1010 so that the first web image can be included in a generated highlight file.

Thereafter, referring to FIG. 21(*b*), the controller 180 displays a first indicator 1020 on the display module 151 indicating that the first web image 1010 has been stored. Referring to FIG. 21(*c*), the controller 180 may display a second web image 1030 on the display module 151 in response to, for example, a user command.

The controller 180 determines whether the level of the brain wave classified into a predefined frequency band falls within a reference range. If the level of the brain wave classified into the predefined frequency band falls within the reference range, the controller 180 does not store the second web image 1030.

When the web application is ended, the controller 180 generates a web highlight file based on a number of web images stored. For example, the controller 180 may combine the web images into a single highlight file under a single title. Alternatively, if the web images have different URL information, the controller 180 may generate different sub-web highlight files for the different URL information and then generate a single web highlight file based on the different sub-web highlight files. The title of a web highlight file may include one or more keywords obtained from web images included in the web highlight file or URL information of the web images included in the web highlight file.

Referring to FIG. 21(*d*), if the user selects a web highlight menu, a title 1050 representing the first web image 1010 is displayed on a web highlight menu screen 1040. The title 1050 may include a keyword or URL information of the first web image 1010. When the title 1050 is selected, the first web image 1010 may be displayed again on the display module 151, as shown in FIG. 21(*a*).

Figure 22:
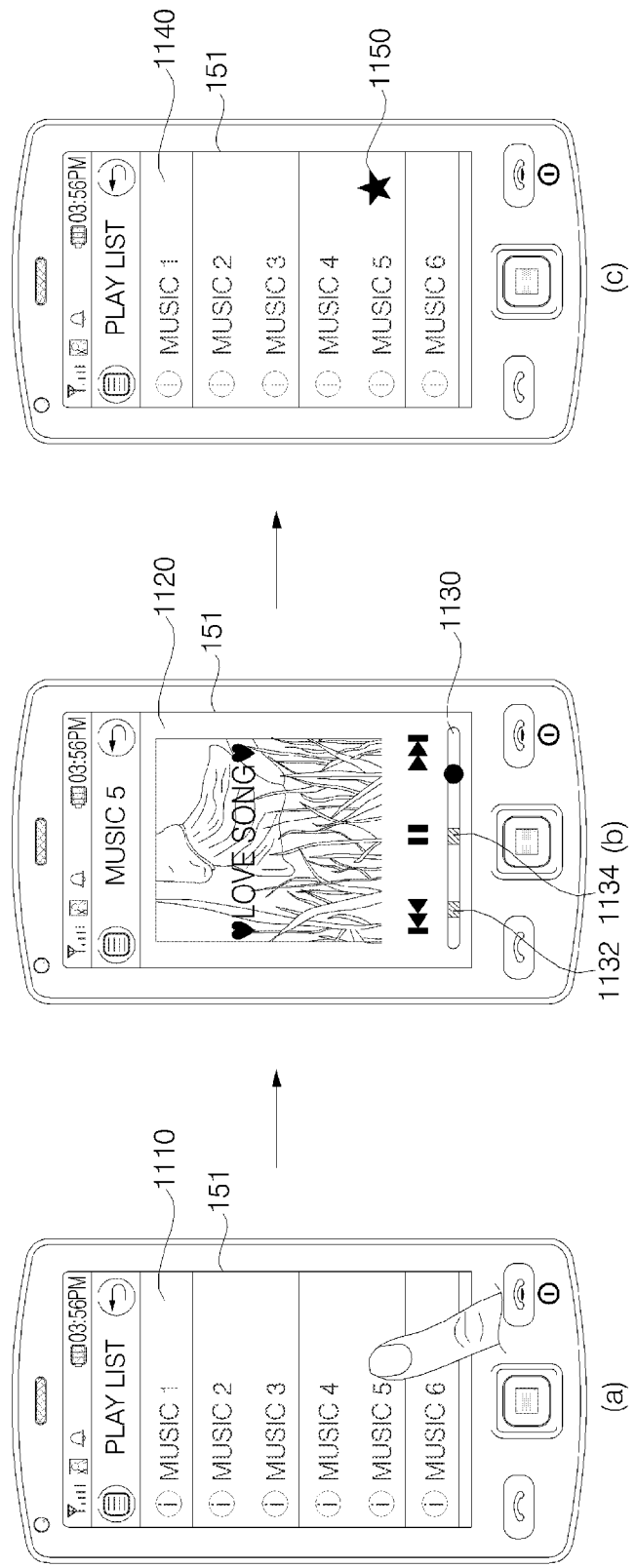
FIG. 22 is a diagram illustrating an example of generating a highlight file based on a brain wave pattern during the execution of an audio player application.

FIG. 22 illustrates an example of generating a highlight file according to a brain wave pattern during the execution of an audio player application. Referring to FIG. 22(*a*), the controller 180 displays a menu screen 1110 including a list of music albums on the display module 151. A user may enter a command to play back a music album by touching to select one of the titles of the music albums listed on the menu screen 1110. In response, a music album corresponding to the selected title may be played back. During the playback of the music album, the controller 180 sets a bookmark in the music album if the level of a brain wave of the user, detected by the brain wave sensor 147 and classified into a predefined frequency band, falls within a reference range.

Referring to FIG. 22(*b*), a progress bar 1130 showing the progress of the playback of the music album is displayed on a music player screen 1120. The progress bar 1130 may also show the state of setting a bookmark in the music album, as indicated by reference numerals 1132 and 1134.

If the user ends the playback of the music album and enters a command to return to the menu screen 1110, the controller 180 displays the menu screen 1110 back on the display module 151, as shown in FIG. 22(*c*). The controller 180 displays a second indicator 1150 next to a music album in which a bookmark is set. If the user touches the second indicator 1150, the controller 180 plays back only the music album in which the bookmark is set instead of playing back all the music albums listed on the menu screen 1110.

Figure 23:
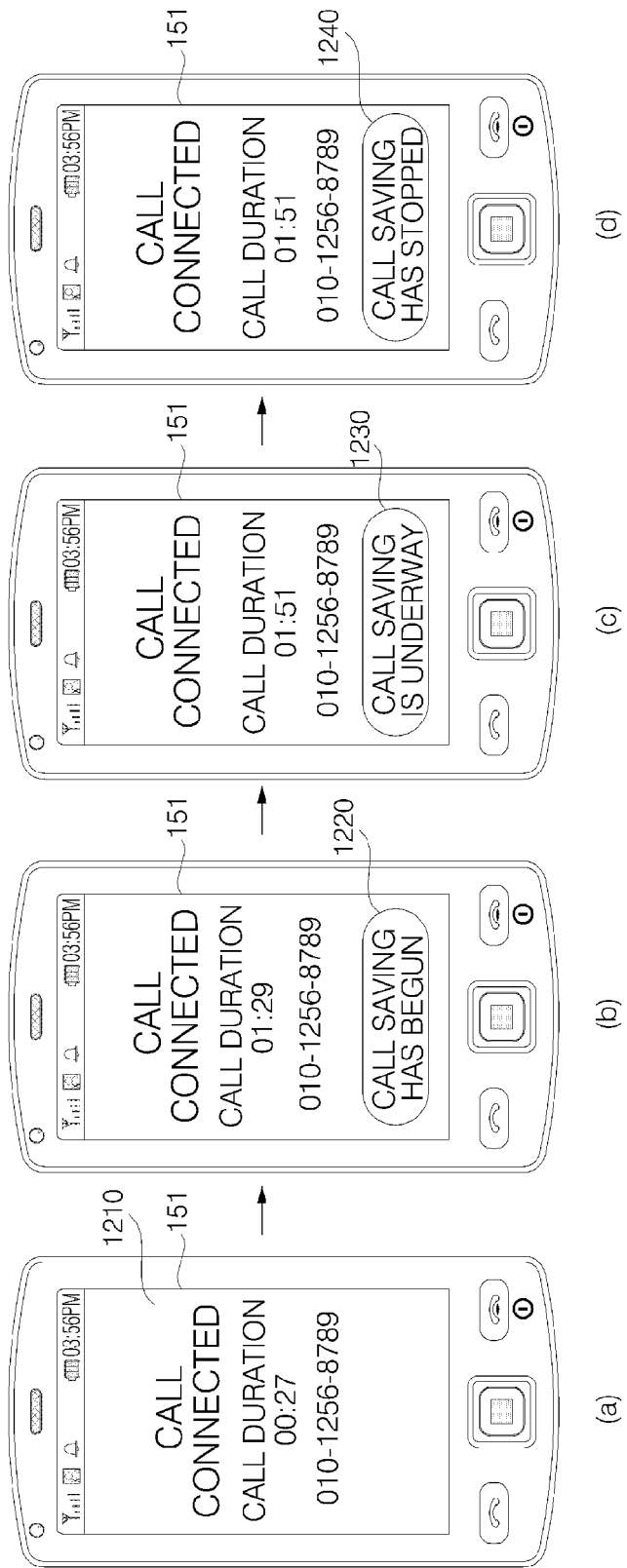
FIG. 23 is a diagram illustrating an example of generating a highlight file based on a brain wave pattern during the execution of a call application.

FIG. 23 illustrates an example of generating a highlight file according to a brain wave pattern during the execution of a call application. Referring to FIG. 23(*a*), when a call application is executed, a display screen 1210 relevant to the execution of the call application is displayed on the display module 151. Then, the controller 180 analyzes a user's brain wave detected by the brain wave sensor 147 and determines whether the level of the user's brain wave falls within a reference range.

If the user's brain wave has just changed from a level outside the reference range to a level within the reference range, the controller 180 begins to store call content, and displays a third indicator 1220 indicating that the storing of call content has begun as illustrated in FIG. 23(*b*). If the level of the user's brain wave continues to stay within the reference range, the controller 180 displays a fourth indicator 1230 indicating that the storing of call content still continues as illustrated in FIG. 23(*c*). Then, when the level of the user's brain wave falls outside the reference range, the controller 180 displays a fifth indicator 1240 indicating that the storing of call content has ended as illustrated in FIG. 23(*d*). In this way, the user can easily identify the operating state of the mobile terminal 100 based on the third, fourth, and fifth indicators 1220, 1230, and 1240.

Figure 24:
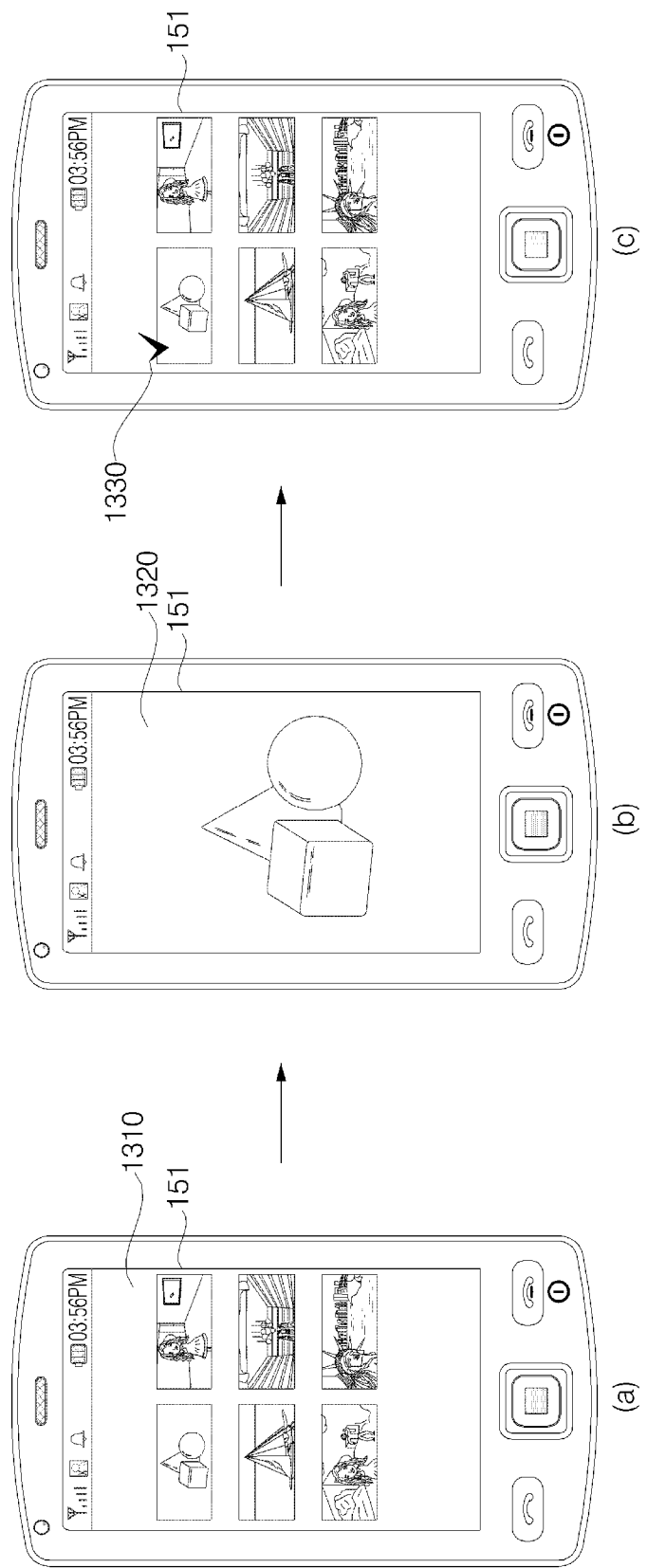
FIG. 24 is a diagram illustrating an example of generating a highlight file based on a brain wave pattern during the execution of an image viewer application.

FIG. 24 illustrates an example of generating a highlight file according to a brain wave pattern during the execution of an image viewer application. Referring to FIG. 24(*a*), when an image viewer application is executed, the controller 180 displays a menu screen 1310 showing a plurality of thumbnails respectively corresponding to a plurality of still images on the display module 151.

If user enters a command to view a still image by touching to select one of the thumbnails, a still image 1320 corresponding to the selected thumbnail may be displayed on the display module 151, as shown in FIG. 24(*b*). During the display of the still image 1320, the controller 180 sets a bookmark in the still image if the level of the brain wave classified into a predefined frequency band falls within a reference range. Then, if the user enters a command to return to the menu screen 1310, the controller 180 again displays the menu screen 1310 on the display module 151 and displays a sixth indicator 1330 on the thumbnail corresponding to the still image 1320 to indicate that a bookmark has been set in the still image, as shown in FIG. 24(*c*).

The reference range may vary according to the user's state of mind. The controller 180 may vary the shape of the sixth indicator 1330 or an indicator indicating whether a highlight file has been generated accordingly.

Figure 25:
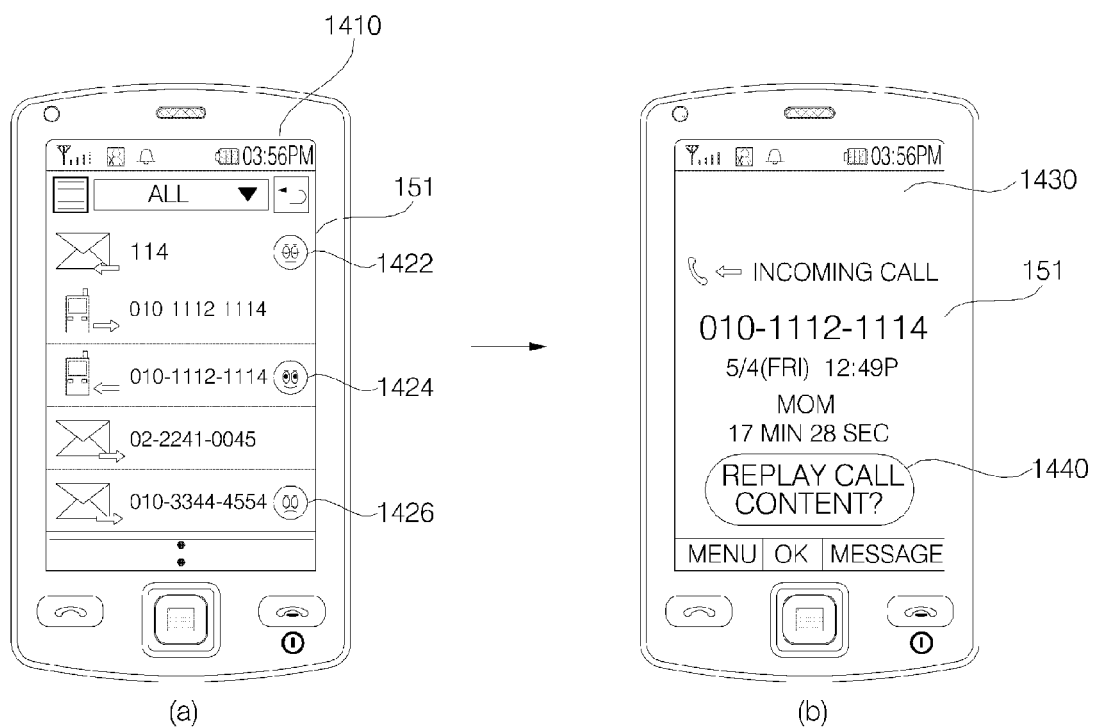
FIG. 25 is a diagram illustrating an example of displaying different indicators for different states of mind.

FIG. 25 illustrates an example of displaying different shapes of indicators according to a user's state of mind. Referring to FIG. 25(*a*), a list of calls is displayed on a call history screen 1410 on the display module 151. A plurality of indicators 1422, 1424, and 1426 indicating that the content of their respective call has been stored are also displayed on the call history screen 1410.

The indicators 1422, 1424, and 1426 may provide information on the user's state of mind at the time when their respective call was made or received. More specifically, the indicators 1422, 1424, and 1426 may be displayed to indicate different states of mind. In this way, the user can easily identify whether the content of a particular call has been stored and his or her state of mind at the time when the particular call was made or received.

The user may enter a command to display detailed call information simply by touching to select one of the calls listed on the call history screen 1410. Then, a detailed call information screen 1430 may be displayed as shown in FIG. 25(*b*). An indicator 1440 indicating that the content of the selected call can be replayed may be displayed on the detailed call information screen 1430. In this manner, it is possible to store the results of the execution of an application in connection with the user's state of mind and provide statistical data on the user's state of mind in the past during the execution of a particular application.

Figure 26:
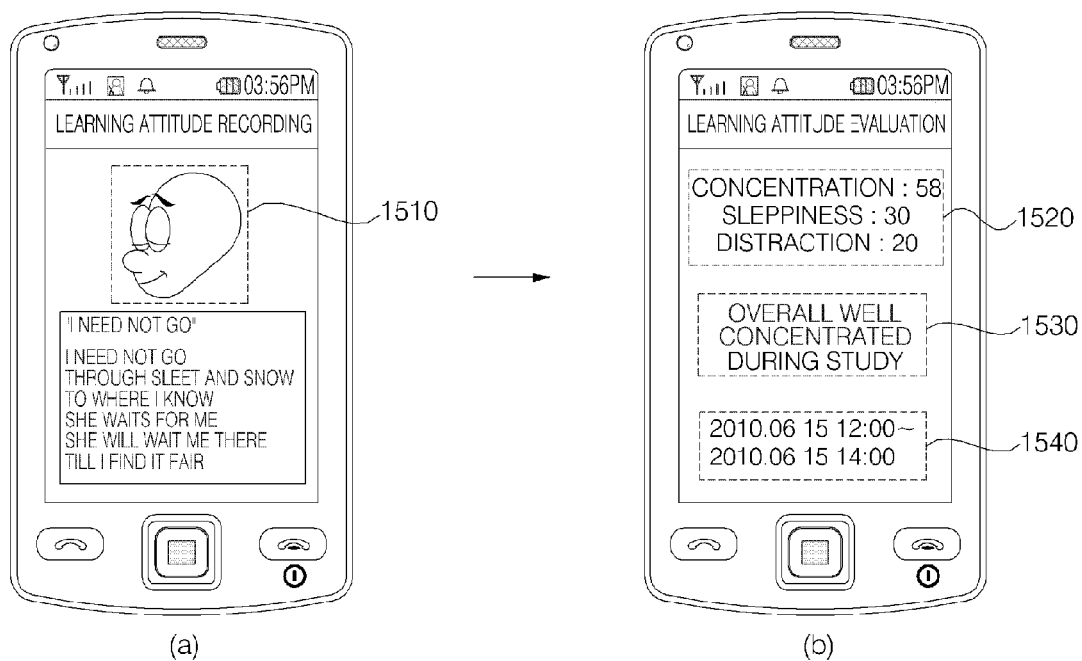
FIG. 26 is a diagram illustrating an example of providing information on a user's learning attitude based on the user's brain waves detected during the execution of an application for learning.

FIG. 26 illustrates an example of providing information on a user's learning attitude based on the user's brain waves detected during the execution of an application for learning. During the execution of an application for learning, the controller 180 analyzes a user's brain waves detected by the brain wave sensor 147. The controller 180 then determines, based on the results of the analysis, whether the pattern of the user's brain waves corresponds to, for example, one of the following three learning attitudes: concentrated, distracted and sleepy.

Brain wave frequency band information on each of the three learning attitudes may be stored in advance in the memory 160. The controller 180 determines the user's learning attitude based on the user's brain waves and the brain wave frequency band information present in the memory 160 and displays an indicator 1510 representing the user's learning attitude on the display module 151, as shown in FIG. 26(*a*).

When the application for learning ends, the controller 180 displays at least information 1520 on the user's scores in view of the three learning attitudes, information 1530 on the user's general learning attitude, or information 1540 on the amount of time the user has spent on the application for learning. In this way, the user can objectively evaluate his or her own learning attitude with respect to the application for learning. Information on the user's learning attitude with respect to the application for learning may be transmitted to an external device and be used as data for the management of learning.

Figure 27:
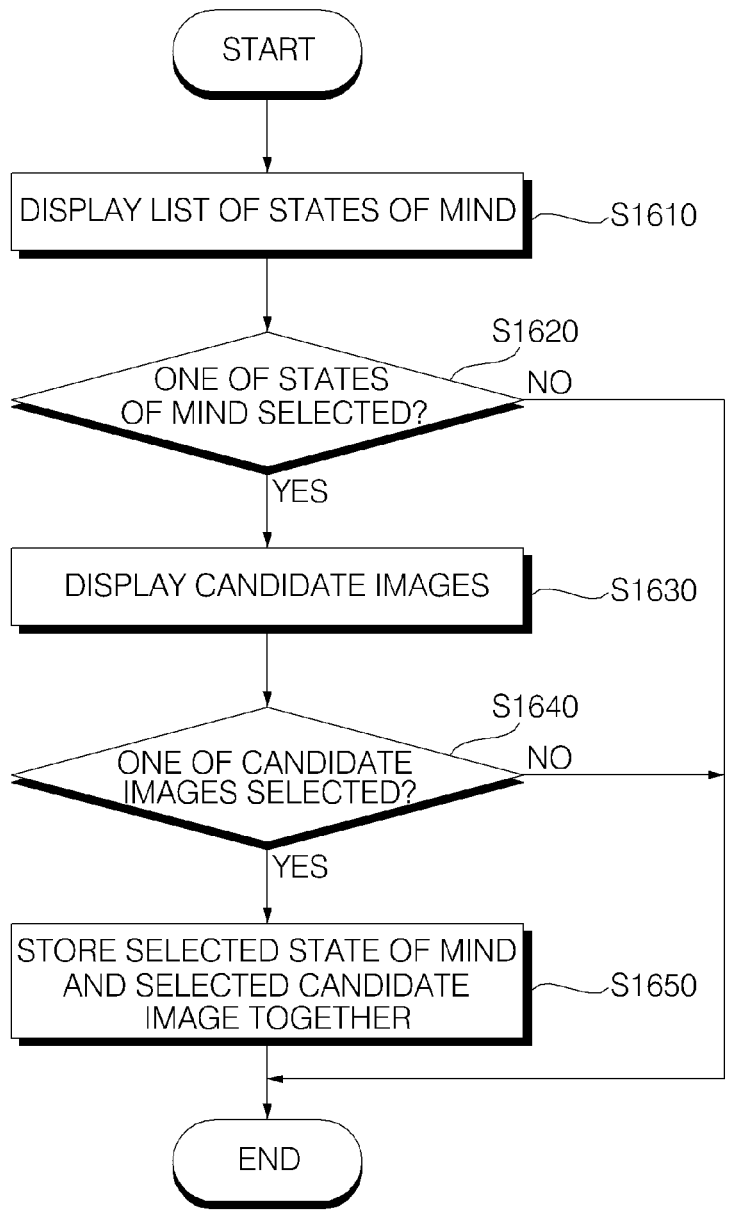
FIG. 27 is a flowchart illustrating a method of registering image data corresponding the state of mind of a user according to an embodiment of the present invention.

FIG. 27 illustrates a flowchart of a method of registering image data corresponding to a user's state of mind according to an embodiment of the present invention. Referring to FIG. 27, the controller 180 displays a display screen showing a list of human states of mind on the display module 151 (S1610). The list may include a variety of states of mind that a user can have, such as excitement, relaxation, distraction, happiness, and sorrow.

A mentality database may store the variety of states of mind and their respective reference brain wave patterns together. Alternatively, the mentality database may include the variety of states of mind and their respective image data, audio data, and/or haptic data together.

If a user command for selecting one of the states of mind included in the list is received (S1620), the controller 180 displays a number of image data candidates that can be stored together with the state of mind selected by the user on the display module 151 (S1630). The image data candidates may be images previously stored in the memory 160, preview images captured by the camera 121, or images representing the user's current brain wave pattern. Thereafter, if a user command for selecting one of the image data candidates is received (S1640), the controller 180 stores the image data candidate selected by the user in the mentality database together with the state of mind selected by the user (S1650).

In this embodiment, a state of mind and an image are stored together in the mentality database. However, the present invention is not restricted to this.

A state of mind and audio data or haptic data may be stored together in the mentality database. In this case, the controller 180 may provide an audio data candidate and a haptic data candidate to the user and may allow the user to choose one of the audio and haptic data candidates.

The mobile terminal 100 may generate image data corresponding to a brain wave pattern. This will be described in detail with reference to FIG. 28.

Figure 28:
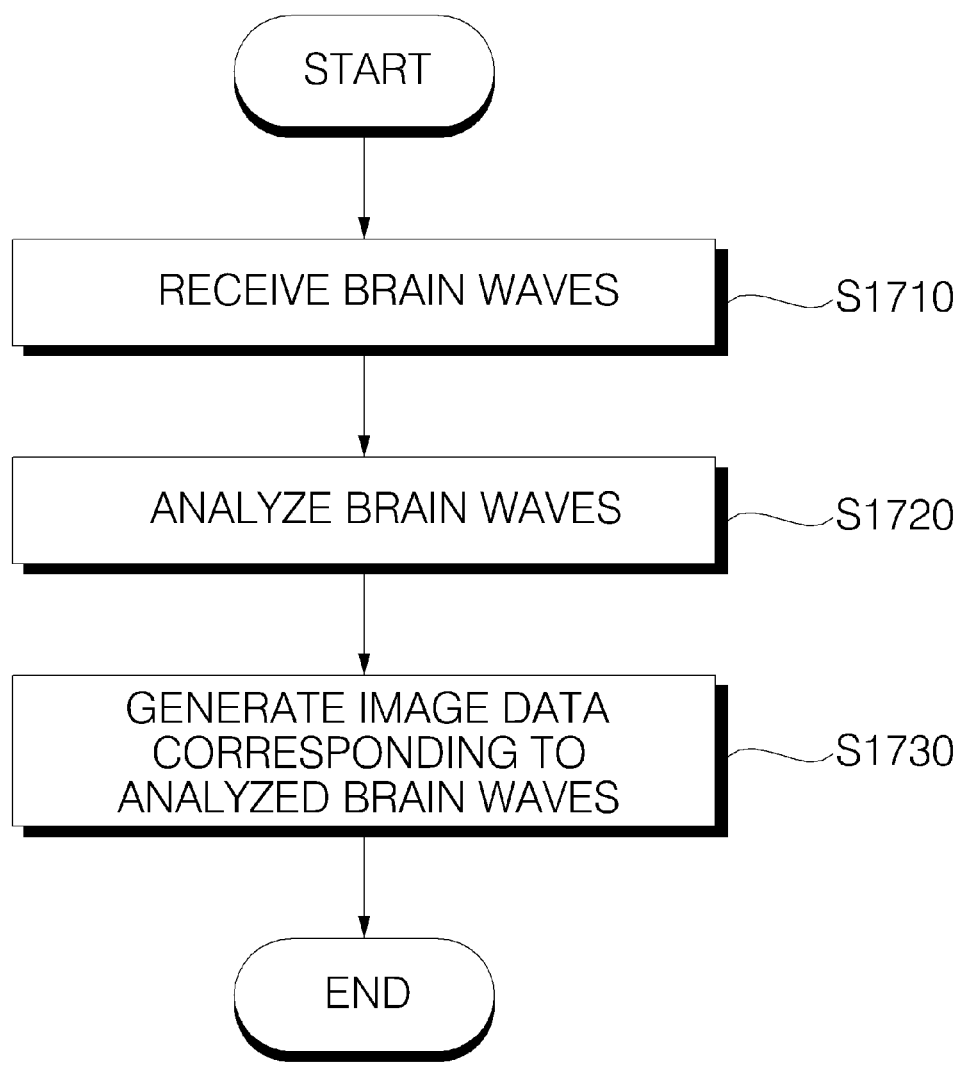
FIG. 28 is a flowchart illustrating a method of generating image data corresponding to a brain wave pattern according to an embodiment of the present invention.

FIG. 28 illustrates a flowchart of a method of generating image data corresponding to a brain wave pattern according to an embodiment of the present invention. Referring to FIG. 28, the controller 180 receives brain waves detected by the brain wave sensor 147 (S1710). The controller 180 analyzes the received brain waves by performing signal processing on the received brain waves (S1720).

More specifically, the controller 180 may receive an electric signal from the brain wave sensor 147, amplify the received electric signal, remove spurious components from the amplified electric signal, and convert the resulting electric signal into a digital signal. The controller 180 may then Fourier-transform the digital signal and analyze a user's brain wave pattern based on the Fourier-transformed digital signal.

Thereafter, the controller 180 generates image data corresponding to the user's brain wave pattern based on the results of the analysis (S1730). More specifically, the controller 180 may generate the image data corresponding to the user's brain wave pattern by mapping frequency bands of the received brain waves to pixel regions in an image frame and mapping the levels of the received brain waves to certain pixel values.

Audio data or haptic data corresponding to the user's brain wave pattern may be generated in addition to the image data. More specifically, the controller 180 may generate audio data corresponding to the user's brain wave pattern by mapping the frequency band of the received brain waves to an audible frequency band and mapping the frequencies of the received brain waves to audible frequencies. The controller 180 may generate haptic data corresponding to the user's brain wave pattern by mapping variations in the average frequency of the received brain waves to variations in amplitude.

The image data, the audio data and the haptic data corresponding to the user's brain wave pattern are all perceivable to humans, and will hereinafter be collectively referred to as 'perception data.' The user's brain wave pattern detected by the brain wave sensor 147 may indicate the user's state of mind and perception data stored in or generated by the mobile terminal 100 may be related to the user's state of mind.

More specifically, if the perception data reflects the user's current state of mind, it may be referred to as having a positive correlation with the user's state of mind. On the other hand, if the perception data reflects a change in the user's current state of mind, such that the user's state of mind changes completely upon the output of perception data, the perception data may be referred to as having a negative correlation with the user's state of mind. According to this embodiment, it is possible to use image data, audio data, and or haptic data corresponding to the user's brain wave pattern in various functions performed by the mobile terminal 100.

Figure 29:
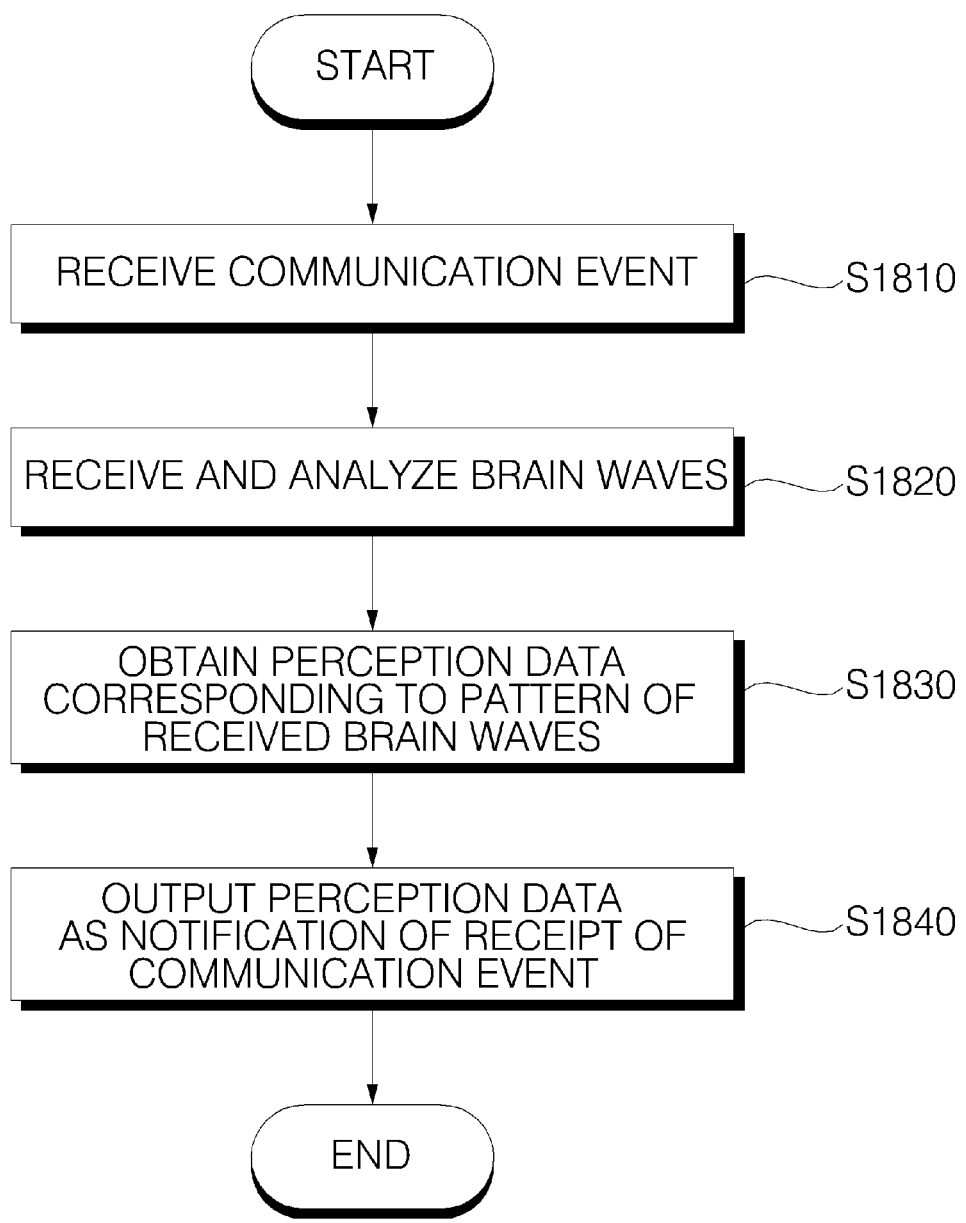
FIG. 29 is a flowchart illustrating a method of alerting a user using the user's brain wave pattern upon receiving a communication event according to an embodiment of the present invention.

FIG. 29 illustrates a flowchart of a method of notifying a user of the receipt of a communication event using the user's brain wave pattern according to an embodiment of the present invention. Referring to FIG. 29, the mobile terminal 100 receives a communication event (S1810). The mobile terminal 100 may receive various communication events via the wireless communication unit 110 without additional user manipulation.

The various communication events may be information received without being requested and may include call requests, missed calls, messages, emails, updates on a social network service (SNS) website, and information sent by really simple syndication (RSS) readers. The various communication events may each consist of text, image data or a combination thereof.

When the communication event is received, the controller 180 receives an electric signal from the brain wave sensor 147 that is attached onto the head of a user, preprocesses the electric signal, and analyzes the user's brain wave pattern based on the preprocessed signal (S1820). The analysis of the user's brain waves has been described previously and a detailed description will be omitted.

The controller 180 obtains perception data corresponding to the user's brain wave pattern (S1830). More specifically, the controller 180 searches a mentality database for a reference brain wave pattern that matches the user's brain waves and reads out at least image data, audio data or haptic data corresponding to the matching reference brain wave pattern for the user's brain waves from the mentality database in order to obtain the perception data. Alternatively, if there is no matching reference brain wave pattern for the user's brain waves in the mentality database, the controller 180 may generate the image data, audio data and haptic data corresponding to the user's brain waves as the perception data.

Thereafter, the controller 180 outputs the perception data as a notification of the receipt of a communication event (S1840). The controller 180 may output different types of perception data for different operating modes of the mobile terminal 100 and this will be described in detail with reference to FIG. 30.

Figure 30:
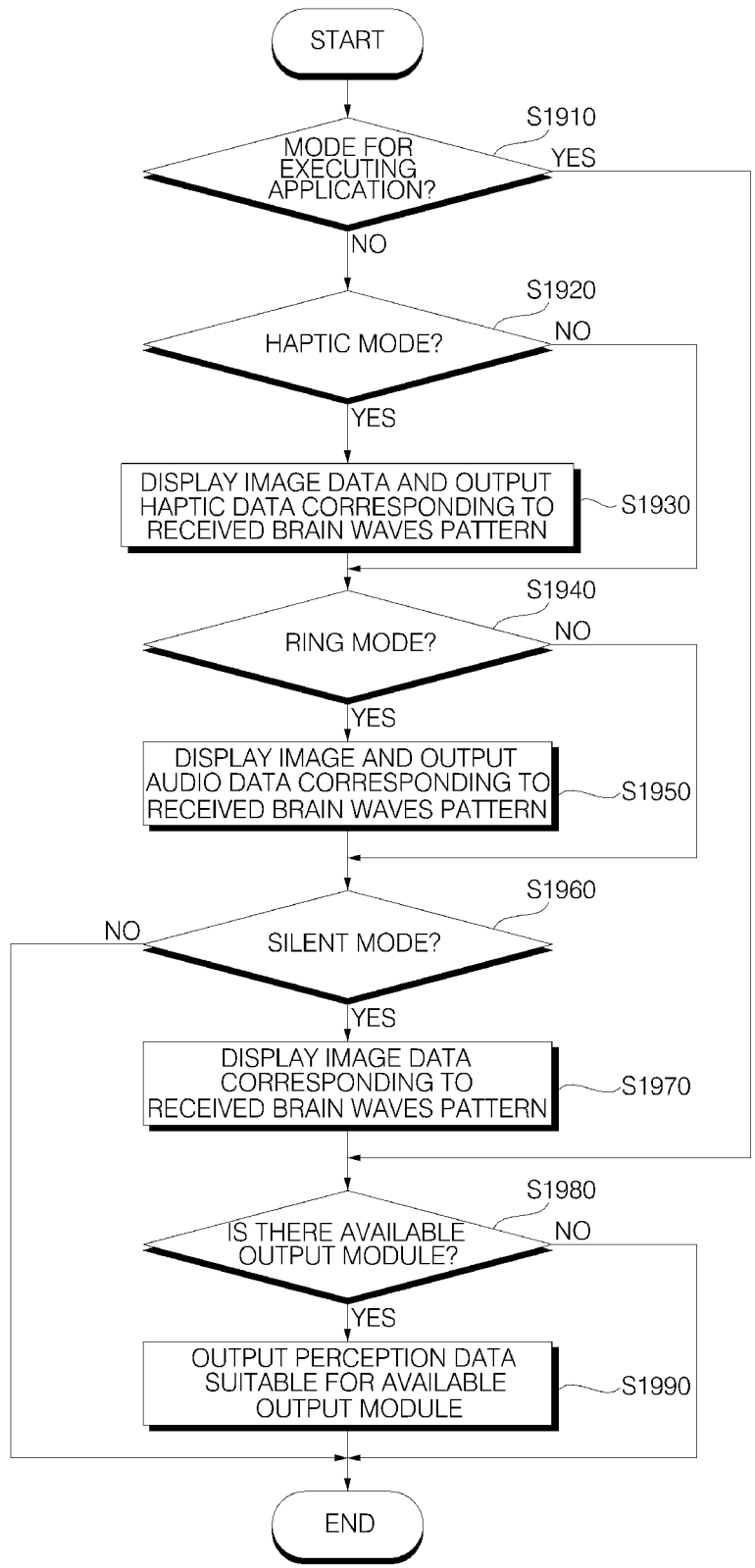
FIG. 30 is a flowchart illustrating a method of outputting different types of perception data for different operating modes of a mobile terminal according to an embodiment of the present invention.

FIG. 30 illustrates a flowchart of a method of outputting different types of perception data for different operating modes of a mobile terminal 100 according to an embodiment of the present invention. Referring to FIG. 30, if the mobile terminal 100 is in a haptic mode and not in a mode for executing an application (S1910), such as in an idle mode (S1920) when a communication event is received, the controller 180 displays image data corresponding to a user's brain wave pattern on the display module 151 and outputs haptic data corresponding to the user's brain wave pattern via the haptic module 153 (S1930). If the mobile terminal 100 is in the idle mode (S1910) and a ringer mode (S1940) when the communication event is received, the controller 180 displays the image data corresponding to the user's brain wave pattern on the display module 151 and outputs audio data corresponding to the user's brain wave pattern via the audio output module 152 (S1950). If the mobile terminal 100 is in the idle mode (S1910) and a silent mode (S1960) when the communication event is received, the controller 180 displays the image data corresponding to the user's brain wave pattern on the display module 151 (S1970).

If the mobile terminal 100 is in a mode for executing an application (S1910), or not in the idle mode, when the communication event is received, the controller 180 determines if the display module 151, the audio output module 152, or the haptic module 153 is currently not being used (S1980). If at least the display module 151, the audio output module 152, or the haptic module 153 is not currently being used (S1980), the controller 180 outputs a type of perception data that suits whichever of the display module 151, the audio output module 152, or the haptic module 153 is not currently being used (S1990).

For example, if the display module 151 is not currently being used, the controller 180 displays the image data corresponding to the user's brain wave pattern on the display module 151. If the audio output module 152 is not currently being used, the controller 180 outputs the audio data corresponding to the user's brain wave pattern. If the haptic module is not currently being used, the controller 180 outputs the haptic data corresponding to the user's brain wave pattern.

In this embodiment, different types of perception data corresponding to the user's brain wave pattern are obtained and then selectively output according to the operating mode of the mobile terminal 100. However, the present invention is not restricted to this. The operating mode of the mobile terminal 100 may be determined first and then a type of perception data that suits the operating mode of the mobile terminal and the user's brain wave pattern may be obtained.

Since perception data corresponding to the user's brain wave pattern is output as a notification of a communication event, it is possible to avoid a user's discomfort related typical notification data, provide additional information about the user's state of mind, or even change the user's state of mind. Perception data corresponding to the user's brain wave pattern may be used not only as notification data but also in various functions performed by the mobile terminal 100.

For example, the controller 180 may display image data corresponding to the user's brain wave pattern as a display screen on the display module 151. If the mobile terminal 100 is executing a particular application, the controller 180 may output a type of perception data that suits the user's brain wave pattern via whichever of the display module 151, the audio output module 152, or the haptic module 153 is not currently being used in the execution of the particular application.

The controller 180 may provide the user with information on his or her brain wave pattern by outputting perception data at regular intervals of time. The controller 180 may change an avatar or a game character representing the user according to the user's brain wave pattern. This will be described in detail with reference to FIG. 31.

Figure 31:
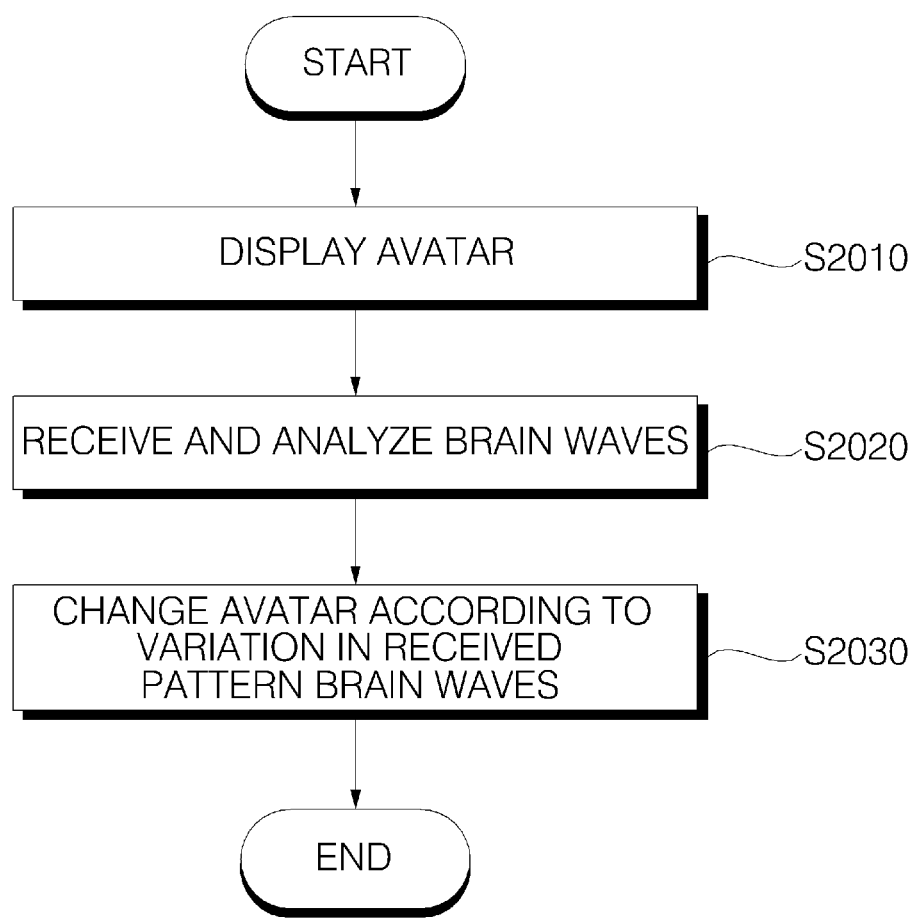
FIG. 31 is a flowchart illustrating a method of displaying an avatar corresponding to a brain wave pattern according to an embodiment of the present invention.

FIG. 31 illustrates a flowchart of a method of displaying an avatar corresponding to a user's brain wave pattern according to an embodiment of the present invention. Referring to FIG. 31, an avatar is displayed on a display screen of the display module 151 (S2010).

For example, during the execution of a game application, an avatar identifying a user that can be controlled by the user may be displayed on a display screen relevant to the game application. The avatar may also be displayed on a web application screen, such as a messenger screen, or on a blog screen or a background screen according to a user setting.

The controller 180 receives a signal representing a user's brain waves from the brain wave sensor 147 that is attached to the head of a user, preprocesses the signal, and analyzes the user's brain wave pattern based on the preprocessed signal (S2020). The analysis of the user's brain waves has already been described and a detailed description will be omitted.

Thereafter, the controller 180 changes the avatar according to a variation in the user's brain wave pattern (S2030). The controller 180 searches a mentality database for a reference brain wave pattern that matches the user's brain wave pattern, obtains an avatar image corresponding to the matching reference brain wave pattern and displays the obtained avatar image on the display module 151. Whenever the user's brain wave pattern changes, the controller 180 obtains an avatar image from the mentality database and displays the obtained avatar image on the display module 151.

The mentality database provided in the memory 160 stores different avatar images for different reference brain wave patterns. The obtained avatar image may be an image related to the motion, facial expression, size or power of the avatar.

The user's brain wave pattern may be converted into a particular numeric value and the numeric value may be transmitted to another mobile terminal 100. More specifically, the user's brain wave pattern may be compared with a reference brain wave pattern and then converted into the particular numeric value based on a level of similarity between the user's brain wave pattern and the reference brain wave pattern.

For example, if the user's brain wave pattern is 20% similar to the reference brain wave pattern, the particular numeric value may be 20. The particular numeric value may be used in a game application, such as a game character's power.

The methods illustrated in FIGS. 27 through 31 will be described in further detail with reference to FIGS. 32 through 37.

Figure 32:
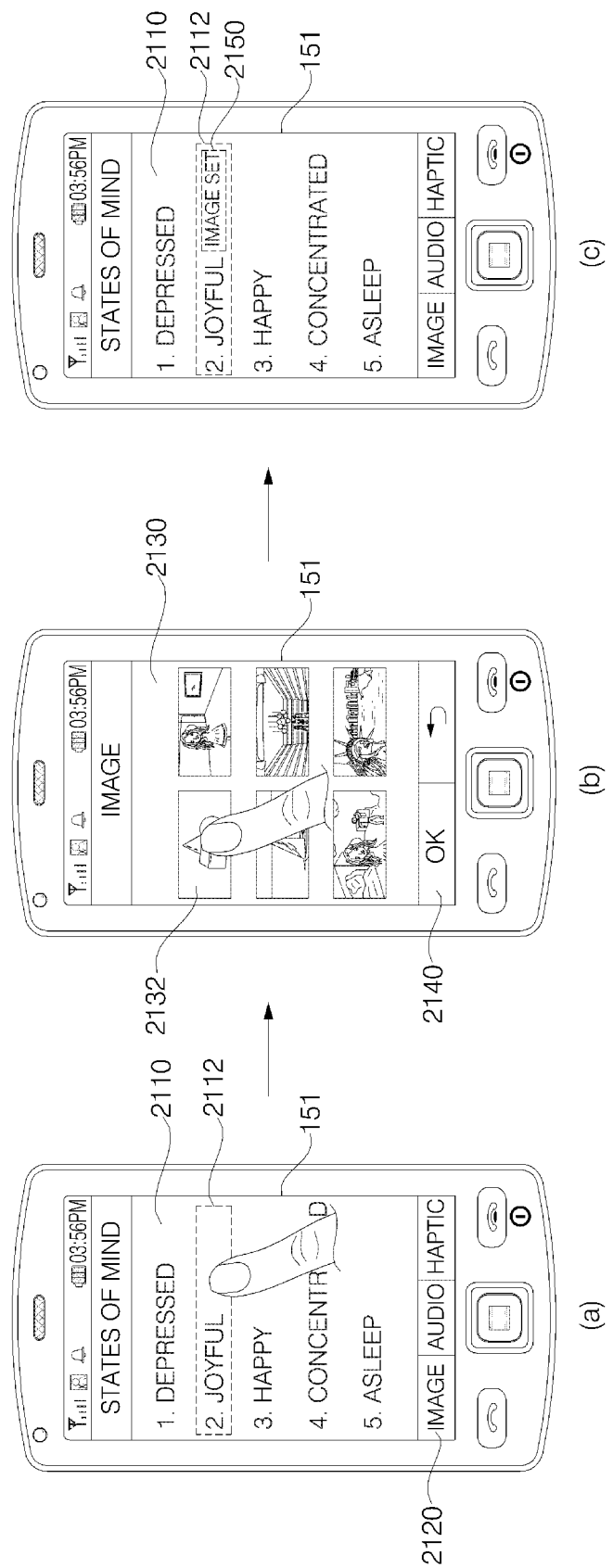
FIG. 32 is a diagram illustrating an example of registering image data corresponding to a user's state of mind.

FIG. 32 illustrates an example of registering image data corresponding to a user's state of mind. Referring to FIG. 32(*a*), various states of mind are listed on a state-of-mind list screen 2110 on the display module 151 and corresponding reference brain wave patterns are stored in a mentality database in the memory 160.

If a user selects one of the states of mind listed on the state-of-mind list screen 2110, such as 'joyful' 2112, and presses an 'image' key 2120 to register image data corresponding to the 'joyful' state, a candidate image screen 2130 showing a plurality of image data that can be registered may be displayed on the display module 151, as shown in FIG. 32(*b*). If the user selects one of the plurality of image data, such as an image 2132, and presses an 'OK' key 2140, the selected image may be registered for the 'joyful' state 2112. Then, an indicator 2150 indicating that the image 2132 has been registered may be displayed next to the 'joyful' state 2112 on the display module 151, as shown in FIG. 32(*c*).

Figure 33:
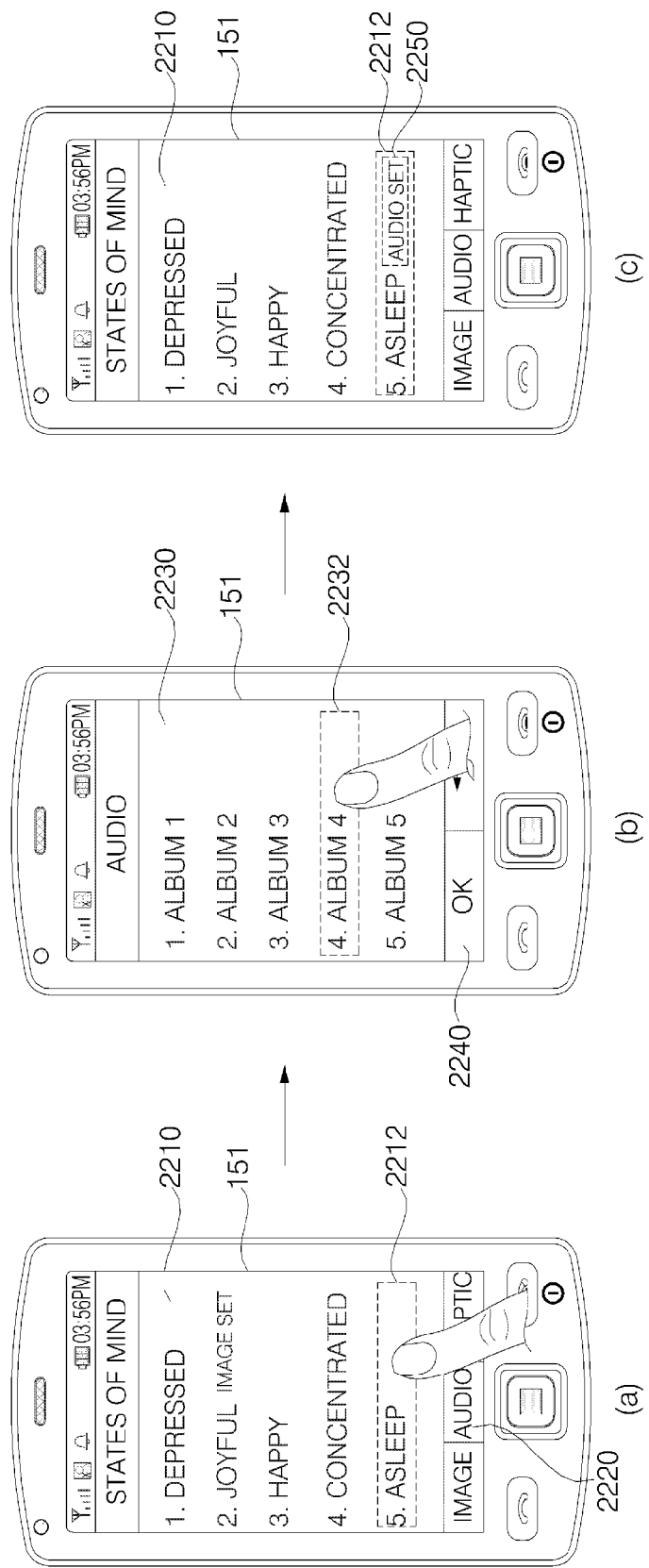
FIG. 33 is a diagram illustrating another example of registering image data corresponding to a user's state of mind.

FIG. 33 illustrates an example of registering audio data corresponding to a user's state of mind. Referring to FIG. 33(*a*), various states of mind are listed on a state-of-mind list screen 2210 on the display module 151 and corresponding reference brain wave patterns are stored in a mentality database in the memory 160.

If a user selects one of the states of mind listed on the state-of-mind list screen 2210, such as an 'asleep' state 2212, and presses an 'audio' key 2220 to register audio data corresponding to the 'asleep' state, a candidate audio screen 2230 showing a plurality of audio data that can be registered may be displayed on the display module 151, as shown in FIG. 33(*b*). If the user selects one of the plurality of audio data, such as album 4 (2232), and presses an 'OK' key 2240, album 4 may be registered for the 'asleep' state 2212. Then, an indicator 2250 indicating that album 4 has been registered may be displayed next to the 'asleep' state 2212 on the display module 151, as shown in FIG. 33(*c*).

As previously described, at least image data, audio data or haptic data can be registered for each reference brain wave pattern. If there is a matching reference brain wave pattern for a brain wave pattern provided by the brain wave sensor 147, at least image data, audio data or haptic data corresponding to the matching reference brain wave pattern can be output.

Figure 34:
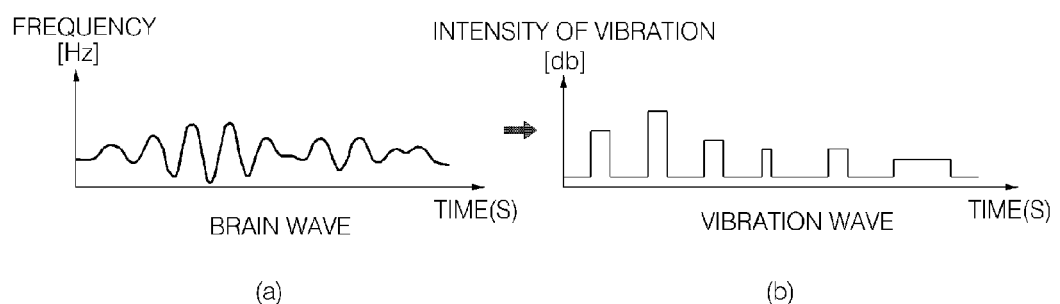
FIG. 34 is a diagram illustrating an example of generating haptic data corresponding to a user's brain wave pattern.

FIG. 34 illustrates an example generating haptic data corresponding to a user's brain wave pattern. Referring to FIG. 34(*a*), the controller 180 analyzes the variation of a predetermined brain wave within a particular frequency band or an average frequency band on a time domain. Thereafter, referring to FIG. 34(*b*), the controller 180 generates a vibration wave that can be perceived by a human according to the variation of the predetermined brain wave.

If the amount of variation in the predetermined brain wave increases, the controller 180 may increase the amplitude of the vibration wave. On the other hand, if the amount of variation in the predetermined brain wave decreases, the controller 180 may reduce the amplitude of the vibration wave.

Brain waves are not perceivable to humans. Therefore, brain waves may be converted into vibration data, audio data, or image data that can be perceived by humans. In this way, it is possible for a user to intuitively identify his or her brain wave pattern.

Figure 35:
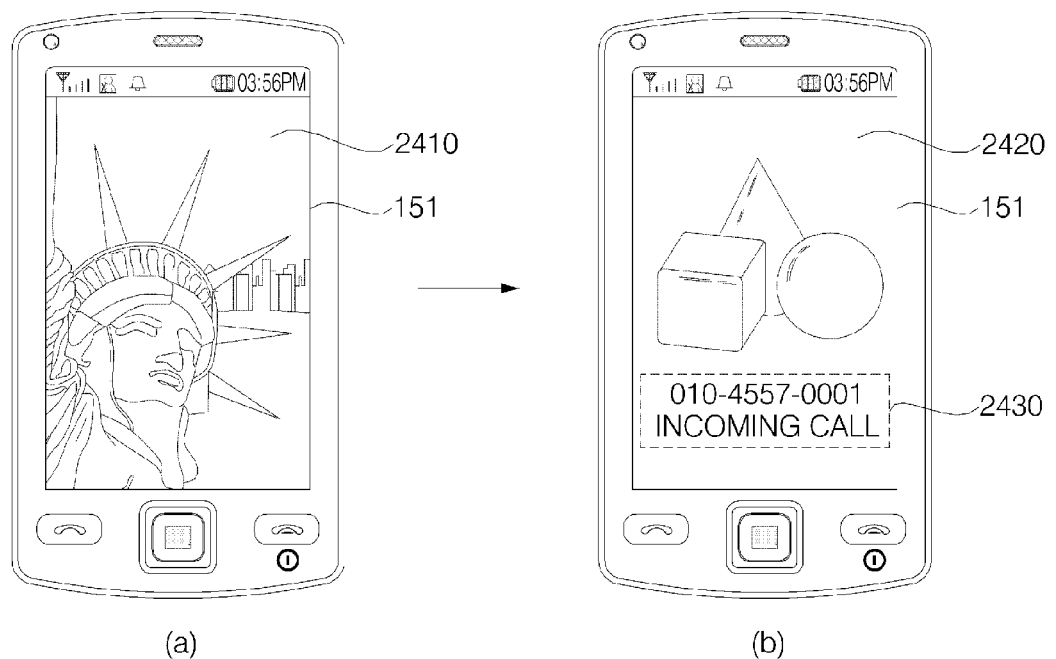
FIG. 35 is a diagram illustrating an example of displaying image data corresponding to a user's brain wave pattern upon the receipt of a communication event.

FIG. 35 illustrates displaying image data corresponding to a brain wave pattern upon the receipt of a communication event. Referring to FIG. 35(a), an idle screen 2410 is displayed on the display module 151 when the mobile terminal 100 is in an idle mode.

If a communication event for requesting a call connection is received from a counterpart mobile terminal, the controller 180 receives a user's brain waves from the brain wave sensor 147 and analyzes the received brain waves. Thereafter, the controller 180 searches a mentality database in the memory 160 for a reference brain wave pattern that matches the user's brain wave pattern. For example, if the reference brain wave pattern that matches the user's brain wave pattern is a brain wave pattern corresponding to a joyful state, the controller 180 obtains perception data corresponding to the joyful state from the mentality database and displays the obtained perception data, such as image data 2420, on the display module 151, as shown in FIG. 35(b).

The image data 2420 serves as a notification of the receipt of the communication event. The controller 180 may also display another notification 2430 of the receipt of the communication event using information related to the communication event.

Figure 36:
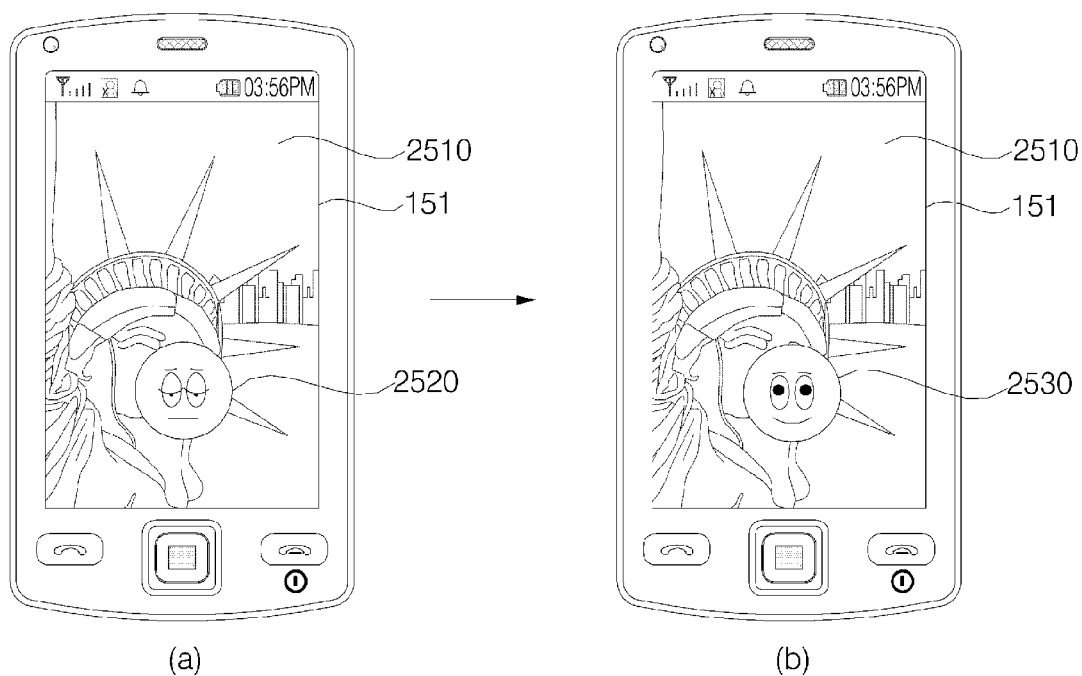
FIG. 36 is a diagram illustrating an example of displaying an avatar corresponding to a user's brain wave pattern.

FIG. 36 illustrates displaying the facial expression of an avatar according to a user's brain waves. Referring to FIG. 36(a), an avatar 2520 representing a user is displayed on a background screen 2510 of the display module 151. The controller 180 receives the user's brain waves from the brain wave sensor 147 and analyzes the received brain waves. Thereafter, the controller 180 searches a mentality database in the memory 160 for a reference brain wave pattern that matches the received brain waves. Thereafter, the controller 180 obtains an avatar 2530 corresponding to the matching reference brain wave pattern and displays the obtained avatar 2530 on the background screen 2510 of the display module 151 instead of the original avatar 2520.

As previously described, it is possible for the user to intuitively identify their state of mind or any variation of their state of mind since the image of an avatar changes almost in real time according to a user's brain waves.

Figure 37:
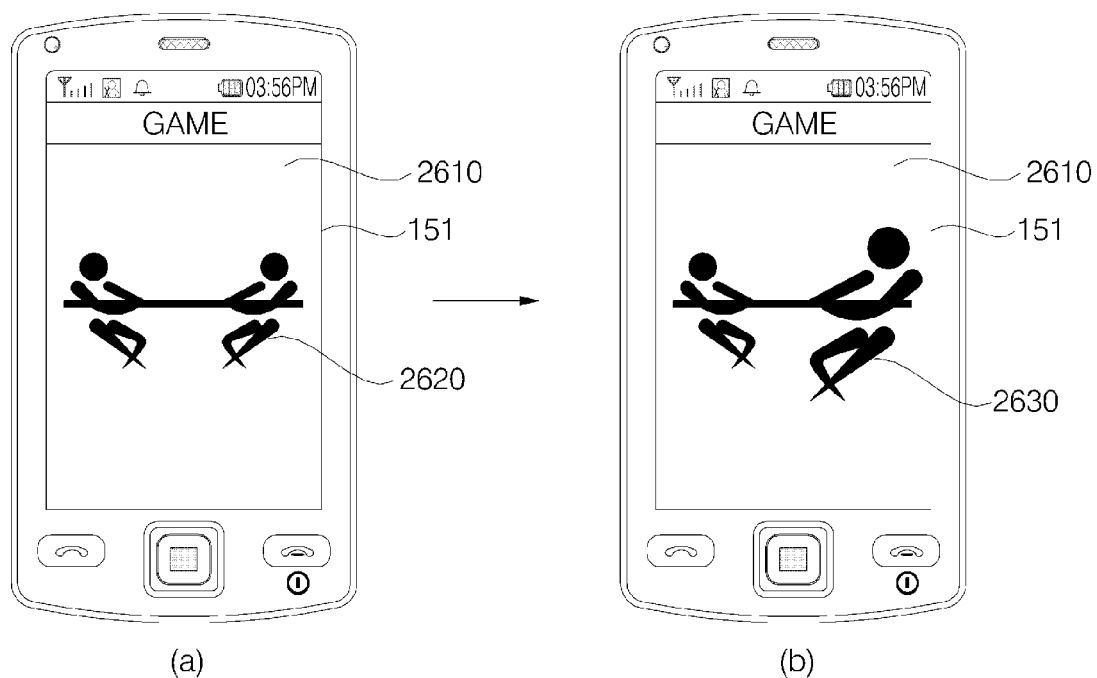
FIG. 37 is a diagram illustrating an example of changing the size of an avatar according to a user's brain wave pattern.

FIG. 37 illustrates an example changing the size of an avatar according to a user's brain waves. Referring to FIG. 37(a), an avatar or a game character 2620 representing a user is displayed on a game screen 2610 of the display module 151.

The controller 180 receives the user's brain waves from the brain wave sensor 147 and analyzes the received brain waves. The controller 180 determines a degree of similarity between the user's brain waves and a reference brain wave pattern previously stored in a mentality database in the memory 160. The controller 180 then changes the size of the avatar or the game character 2620 by an amount corresponding to the degree of similarity between the user's brain waves and the reference brain wave pattern and displays an avatar or a game character 2630 with the changed size, as shown in FIG. 37(b).

Figure 38:
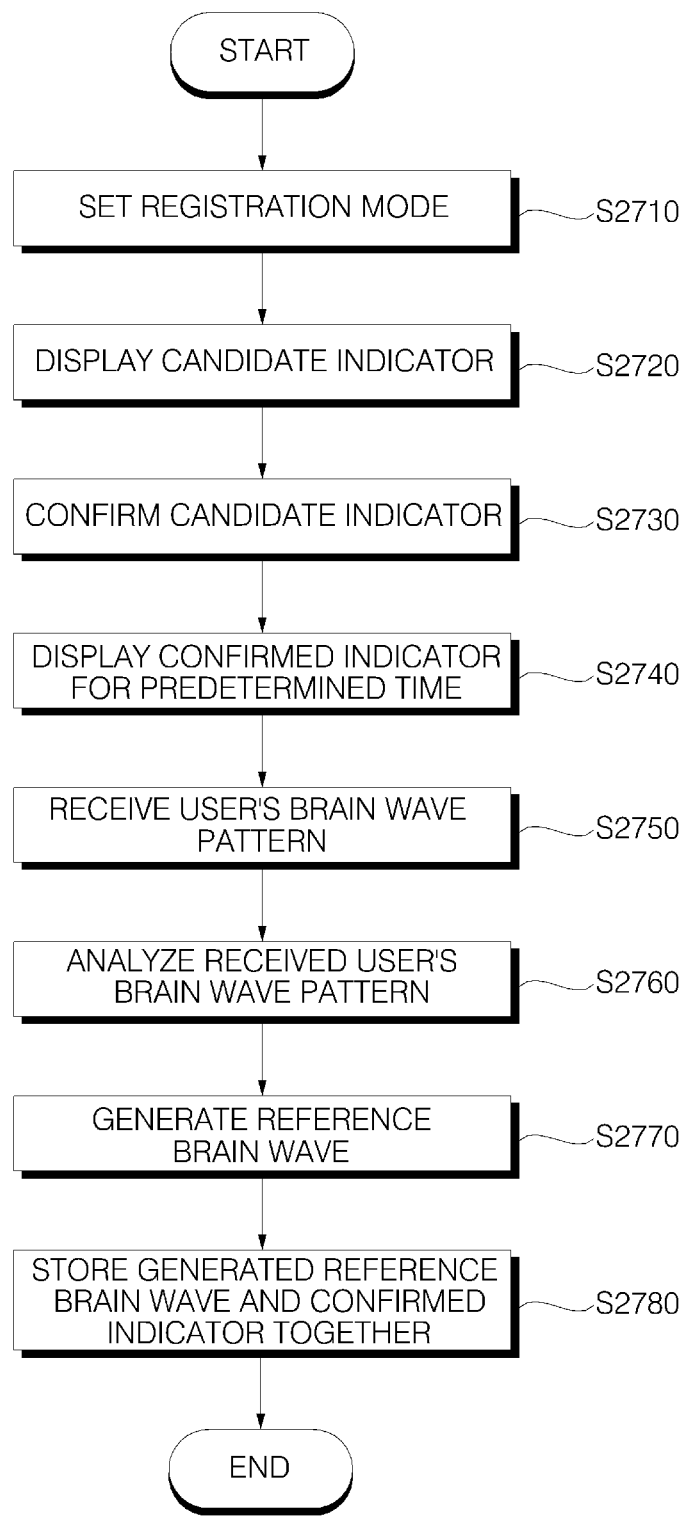
FIG. 38 is a flowchart of a method of registering a reference brain wave pattern according to an embodiment of the present invention.

FIG. 38 illustrates a flowchart of a method of registering a reference brain wave pattern according to an embodiment of the present invention. Referring to FIG. 38, the controller 180 sets a registration mode for registering a reference brain wave pattern in response to a user command (S2710).

An operating mode of the mobile terminal 100 may be primarily classified as a regular mode or a brain wave mode. The regular mode is an operating mode in which the mobile terminal 100 is driven in response to a user command input via the user input unit 130 and the brain wave mode is an operating mode in which the mobile terminal 100 is driven in response to the user's brain wave pattern. The brain wave mode is classified into a registration mode, a verification mode for verifying whether the user's brain wave pattern can be recognized as a user command, and an application mode for applying the user's brain wave pattern to the mobile terminal 100 as a user command in order to control operation of the mobile terminal 100.

Once the registration mode is set (S2710), the controller 180 displays a number of candidate indicators on the display module 151 (S2720) that can be associated with a reference brain wave pattern to be registered. The candidate indicators may be images of, for example, arrows or icons that are descriptive enough for the user to form a predetermined brain wave pattern.

If the user selects one of the candidate indicators, the controller 180 determines that an indicator has been confirmed for association with a reference brain wave pattern to be registered (S2730). The controller 180 displays the confirmed indicator on the display module 151 for a predefined amount of time (S2740) and receives a brain wave signal representing a user's brain wave pattern detected for the predefined amount of time by the brain wave sensor 147 (S2750).

The controller 180 analyzes the user's brain wave pattern by performing signal processing on the received brain wave signal (S2760). More specifically, the controller 180 may receive an electric signal from the brain wave sensor 147, amplify the received electric signal, remove spurious components from the amplified electric signal, and convert the resulting electric signal into a digital signal. Thereafter, the controller 180 may Fourier-transform the digital signal and analyze the user's brain waves based on the Fourier-transformed digital signal.

The controller 180 generates a reference brain wave based on the results of the analysis of the user's brain wave pattern (S2770). The generated reference brain wave may be an average of the brain waves received for the predefined amount of time.

The controller 180 stores the generated reference brain wave and the confirmed indicator together in a command database (S2780). The command database stores a plurality of reference brain waves and corresponding indicators and commands. In this manner, when a brain wave is received, the controller 180 determines whether there is a match for the received brain wave in the command database, and operates the mobile terminal 100 in accordance with a command corresponding to a reference brain wave that matches the received brain wave.

The confirmed indicator may include information related to a command associated with the generated reference brain wave. If the confirmed indicator does not include information related to a command associated with the generated reference brain wave, the controller 180 may also display the information related to the command associated with the generated reference brain wave along with the confirmed indicator.

An indicator may have a one-on-one correspondence with a command. Alternatively, an indicator may be associated with more than one command.

According to this embodiment, it is possible to realize a user-friendly user interface (UI) by freely matching reference brain waves registered by a user with indicators.

Figure 39:
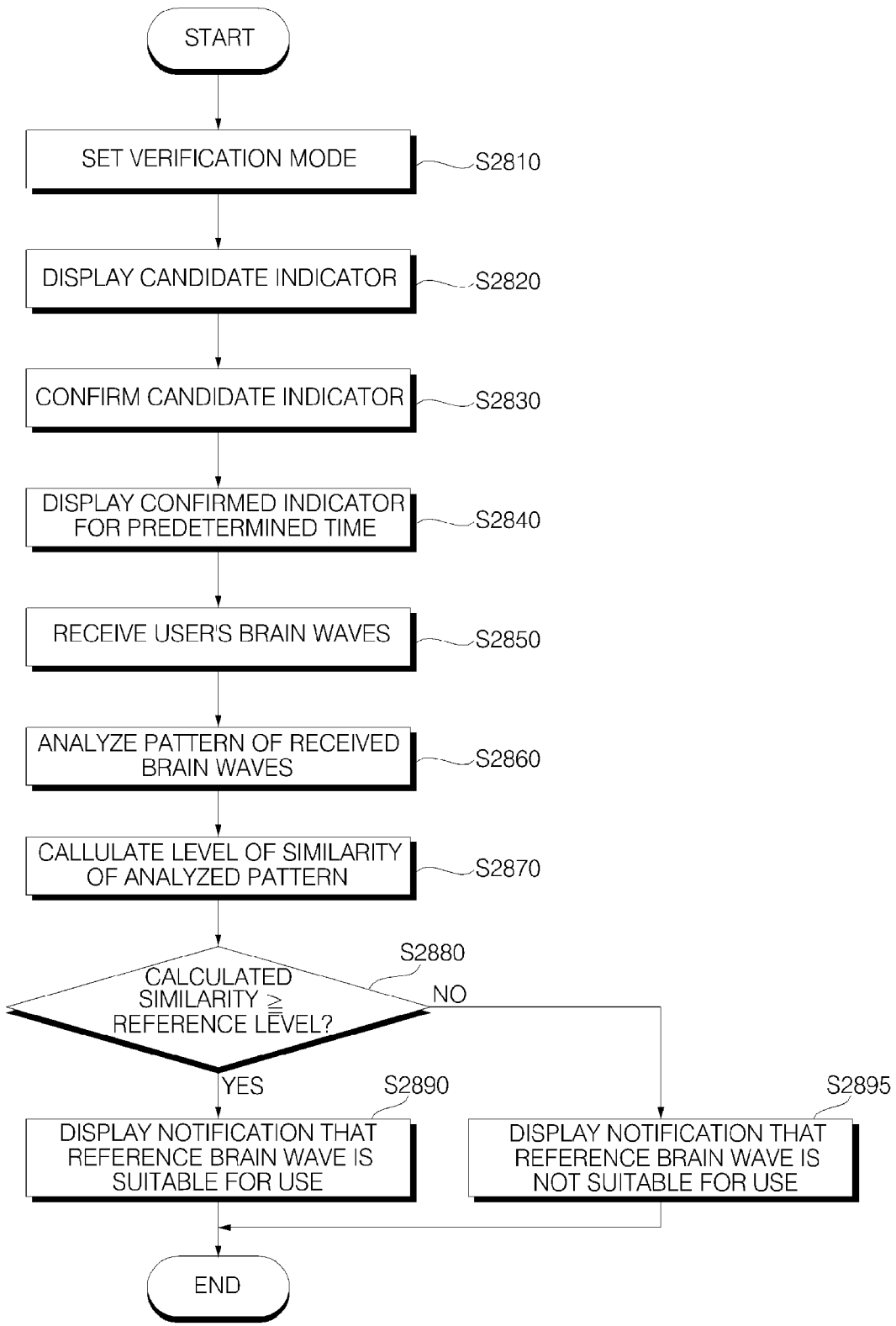
FIG. 39 is a flowchart of a method of verifying a reference brain wave pattern according to an embodiment of the present invention.

FIG. 39 illustrates a flowchart of a method of verifying a reference brain wave according to an embodiment of the present invention. Referring to FIG. 39, the controller 180 sets a verification mode for verifying a reference brain wave in response to a user command (S2810).

The controller 180 displays a number of candidate indicators on the display module 151 (S2820). The candidate indicators are previously-stored indicators each associated with reference brain waves. If a user selects one of the candidate indicators, the controller 180 confirms the selected candidate indicator as an indicator to be verified (S2830) and displays the confirmed indicator on the display module 151 for a predefined amount of time (S2840).

The controller 180 receives brain waves from a user detected for the predefined amount of time by the brain wave sensor 147 (S2850) and analyzes the pattern of the received brain waves (S2860). The analysis of brain waves has already been described previously and a detailed description will be omitted.

The controller 180 calculates a level of similarity between the analyzed pattern of the received brain waves and a reference brain wave corresponding to the confirmed indicator (S2870). For example, the controller 180 may compare the levels of the received brain waves with the level of the reference brain wave and determine the level of similarity based on the results of the comparison. The more the received brain waves fall within a reference range set based on the reference brain wave, the higher the level of similarity between the received brain waves and the reference brain wave.

Alternatively, the controller 180 may determine the level of similarity between the received brain waves and the reference brain wave by converting the frequencies of the received brain waves into ratios with respect to an entire frequency band and comparing the ratios with the reference brain wave. The more of the ratios fall within a reference range set based on the reference brain wave, the higher the level of similarity between the received brain waves and the reference brain wave becomes.

The reference range may have an error range and may be adjusted based on the error range. The level of similarity between the received brain waves and the reference brain wave may be calculated using method other than those previously set forth, such as a maximum likelihood method or a cross-correlation method.

In this embodiment, the brain waves of the user are detected for more than a predefined period of time with the detected brain waves then compared with a reference brain. However, the present invention is not restricted to this. The brain waves of the user may be compared in real time with a reference brain wave such that the level of similarity between the brain waves of the user and the reference brain wave may calculated based on the results of the comparison.

If the level of similarity between the received brain waves and the reference brain wave is higher than a predefined level (S2880), the controller 180 may display notification data on the display module 151 indicating that the reference brain wave is suitable for use as a user command (S2890). On the other hand, if the level of similarity between the received brain waves and the reference brain wave is lower than the predefined level (S2880), the controller 180 may display notification data on the display module 151 indicating that the reference brain wave is not suitable for use as a user command (S2895).

According to this embodiment, it is possible to effectively verify whether and how much each registered reference brain wave is suitable for use as a user command.

Figure 40:
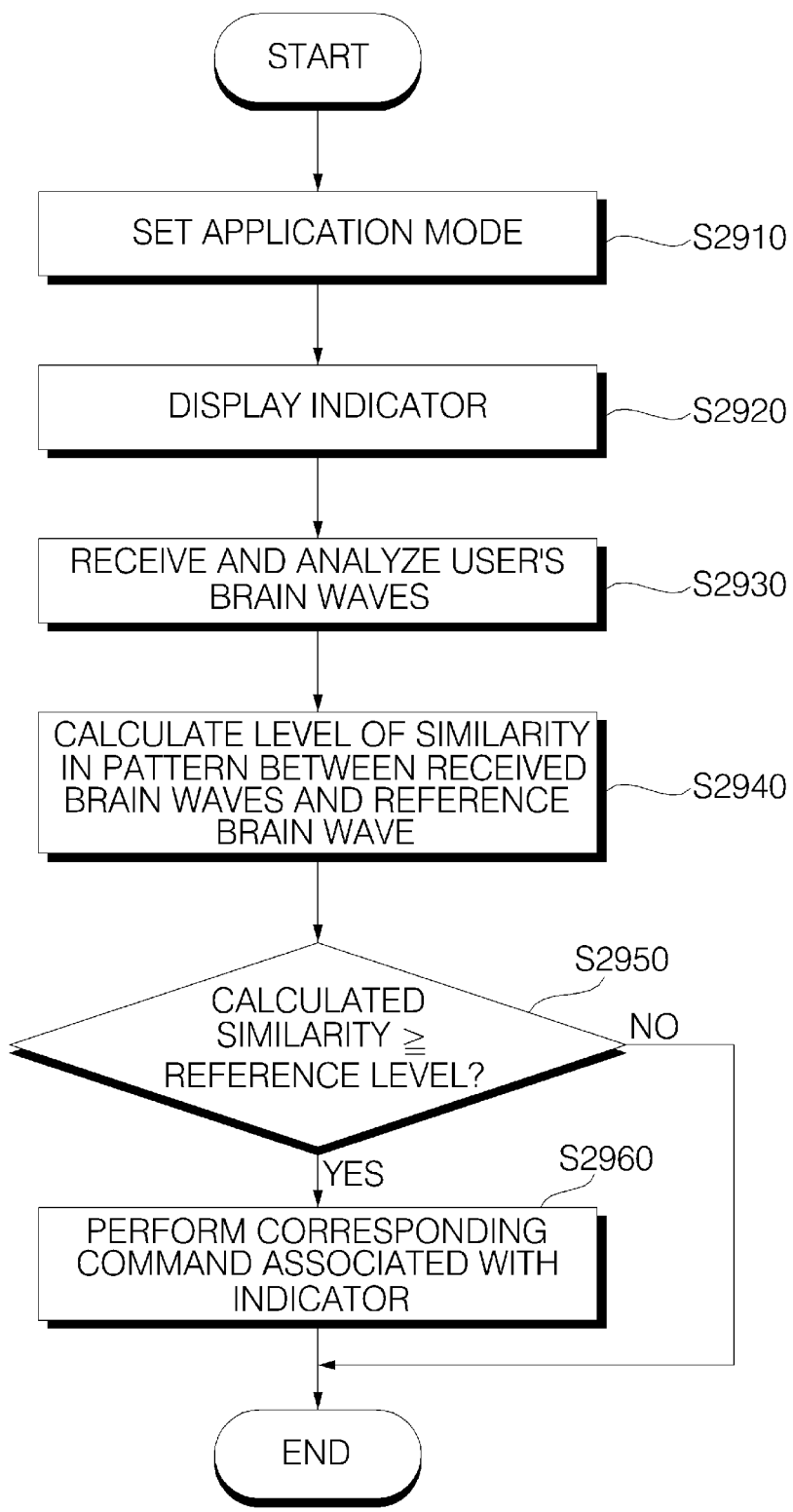
FIG. 40 is a flowchart of a method of controlling a mobile terminal based on a user's brain wave pattern according to an embodiment of the present invention.

FIG. 40 illustrates a flowchart of a method of controlling a mobile terminal based on a user's brain wave pattern according to an embodiment of the present invention. Referring to FIG. 40, when an application mode in which a reference brain wave can be used as a command is set (S2910), the controller 180 displays at least one indicator on the display module 151 (S2920).

The indicator may include information related to a command associated with the indicator. Otherwise, the controller 180 may also display information related to the command associated with the indicator on the display module 151.

The controller 180 receives and analyzes a user's brain waves detected by the brain wave sensor 147 (S2930). The analysis of brain waves has already been previously described in detail and detailed description will be omitted.

Thereafter, the controller 180 calculates the level of similarity in pattern between the received brain waves and a reference brain wave corresponding to the indicator (S2940). The controller 180 may calculate the level of similarity in pattern between the received brain waves and the reference brain wave corresponding to the indicator by comparing the received brain waves with the reference brain wave corresponding to the indicator.

If the level of similarity in pattern between the received brain waves and the reference brain wave corresponding to the indicator is higher than a predefined level (S2950), the controller 180 performs an operation corresponding to the command associated with the indicator (S2960). The command associated with the indicator may vary from one application mode to another application mode. This will be described later in detail.

Figure 41:
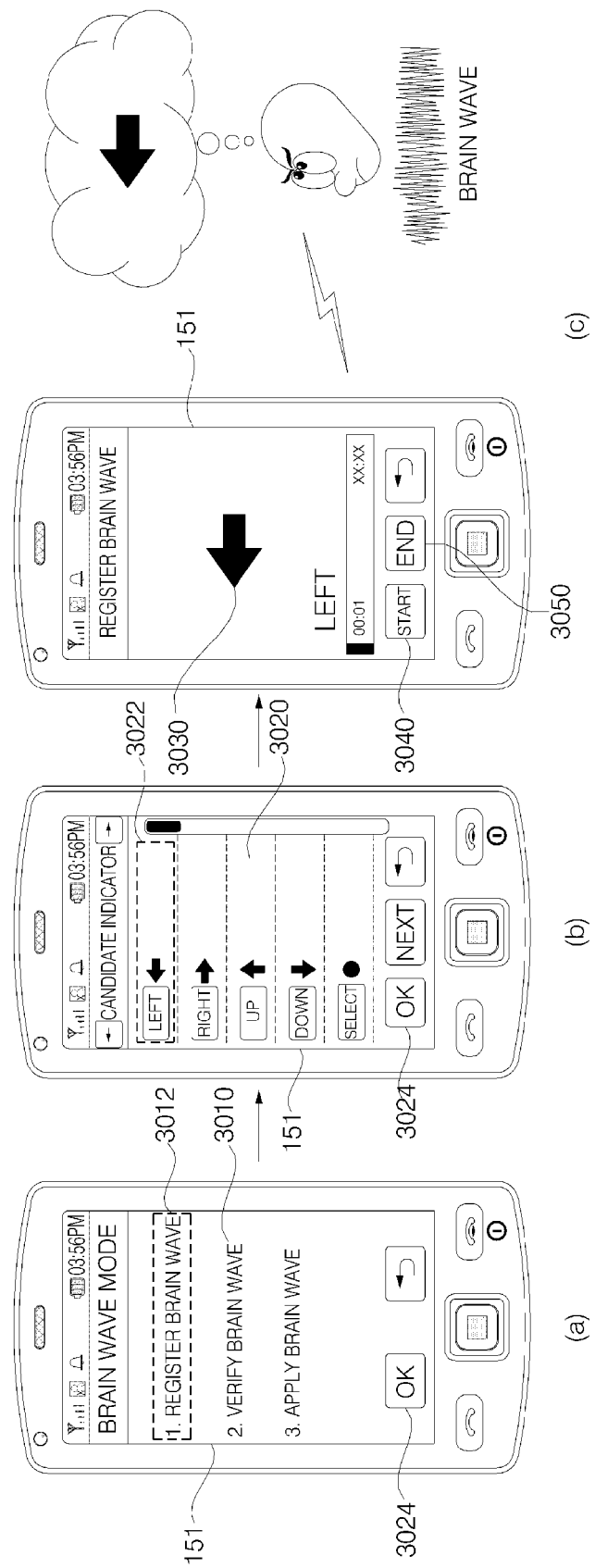
FIG. 41 is a diagram illustrating an example of registering a reference brain wave pattern.

FIG. 41 illustrates an example of registering a reference brain wave. Referring to FIG. 41(a), when a user selects a brain wave mode from a menu screen, a sub-menu screen 3010 for the brain wave mode is displayed on the display module 151.

If the user selects a 'register brain wave' item 3012 from the sub-menu screen 3010 to register a reference brain wave, a candidate indicator screen 3020 showing at least one candidate indicator that can be registered together with a reference brain wave is displayed on the display module 151, as shown in FIG. 41(b). If the user then selects an indicator 3022 from the candidate indicator screen 3020 and then presses an 'OK' key 3024, an enlarged version 3030 of the indicator 3022 is displayed, as shown in FIG. 41(c).

If the user then presses a 'start' key 3040 and thinks of something related to the indicator 3030, the controller 180 receives and analyzes brain waves detected by the brain wave sensor 147 from the user since the pressing of the 'start' key 3040 and calculates the levels of the received brain waves. The reception and analysis of brain waves may continue until the user presses an 'end' key 3050.

When the user presses the 'end' key 3050, the controller 180 registers one of the received brain waves having an average level as a reference brain wave. The reference brain wave may be registered together with the indicator 3030. When the registration of the reference brain wave is complete, a notification message may be displayed in order to alert the user.

In the example illustrated in FIG. 41, direction indicators are displayed as candidate indicators. However, the present invention is not restricted to this. Any types of indicators may be used as long as they can facilitate the user to generate particular brain wave patterns that can be easily recognized. Candidate indicators do not necessarily need to be image data and may be audio data, haptic data or a combination thereof.

Figure 42:
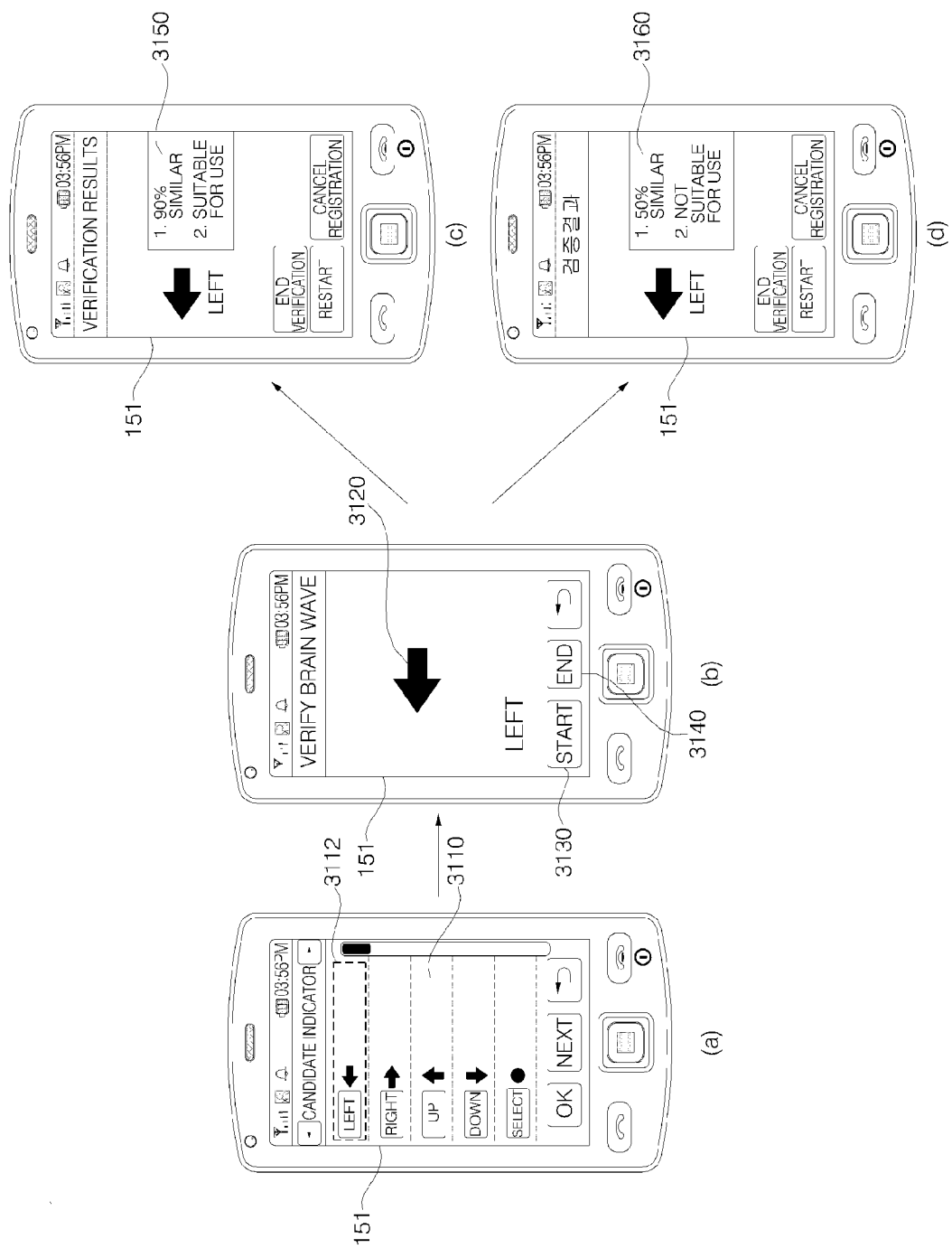
FIG. 42 is a diagram illustrating an example of verifying a reference brain wave pattern.

FIG. 42 illustrates an example of verifying a reference brain wave. Referring to FIG. 42(a), if a user selects a 'verify brain wave' item from a menu screen on the display module 151 shown in FIG. 41(a), a candidate indicator screen 3110 showing a plurality of indicators that are registered for corresponding reference brain waves is displayed.

If the user selects one of the indicators, such as an indicator 3112, an enlarged version 3120 of the indicator 3112 is displayed, as shown in FIG. 42(b). Then, if the user presses a 'start' key 3130 and thinks of something related to the indicator 3120, a particular brain wave pattern is generated. The controller 180 receives and analyzes brain waves detected by the brain wave sensor 147 from the user since the pressing of the 'start' key 3130 and calculates the levels of the received brain waves. The reception and analysis of brain waves may continue until the user presses an 'end' key 3140.

When the user presses the 'end' key 3140, the controller 180 calculates the level of similarity between one of the received brain waves having an average level and a reference brain wave corresponding to the indicator 3120. If the level of similarity between the average-level brain wave and the reference brain wave corresponding to the indicator 3120 is higher than a predefined level, a first notification message 3150 indicating that the reference brain wave is suitable for use as a user command is displayed on the display module 151, as shown in FIG. 42(c). On the other hand, if the level of similarity between the average-level brain wave and the reference brain wave corresponding to the indicator 3120 is lower than the predefined level, a second notification message 3160 indicating that the reference brain wave is not suitable for use as a user command is displayed on the display module 151, as shown in FIG. 42(d).

The user may maintain or cancel the registration of the reference brain wave corresponding to the indicator 3120 based on the results of the verification of the reference brain wave. In this way, it is possible to verify whether each reference brain wave is suitable for use as a user command.

Figure 43:
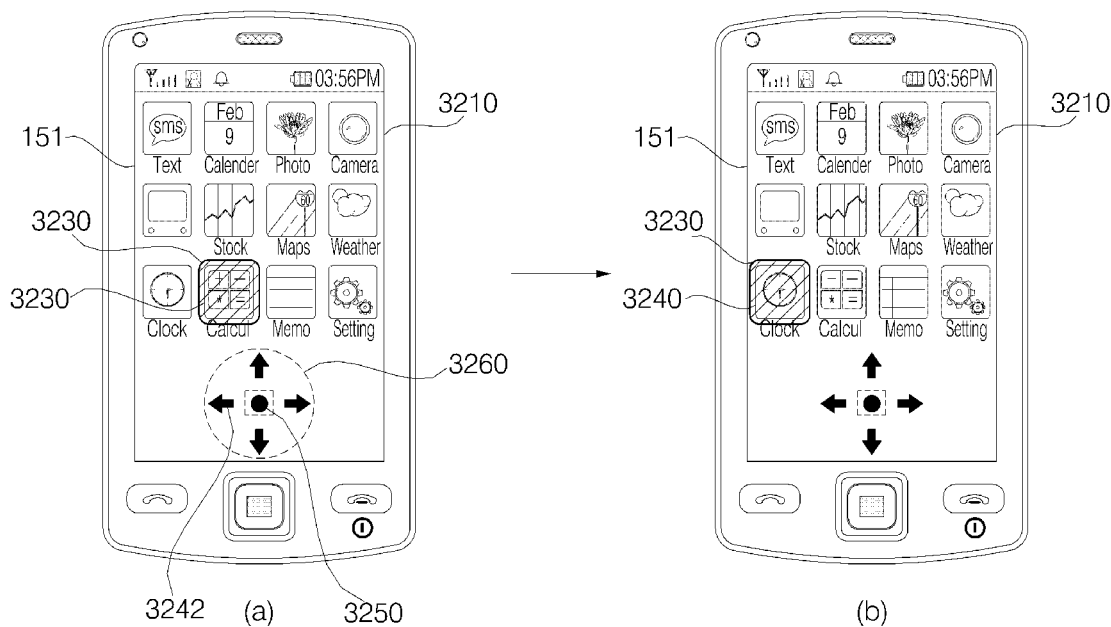
FIG. 43 is a diagram illustrating an example of using a reference brain wave pattern as a user command in a menu mode of an application mode.

FIG. 43 illustrates an example of using a reference brain wave as a user command in a menu mode of an application mode. Referring to FIG. 43(a), in the menu mode of the application mode, a plurality of items each corresponding to one of a plurality of services provided by the mobile terminal 100 are displayed on a menu screen 3210 on the display module 151. A highlight 3230 is placed over one of the items, such as an item 3220. Indicators 3242 and 3250 that are each associated with reference brain waves are also displayed on the menu screen 3210.

When the user thinks of an indicator related to a movement or motion of the highlight 3230, the controller 180 receives and analyzes brain waves detected by the brain wave sensor 147 from the user. If the level of pattern similarity between the received brain waves and a reference brain wave for moving the highlight 3230 is higher than a predefined level, the controller 180 acquires a command that is associated with the reference brain wave from a command database and moves the highlight according to the acquired command.

For example, if the user generates a particular brain wave pattern by looking at the indicator 3242 that is related to a leftward movement or motion and the particular brain wave has a higher level of pattern similarity with a reference brain wave for moving the highlight 3230 to the left than the predefined level, the controller 180 moves the highlight to the left and places the highlight over an item 3260, as shown in FIG. 43(b). Then, the user may think of an indicator 3250 that is related to a selection and enter a command to select the highlighted item.

When indicators do not include any information related to corresponding commands, the indicators may be displayed along with information related to corresponding commands in consideration that there may exist a variety of commands according to the type of application mode. The types of indicators are generally limited.

Figure 44:
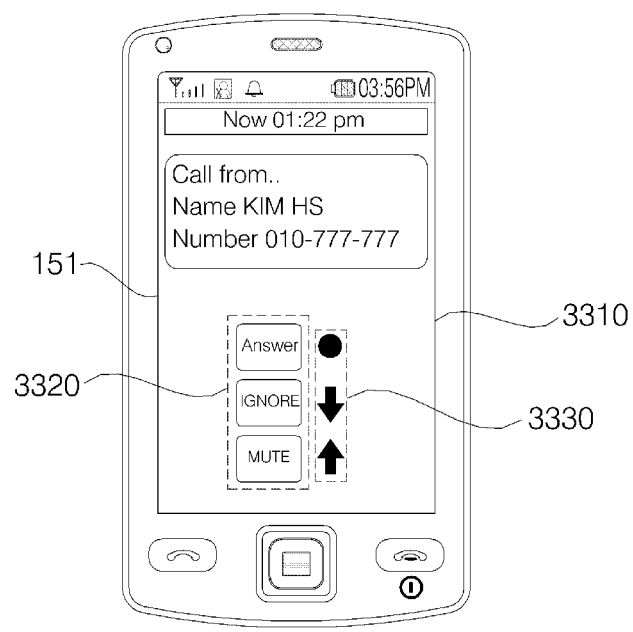
FIG. 44 is a diagram illustrating an example of operating a mobile terminal according to a user's brain wave pattern upon the receipt of a communication event.

FIG. 44 illustrates an example operating a mobile terminal according to a user's brain wave pattern upon the receipt of a communication event. Referring to FIG. 44, if a communication event, such as an incoming call signal, is received when an idle screen is displayed on the display module 151, the controller 180 displays a display screen 3310 related to the received incoming call signal and displays information 3320 related to various commands that can be used in connection with the received incoming call signal on the display screen. The controller 180 also displays indicators 3330 that are each associated with the various commands on the display screen 3310.

A user may think of a particular indicator related to answering a call in order to answer the received incoming call signal. Then, the controller 180 displays a display screen on the display module 151 that is associated with an incoming call connected to the mobile terminal 100 if the level of pattern similarity between brain waves detected by the brain wave sensor 147 from the user and a reference brain wave for answering a call is higher than a predefined level.

Figure 45:
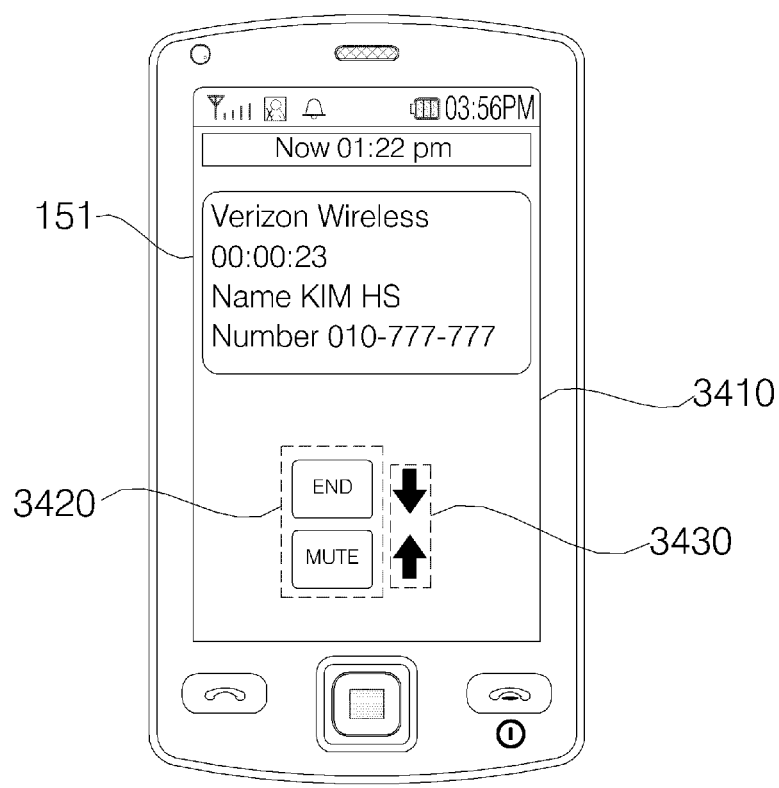
FIG. 45 is a diagram illustrating an example of operating a mobile terminal according to a user's brain wave pattern during a call.

FIG. 45 illustrates an example of operating the mobile terminal 100 according to a user's brain wave pattern during a call. Referring to FIG. 45, information 3420 related to various commands that can be used during a call and indicators 3430 that are each associated with one of the various commands are displayed on a display screen 3410 on the display module 151 during the call.

When a user thinks of an indicator related to ending a call in order to terminate the call, the brain wave sensor 147 detects brain waves from the user. Then, if the level of pattern similarity between the detected brain waves and a reference brain wave for ending a call is higher than a predefined level, the controller 180 determines that a command to end a call has been received, ends the call and displays a display screen associated with completion of a call.

Figure 46:
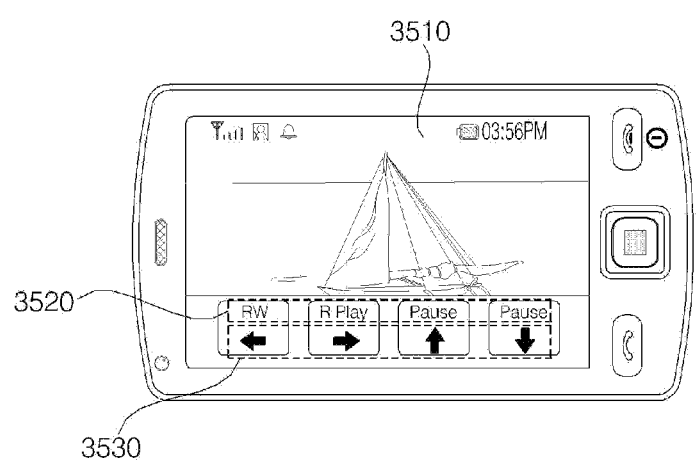
FIG. 46 is a diagram illustrating an example of operating a mobile terminal according to a user's brain wave pattern during the playback of a video file.

FIG. 46 illustrates an example of operating a mobile terminal according to a user's brain wave pattern during a video file playback mode. Referring to FIG. 46, information 3520 related to various commands that can be used in connection with playback of a video file and indicators 3530 that are each associated with one of the various commands are displayed on a display screen 3510 on the display module 151 during the playback of the video file. When brain waves having a higher level of pattern similarity to a reference brain wave for ending the playback of the video file than a predefined level are detected from a user, the controller 180 determines that a command to end the playback of the video file has been received and ends the playback of the video file.

In the disclosed embodiments of the present invention, image data is used as indicators corresponding to reference brain waves. However, the present invention is not restricted to this. Audio data, haptic data or a combination of audio data and haptic data may be used as indicators corresponding to reference brain waves.

While the present invention has been particularly shown and described with reference to various embodiments, it will be understood by those of ordinary skill in the art that various changes in form and details may be made therein without departing from the spirit and scope of the present invention as defined by the following claims.

Various embodiments described herein may be implemented in various ways. For example, the embodiments may be implemented in a computer-readable medium using computer software, hardware, or some combination thereof.

For a hardware implementation, the embodiments described may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination of these devices. The controller 180 may also implement such embodiments.

For a software implementation, the embodiments described herein may be implemented with separate software modules, such as procedures and functions, each of which perform one or more of the functions and operations described herein. The software codes can be implemented with a software application written in any suitable programming language and may be stored in memory, such as the memory unit 160, and executed by a controller or processor, such as the controller 180.

The present invention can be realized as code that can be read by a processor of a mobile terminal and can be written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the internet). The computer-readable recording medium can be distributed over a plurality of computer systems connected to a network such that computer-readable code is written and executed in a decentralized manner. Functional programs, code, and code segments necessary for realizing the present invention can be easily construed by one of ordinary skill in the art.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Other components may be coupled to the system. Input/output or I/O devices (including but not limited to keyboards, displays, pointing devices, etc.) can be coupled to the system either directly or through intervening I/O controllers. Network adapters (e.g., modem, cable modem, Ethernet cards) may also be coupled to the system to enable the data processing system to become coupled to other data processing systems or remote printers or storage devices through intervening private or public networks.

It should be understood that the logic code, programs, modules, processes, methods, and the order in which the respective elements of each method are performed are purely exemplary. Depending on the implementation, they may be performed in any order or in parallel, unless indicated otherwise in the present disclosure. Further, the logic code is not related, or limited to any particular programming language, and may be comprise one or more modules that execute on one or more processors in a distributed, non-distributed, or multiprocessing environment.

The method as described above may be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multi-chip package (such as a ceramic carrier that has either or both surface interconnections of buried interconnections).

In any case, the chip is then integrated with other chips, discrete circuit elements, and/or other signal processing devices as part of either (a) an intermediate product, such as a motherboard, or (b) and end product. The end product can be any product that includes integrated circuit chips, ranging from toys and other low-end applications to advanced computer products having a display, a keyboard or other input device, and a central processor.

Therefore, it should be understood that the invention can be practiced with modification and alteration within the spirit and scope of the appended claims. The description is not intended to be exhaustive or to limit the invention to the precise form disclosed. These and various other adaptations and combinations of the embodiments disclosed are within the scope of the invention and are further defined by the claims and their full scope of equivalents.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims. Therefore, all changes and modifications that fall within the metes and bounds of the claims, or equivalence of such metes and bounds are intended to be embraced by the appended claims.

The foregoing embodiments and advantages are merely exemplary and are not to be construed as limiting the present invention. The present teaching can be readily applied to other types of apparatuses.

The description of the present invention is intended to be illustrative, and not to limit the scope of the claims. Many alternatives, modifications, and variations will be apparent to those skilled in the art. In the claims, means-plus-function clauses are intended to cover the structure described herein as performing the recited function and not only structural equivalents but also equivalent structures.

What is claimed is:

1. A method of controlling operation of a mobile terminal, the method comprising:
   executing an application;
   determining whether a level of a brain wave that is classified into a specific frequency band is within a reference range; and
   storing at least image data or audio data relevant to the execution of the application if the level of the brain wave is within the reference range.

2. The method of claim 1, wherein the reference range represents a specific state of mind of a user.

3. The method of claim 1, further comprising displaying an indicator to notify a user that the at least image data or audio data is being stored while storing the at least image data or audio data.

4. The method of claim 1, wherein the image data comprises a plurality of images displayed during a period of time when the brain wave is within the reference range.

5. The method of claim 1, wherein the audio data comprises at least a user's voice or audio data output upon executing the application.

6. The method of claim 1, wherein the audio data comprises audio data transmitted or received by the mobile terminal during a period of time when the brain wave is within the reference range.

7. The method of claim 1, further comprising generating a highlight file based on the at least image data or audio data when the execution of the application is complete.

8. The method of claim 1, further comprising playing the at least image data or audio data in response to receiving a highlight play command for the application.

9. The method of claim 1, wherein the application comprises at least a call application, a video player application, an audio player application, a still image viewer application, a game application, a broadcast program viewer application or a web application.

10. The method of claim 1, wherein the specific frequency band comprises at least a beta-wave frequency band or an alpha-wave frequency band.

11. The method of claim 1, wherein storing the at least image data or audio data comprises capturing the image data and storing the captured image data in an image format.

12. The method of claim 1, wherein storing the at least image data or audio data comprises matching the image data and audio data in consideration of the playback time of the image data and audio data.

13. A mobile terminal comprising:
a memory configured to store information;
an output unit configured to output results of execution of an application in the mobile terminal, the results output external to the mobile terminal; and
a controller configured to execute the application, determine if a level of a brain wave classified into a specific frequency band is within a reference range and store at least image data or audio data relevant to the execution of the application in the memory if the level of the brain wave is within a reference range.

14. The mobile terminal of claim 13, wherein the reference range represents a specific state of mind of a user.

15. The mobile terminal of claim 13, wherein the controller is further configured to display an indicator to notify a user that the at least image data or audio data is being stored while storing the at least image data or audio data.

16. The mobile terminal of claim 13, wherein the at least image data or audio data comprises data output during a period of time when the brain wave is within the reference range.

17. The mobile terminal of claim 13, wherein the audio data comprises at least a user's voice or audio data output upon executing the application.

18. A method of controlling operation of a mobile terminal, the method comprising:
generating first brain wave information of a user of the mobile terminal;
receiving second brain wave information of a user of another mobile terminal;
comparing the first brain wave information to the second brain wave information;
generating brain harmony information indicating a level of harmony between the user of the mobile terminal and the user of the another mobile terminal based on the results of the comparison; and
controlling an operation relevant to the other mobile terminal based on the brain harmony information.

19. A method of controlling operation of a mobile terminal, the method comprising:
displaying an indicator associated with a reference brain wave during an application mode;
determining a level of pattern similarity between a received brain wave and the reference brain wave; and
performing an operation according to a command corresponding to the displayed indicator if the level of pattern similarity is higher than a predefined level.

\* \* \* \* \*